United States Patent
Hart et al.

(10) Patent No.: US 11,963,909 B2
(45) Date of Patent: *Apr. 23, 2024

(54) REGISTRATION OF LOI FIDUCIALS WITH CAMERA

(71) Applicant: AMO Development, LLC, Irvine, CA (US)

(72) Inventors: John S. Hart, San Carlos, CA (US); David A. Dewey, Sunnyvale, CA (US); Georg Schuele, Portolla Valley, CA (US); Phillip H. Gooding, Mountain View, CA (US); Christine J. Beltran, San Bruno, CA (US); Javier G. Gonzalez, Palo Alto, CA (US); Katrina B. Sheehy, Redwood City, CA (US); Jeffrey A. Golda, San Mateo, CA (US); Raymond Woo, Los Altos, CA (US); Madeleine C. O'Meara, San Francisco, CA (US); Noah Bareket, Saratoga, CA (US); Thomas Z. Teisseyre, Pacifica, CA (US); Bruce Woodley, Palo Alto, CA (US)

(73) Assignee: AMO Development, LLC, Irvine, CA (US)

(*) Notice: Subject to any disclaimer, the term of this patent is extended or adjusted under 35 U.S.C. 154(b) by 668 days.

This patent is subject to a terminal disclaimer.

(21) Appl. No.: 16/601,553

(22) Filed: Oct. 14, 2019

(65) Prior Publication Data

US 2020/0038245 A1 Feb. 6, 2020

Related U.S. Application Data

(60) Division of application No. 15/139,021, filed on Apr. 26, 2016, now Pat. No. 10,441,465, which is a
(Continued)

(51) Int. Cl.
A61F 9/008 (2006.01)
A61B 3/00 (2006.01)
(Continued)

(52) U.S. Cl.
CPC ........ *A61F 9/00838* (2013.01); *A61B 3/1025* (2013.01); *A61B 3/1173* (2013.01);
(Continued)

(58) Field of Classification Search
CPC ... A61B 3/0025; A61B 3/1025; A61B 3/1173; A61B 3/14; A61B 18/20–18/28;
(Continued)

(56) References Cited

U.S. PATENT DOCUMENTS

| 5,177,511 A | 1/1993 | Feuerstein et al. |
| 5,720,894 A | 2/1998 | Neev et al. |

(Continued)

FOREIGN PATENT DOCUMENTS

| CN | 2762415 Y | 3/2006 |
| EP | 2057973 A1 | 5/2009 |

(Continued)

OTHER PUBLICATIONS

Lynch., et al., "Beam Manipulation: Prism vs. Mirrors", Originally published in Germany on Nov. 12, 2009, Photonik, pp. 45-47.

*Primary Examiner* — Jonathan T Kuo
*Assistant Examiner* — Vynn V Huh
(74) *Attorney, Agent, or Firm* — Johnson & Johnson Surgical Vision, Inc.

(57) ABSTRACT

A method and surgical system including a laser source for generating a pulsed laser beam, an imaging system including a detector, shared optics configured for directing the pulsed laser beam to an object to be sampled and confocally deflecting back-reflected light from the object to the detector, a patient interface, through which the pulsed laser beam
(Continued)

is directed, the patient interface having, a cup with a large and small opening, and a notched ring inside the cup; and a controller operatively coupled to the laser source, the imaging system and the shared optics, the controller configured to align the eye for procedure.

10 Claims, 44 Drawing Sheets

Related U.S. Application Data continuation-in-part of application No. 14/576,593, filed on Dec. 19, 2014, now Pat. No. 10,123,696.

(60) Provisional application No. 62/043,749, filed on Aug. 29, 2014, provisional application No. 61/970,854, filed on Mar. 26, 2014.

(51) Int. Cl.
  *A61B 3/10* (2006.01)
  *A61B 3/117* (2006.01)
  *A61B 3/14* (2006.01)
  *A61F 9/007* (2006.01)

(52) U.S. Cl.
  CPC ............ *A61B 3/14* (2013.01); *A61F 9/00754* (2013.01); *A61F 9/008* (2013.01); *A61B 3/0025* (2013.01); *A61F 2009/00846* (2013.01); *A61F 2009/00855* (2013.01); *A61F 2009/0087* (2013.01); *A61F 2009/00872* (2013.01); *A61F 2009/00878* (2013.01); *A61F 2009/00887* (2013.01); *A61F 2009/00889* (2013.01); *A61F 2009/00895* (2013.01)

(58) Field of Classification Search
  CPC .. A61F 2009/00846; A61F 2009/00855; A61F 2009/0087; A61F 2009/00872; A61F 2009/00878; A61F 2009/00887; A61F 2009/00889; A61F 2009/00895; A61F 9/00754; A61F 9/008; A61F 9/00838
  USPC ...................................................... 606/2–19
  See application file for complete search history.

(56) References Cited

U.S. PATENT DOCUMENTS

| | | | |
|---|---|---|---|
| 5,825,533 A | 10/1998 | Yonezawa | |
| 5,957,915 A | 9/1999 | Trost | |
| 5,984,916 A | 11/1999 | Lai | |
| 6,019,472 A | 2/2000 | Koester et al. | |
| 6,454,761 B1 | 9/2002 | Freedman | |
| 6,577,394 B1 | 6/2003 | Zavislan | |
| 7,554,654 B2 | 6/2009 | Meeks et al. | |
| 7,655,002 B2 | 2/2010 | Myers et al. | |
| 7,717,907 B2 | 5/2010 | Ruiz et al. | |
| 8,262,646 B2 | 9/2012 | Frey et al. | |
| 8,350,183 B2 | 1/2013 | Vogel et al. | |
| 8,382,745 B2 | 2/2013 | Naranjo-Tackman et al. | |
| 8,414,564 B2 | 4/2013 | Goldshleger et al. | |
| 8,451,446 B2 | 5/2013 | Garab et al. | |
| 2002/0167655 A1 | 11/2002 | Friedman et al. | |
| 2003/0025842 A1 | 2/2003 | Saccomanno | |
| 2004/0012853 A1 | 1/2004 | Garcia et al. | |
| 2004/0095573 A1 | 5/2004 | Tsai et al. | |
| 2004/0102765 A1 | 5/2004 | Koenig | |
| 2007/0123761 A1 | 5/2007 | Daly et al. | |
| 2007/0282313 A1 | 12/2007 | Huang et al. | |
| 2010/0130966 A1 | 5/2010 | Brownell | |
| 2010/0137849 A1 | 6/2010 | Hanft et al. | |
| 2011/0172649 A1 | 7/2011 | Schuele et al. | |
| 2011/0251601 A1 | 10/2011 | Bissmann et al. | |
| 2011/0319873 A1 | 12/2011 | Raksi et al. | |
| 2011/0319875 A1 | 12/2011 | Loesel et al. | |
| 2012/0165798 A1 | 6/2012 | Rathjen | |
| 2013/0103014 A1* | 4/2013 | Gooding .............. | A61F 9/00825 606/4 |
| 2013/0158530 A1 | 6/2013 | Goldshleger et al. | |
| 2013/0201448 A1 | 8/2013 | Nozato | |
| 2013/0338648 A1 | 12/2013 | Hanebuchi et al. | |
| 2014/0058367 A1 | 2/2014 | Dantus | |
| 2014/0104576 A1 | 4/2014 | Bor et al. | |
| 2014/0128731 A1 | 5/2014 | Gonzalez et al. | |
| 2014/0128821 A1 | 5/2014 | Gooding et al. | |
| 2014/0128853 A1 | 5/2014 | Angeley et al. | |
| 2014/0157190 A1 | 6/2014 | Kim et al. | |
| 2014/0163534 A1 | 6/2014 | Angeley et al. | |
| 2014/0276671 A1 | 9/2014 | Gooding et al. | |
| 2014/0316389 A1 | 10/2014 | Schuele et al. | |
| 2014/0362882 A1 | 12/2014 | Sgandurra et al. | |
| 2015/0272782 A1 | 10/2015 | Schuele et al. | |
| 2016/0235588 A1 | 8/2016 | Hart et al. | |
| 2016/0250068 A1 | 9/2016 | Dewey et al. | |

FOREIGN PATENT DOCUMENTS

| | | | |
|---|---|---|---|
| WO | 02088818 A1 | 11/2002 | |
| WO | 2007143111 A2 | 12/2007 | |
| WO | 2009033110 A2 | 3/2009 | |
| WO | 2009040591 A1 | 4/2009 | |
| WO | 2011091326 A1 | 7/2011 | |
| WO | 2011116306 A2 | 9/2011 | |
| WO | 2012135073 A2 | 10/2012 | |
| WO | WO-2014149774 A2 * | 9/2014 | ............ A61F 9/008 |
| WO | 2014158615 A1 | 10/2014 | |
| WO | 2014163891 A1 | 10/2014 | |

* cited by examiner

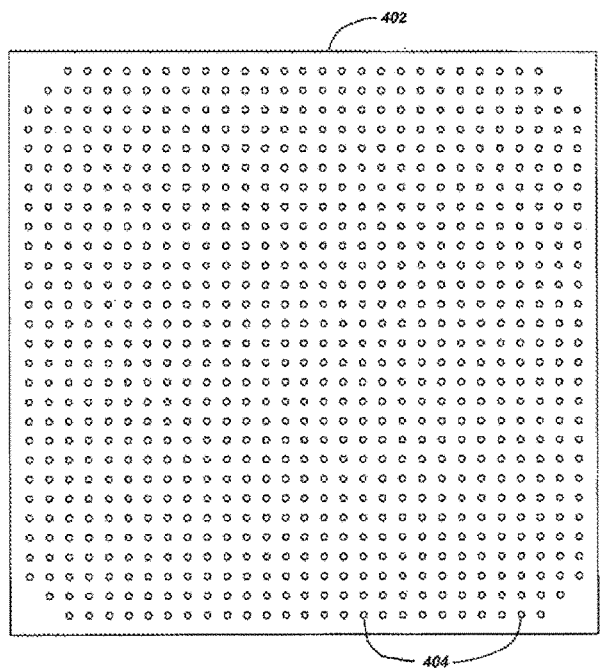
FIG. 7A
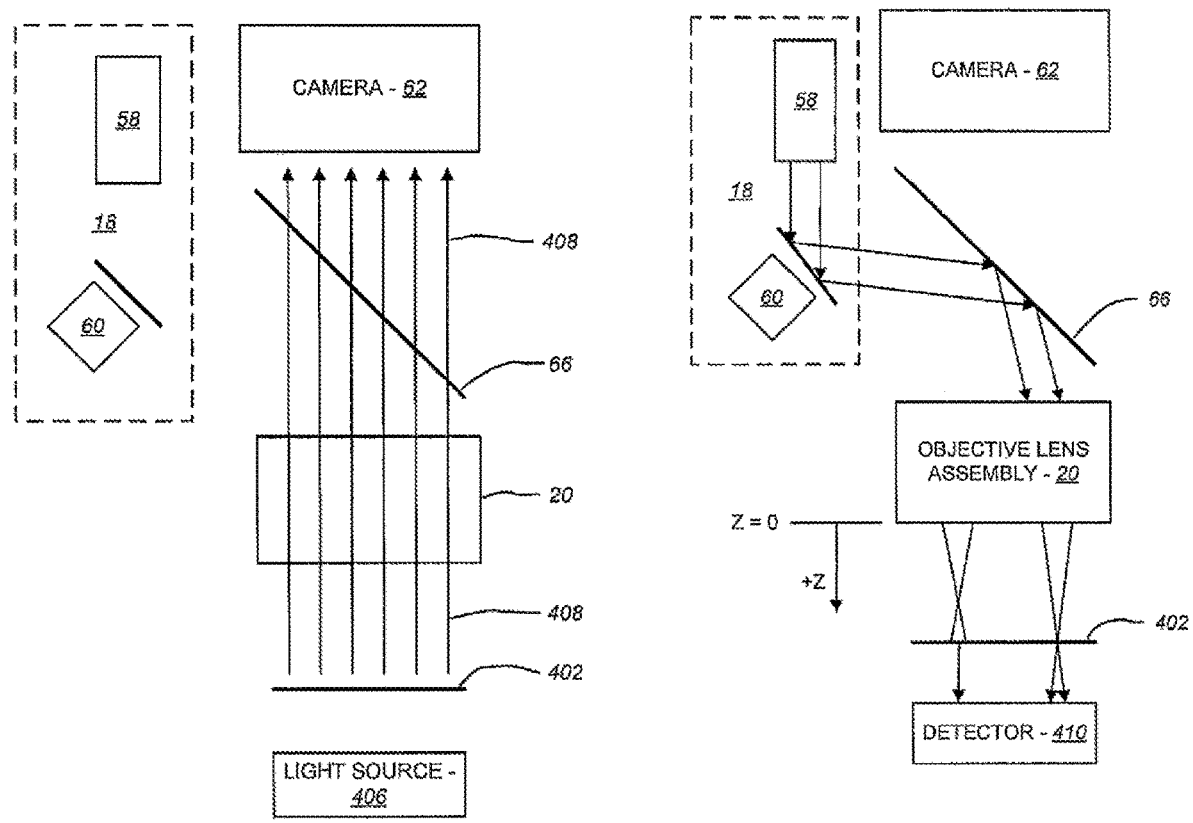
FIG. 7B
FIG. 7C

REGISTRATION OF LOI FIDUCIALS WITH CAMERA

CROSS REFERENCE TO RELATED APPLICATIONS

This application is a divisional of and claims priority to U.S. patent application Ser. No. 15/139,021, filed Apr. 26, 2016, which is a continuation-in-part of and claims priority to U.S. patent application Ser. No. 14/576,593, titled "Confocal Laser Eye Surgery Systems," filed Dec. 19, 2014, which claims priority to U.S. Provisional Application Ser. No. 61/970,854, filed Mar. 26, 2014, and to U.S. Provisional Application Ser. No. 62/043,749, filed Aug. 29, 2014, the entire contents of all of which applications are incorporated herein as if fully set forth.

BACKGROUND

Cataract extraction is a frequently performed surgical procedure. Cataracts are formed when the crystalline lens of the eye opacifies. The cataract scatters light passing through the lens and may perceptibly degrade vision. A cataract can vary in degree from slight to complete opacity. Early in the development of an age-related cataract, the power of the lens may increase, causing near-sightedness (myopia). Gradual yellowing and opacification of the lens may reduce the perception of blue colors as those shorter wavelengths are more strongly absorbed and scattered within the cataractous lens. Over time, cataract formation may progress and gradually result in progressive vision loss.

Cataract treatment often involves eye surgery to remove the opaque crystalline lens. The cataractous lens is then replaced with an artificial intraocular lens (IOL). Each year, an estimated 19 million cataract surgeries are performed worldwide.

During cataract surgery, a technique termed phacoemulsification can be used, wherein an ultrasonic tip with associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by making an incision in the shape of a small round hole in the anterior side of the lens capsule. This procedure is referred to as an anterior capsulorhexis when manual tools are used for making the incisions, and as an anterior capsulotomy when a surgical laser system is used instead.

Previously, manual tools such as microkeratomes were used for making incisions such as those in the lens capsule to provide access to the lens nucleus. Over the years, however, surgical laser systems have become the tool of choice as they tend to lessen the chance of irregular, imprecise and inaccurate cuts and related complications. Laser eye surgery systems have been developed for various cataract procedures, including for instance: (1) creating one or more primary incisions or sideport incisions in the cornea to provide access for a cataract surgery instrument (such as a phacoemulsification tip) and/or to provide access for implantation of an intraocular lens, (2) incising the anterior lens capsule (anterior capsulotomy) to provide access for removing a cataractous lens, (3) segmenting and/or fragmenting a cataractous lens, (4) incising the posterior lens capsule (posterior capsulotomy) for various cataract-related procedures, and/or (5) creating one or more arcuate incisions in the cornea or in the limbus to reshape the cornea for treating refractive conditions.

Accurate placement of a capsulotomy incision, a primary incision, a sideport incision, and an arcuate incision can be important for achieving a successful outcome of cataract surgery. In automated laser surgical procedures, physicians generally provide the necessary parameters for identifying the number, the placement and the size of incisions based on pre-treatment measurements. But, errors in data entry or lack of proper calibration of the laser surgical system can potentially lead to the placement of incisions at locations other than at the locations prescribed by the user. Moreover, some laser surgery systems do not allow real time confirmation of the location of the incision at the predetermined location, or do not provide warnings to the user if the actual placement of incisions during an automated scan is different from the intended location of those incisions.

Thus, methods and systems that introduce additional safeguards, such as verifying the location of a laser scan or ocular incision, would be helpful for treating patients with laser surgical systems.

SUMMARY

Hence, to obviate one or more problems due to limitations and disadvantages of the related art, many embodiments provide a method of verifying the placement of a laser scan at a predetermined location within an object comprises imaging at least a portion of the object, the resulting image comprising the predetermined location; identifying the predetermined location in the image, thereby establishing an expected scan location of the laser scan in the image; performing the laser scan on the object by scanning a focal point of a laser beam in a scanned area; detecting a luminescence from the scanned area and identifying an actual scanned location within the image based on the detected luminescence; and verifying whether the laser scan was at the predetermined location based on a difference between the actual scanned location and expected scan location. Preferably, the laser beam is a pulsed laser beam having a wavelength of 320 nm to 370 nm. The luminescence preferably has a wavelength of 400 nm or more. The step of verifying the laser scan is at the predetermined location comprises determining whether a distance between the actual scanned location and the expected scan location is within a predetermined threshold.

In many embodiments, the object is a human eye. In other embodiments, the object is a calibration apparatus.

In many embodiments, the image comprises an array of pixels. The expected scan location preferably comprises one or more pixels selected from amongst the array of pixels. Also, the actual scanned location preferably comprises one or more pixels selected from the array of pixels. Preferably, verifying the laser scan at the predetermined location comprises determining whether a distance between the actual scanned location and the expected scan location is within a predetermined threshold.

In many embodiments, the method further comprises periodically re-imaging the object, thereby obtaining one or more successive images of the object, and identifying an actual scanned location by comparing a detected luminescence of a same pixel in the array between two of the successive images. Preferably, the methods include identifying a direction of the scan by comparing an actual scanned location in between two or more of the successive images.

A method of verifying the placement of an ocular incision by a laser surgical system at a predetermined location within an eye comprises imaging at least a portion of the eye, the resulting image comprising the predetermined location for a laser scan corresponding to the ocular incision; identifying the predetermined location in the image, thereby establishing an expected scan location of the ocular incision in the image; performing a laser scan on the object by scanning a focal point of the laser beam in a scanned area, the laser scan being configured in a scan pattern for performing the ocular incision; detecting a luminescence from the scanned area and identifying an actual scanned location within the image based on the detected luminescence; and verifying the placement of an ocular incision based on the difference between the actual scanned location and expected scan location. The luminescence preferably has a wavelength of 400 nm or more. The step of verifying the laser scan is at the predetermined location comprises determining whether a distance between the actual scanned location and the expected scan location is within a predetermined threshold.

In many embodiments, the image comprises an array of pixels. The expected scan location preferably comprises one or more pixels selected from amongst the array of pixels. Also, the actual scanned location preferably comprises one or more pixels selected from the array of pixels. Preferably, verifying the laser scan at the predetermined location comprises determining whether a distance between the actual scanned location and the expected scan location is within a predetermined threshold.

In many embodiments, the method further comprises periodically re-imaging the object, thereby obtaining one or more successive images of the eye, and identifying an actual scanned location by comparing a detected luminescence of a same pixel in the array between two of the successive images. Preferably, the methods include identifying a direction of the scan by comparing an actual scanned location in between two or more of the successive images.

In many embodiments, a method of verifying the calibration of a laser eye surgical system comprises imaging at least a portion of a calibration apparatus having at least one emissive surface, the resulting image comprising a predetermined location for a laser scan; identifying the predetermined location in the image, thereby establishing an expected scan location of the laser scan in the image; performing the laser scan of the calibration apparatus by scanning a focal point of the laser beam in a scanned area; detecting a luminescence from the scanned area and identifying an actual scanned location within the image based on the detected luminescence; and determining whether the laser surgical system is calibrated based on a difference between the actual scanned location and expected scan location. The laser beam preferably has a wavelength of 320 nm to 370 nm. The luminescence preferably has a wavelength of 400 nm or more. The step of verifying the laser scan is at the predetermined location preferably comprises determining whether a distance between the actual scanned location and the expected scan location is within a predetermined threshold.

In many embodiments, the image comprises an array of pixels. The expected scan location preferably comprises one or more pixels selected from amongst the array of pixels. Also, the actual scanned location preferably comprises one or more pixels selected from the array of pixels. Preferably, verifying the laser scan at the predetermined location comprises determining whether a distance between the actual scanned location and the expected scan location is within a predetermined threshold.

In many embodiments, the method further comprises periodically re-imaging the object, thereby obtaining one or more successive images of the calibration apparatus, and identifying an actual scanned location by comparing a detected luminescence of a same pixel in the array between two of the successive images. Preferably, the methods include identifying a direction of the scan by comparing an actual scanned location in between two or more of the successive images.

In many embodiments, a laser eye surgical system, comprises a laser source for generating a pulsed laser beam; an imaging system comprising a detector; shared optics configured for directing the pulsed laser beam to an object to be sampled and confocally deflecting back-reflected light from the object to the detector; and a controller operatively coupled to the laser source, the imaging system and the shared optics. The controller configured to:

(a) receive one or more parameters defining one or more ocular incisions;
(b) image the eye with the imaging apparatus and identify an expected scan location within the image corresponding to the one or more ocular incisions based on the one or more parameters;
(c) scan the focal point of a laser beam;
(d) detect luminescence from the region scanned;
(e) identify the actual scanned location within the image based on the detected luminescence; and
(f) provide a warning to the user if a difference between the actual scanned location and the expected is not within a predetermined threshold value.

The controller may be configured to verify the laser scan is at the predetermined location when a distance between the actual scanned location and the expected scan location is within a predetermined threshold.

The laser beam preferably has a wavelength of 320 nm to 370 nm, and the luminescence has a wavelength of 400 nm or more.

In many embodiments, the image preferably comprises an array of pixels. The expected scan location preferably comprises one or more pixels selected from amongst the array of pixels, and the actual scanned location comprises one or more pixels selected from the array of pixels.

The controller is preferably configured to periodically re-image the eye, thereby obtaining one or more successive images and identifying an actual scanned location by comparing a detected luminescence of a same pixel in the array between two of the successive images. The controller is also preferably configured to identify direction of the scan by comparing an actual scanned location in between two or more of the successive images.

This summary and the following description are merely exemplary, illustrative, and explanatory, and are not intended to limit, but to provide further explanation of the invention as claimed. Additional features, aspects, objects and advantages of embodiments of this invention are set forth in the descriptions, drawings, and the claims, and in part, will be apparent from the drawings and detailed description, or may be learned by practice. The claims are incorporated by reference.

BRIEF DESCRIPTION OF THE FIGURES

The novel features of the invention are set forth with particularity in the appended claims. A better understanding of the features and advantages of the present invention will be obtained by referring to the following detailed description that sets forth illustrative embodiments using principles of the invention, as well as to the accompanying drawings of which:

FIG. 7A is a plan view illustrating a calibration plate, according to many embodiments, that can be used to calibrate the laser surgery system of FIG. 1.

FIG. 7B is a schematic diagram illustrating using the calibration plate of FIG. 10A to calibrate a camera of the laser surgery system of FIG. 1.

FIG. 7C is a schematic diagram illustrating using the calibration plate of FIG. 10A to calibrate the scanning assembly of the laser surgery system of FIG. 1.

FIG. 23A is a schematic diagram illustrating an embodiment in which a confocal bypass assembly is not placed in the optical path of the electromagnetic beam. FIG. 23B is a schematic diagram illustrating an embodiment in which a confocal bypass assembly is placed in the optical path of the electromagnetic beam.

DETAILED DESCRIPTION

The following description describes various embodiments of the present invention. For purposes of explanation, specific configurations and details are set forth so as to provide a thorough understanding of the embodiments. It will also, however, be apparent to one skilled in the art that embodiments of the present invention can be practiced without certain specific details. Further, to avoid obscuring the embodiment being described, various well-known features may be omitted or simplified in the description.

Systems for imaging and/or treating an eye of a patient are provided. In many embodiments, a shared optics provides a variable optical path by which a portion of an electromagnetic beam reflected from a focal point disposed within the eye is directed to a path length insensitive imaging assembly, such as a confocal detection assembly. In many embodiments, the shared optics is configured to accommodate movement of the patient while maintaining alignment between an electromagnetic radiation beam and the patient. The electromagnetic radiation beam can be configured for imaging the eye, can be configured for treating the eye, and can be configured for imaging and treating the eye.

Figure 1:
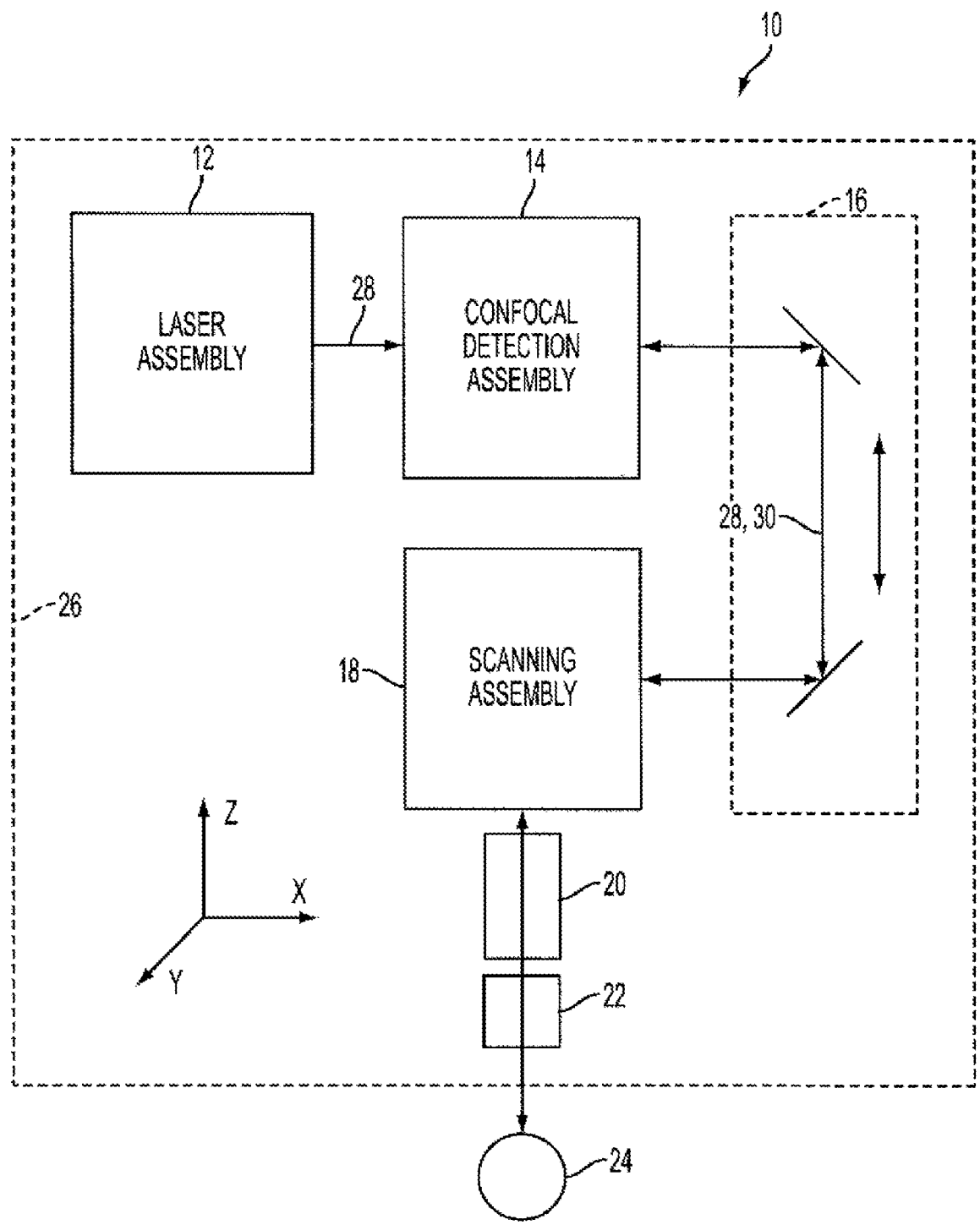
FIG. 1 is a schematic diagram of a laser surgery system, according to many embodiments, in which a patient interface device is coupled to a laser assembly and a detection assembly by way of a scanning assembly and shared optics that supports the scanning assembly.

Referring now to the drawings in which like numbers reference similar elements, FIG. 1 schematically illustrates a laser surgery system 10, according to many embodiments. The laser surgery system 10 includes a laser assembly 12, a confocal detection assembly 14, a shared optics 16, a scanning assembly 18, an objective lens assembly 20, and a patient interface device 22. The patient interface device 22 is configured to interface with a patient 24. The patient interface device 22 is supported by the objective lens assembly 20. The objective lens assembly 20 is supported by the scanning assembly 18. The scanning assembly 18 is supported by the shared optics 16. The shared optics 16 has a portion having a fixed position and orientation relative to the laser assembly 12 and the confocal detection assembly 14. In many embodiments, the patient interface device 22 is configured to interface with an eye of the patient 24. For example, the patient interface device 22 can be configured to be vacuum coupled to an eye of the patient 24 such as described in U.S. Publication No. 2014-0128821 A1 (co-pending U.S. patent application Ser. No. 14/068,994, entitled "Liquid Optical Interface for Laser Eye Surgery System," filed Oct. 31, 2013). The laser surgery system 10 can further optionally include a base assembly 26 that can be fixed in place or repositionable. For example, the base assembly 26 can be supported by a support linkage that is configured to allow selective repositioning of the base assembly 26 relative to a patient and secure the base assembly 26 in a selected fixed position relative to the patient. Such a support linkage can be supported in any suitable manner such as, for example, by a fixed support base or by a movable cart that can be repositioned to a suitable location adjacent to a patient. In many embodiments, the support linkage includes setup joints with each setup joint being configured to permit selective articulation of the setup joint and can be selectively locked to prevent inadvertent articulation of the setup joint, thereby securing the base assembly 26 in a selected fixed position relative to the patient when the setup joints are locked.

In many embodiments, the laser assembly 12 is configured to emit an electromagnetic radiation beam 28. The beam 28 can include a series of laser pulses of any suitable energy level, duration, and repetition rate.

In certain embodiments, the laser assembly 12 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required to image and/or modify an intraocular target as compared to laser pulses having longer durations. In other embodiments, the laser pulses have a pulse duration generally between 1 ps and 100 ns.

The laser assembly 12 can produce laser pulses having a wavelength suitable to treat and/or image tissue. For example, the laser assembly 12 can be configured to emit an electromagnetic radiation beam 28 such as emitted by any of the laser surgery systems described in U.S. Publication No. US 2014-0163534 A1 (co-pending U.S. patent application Ser. No. 14/069,042, entitled "Laser Eye Surgery System," filed Oct. 31, 2013) and US Publication No. US 2011-0172649 A1 (co-pending U.S. patent application Ser. No. 12/987,069, entitled "Method and System For Modifying Eye Tissue and Intraocular Lenses," filed Jan. 7, 2011). For example, the laser assembly 12 can produce laser pulses having a wavelength from 1020 nm to 1050 nm. For example, the laser assembly 12 can have a diode-pumped solid-state configuration with a 1030(+/−5) nm center wavelength. As another example, the laser assembly 12 can produce ultraviolet light pulses having a wavelength of between 320 nm and 430 nm, preferably between 320 and 400 nm, preferably between 320 to 370 nm, and more preferably between 340 nm and 360 nm. In many embodiments, the laser pulses have a wavelength of 355 nm. The 320 nm to 430 nm light source may be, for instance, a Nd:YAG laser source operating at the 3rd harmonic wavelength, 355 nm.

When an ultraviolet wavelength is used, the pulse energy of the laser pulses is generally between 0.010 and 5000. In many embodiments, the pulse energy will be between 0.1 µJ and 100 µJ, or more precisely, between 0.1 µJ and 40 µJ, or between 0.1 µJ and 10 µJ.

When an ultraviolet wavelength is used, a pulse repetition rate of the laser pulses is generally between 500 Hz and 500 kHz. In many embodiments, the pulse repetition rate is between 1 kHz to 200 kHz, or between 1 KHz to 100 KHz.

When an ultraviolet wavelength is used, spot sizes of the laser pulses are generally smaller than 10 µm. In many embodiments, the spot size is preferably smaller than 5 µm, typically 0.5 µm to 3 µm.

When an ultraviolet wavelength is used, a pulse duration of the laser pulses is generally between 1 ps and 100 ns. In many embodiments, the pulse duration is between 100 ps to 10 ns, or between 100 ps and 1 ns. In a preferred embodiment, the pulse duration is between 300 ps and 700 ps, preferably 400 ps to 700 ps.

In some embodiments when an ultraviolet wavelength is used, the beam quality, also referred to as $M^2$ factor, is between 1 and 1.3. The $M^2$ factor is a common measure of the beam quality of a laser beam. In brief, the $M^2$ factor is defined as the ratio of a beam's actual divergence to the divergence of an ideal, diffraction limited, Gaussian TEM00 beam having the same waist size and location as is described in ISO Standard 11146.

In some embodiments when an ultraviolet wavelength is used, a peak power density, obtained by dividing the peak power of the laser pulse by the focal spot size, is generally expressed in units of GW/cm2. In general, the peak power density of the laser pulses should be sufficiently high to modify the ocular tissue to be treated. As would be understood by those ordinarily skilled, the peak power density depends upon a number of factors, including the wavelength of the selected laser pulses. In some embodiments, a peak power density is generally in the range of 100 GW/cm$^2$ to 800 GW/cm$^2$ will be used to cut ocular tissue with 355 nm light.

In some embodiments when an ultraviolet wavelength is used, the scan range of the laser surgical system is preferably in the range of 6 to 10 mm.

In some embodiments when an ultraviolet wavelength is used, spot spacing between adjacent laser pulses is typically in the range of about 0.20 µm to 10 µm, preferably 0.2 µm to 6 µm.

In some embodiments when an ultraviolet wavelength is used, a numerical aperture should be selected that preferably provides for the focal spot of the laser beam to be scanned over a scan range of 6 mm to 10 mm in a direction lateral to a Z-axis that is aligned with the laser beam. The NA of the system should be less than 0.6, preferably less than 0.5 and more preferably in a range of 0.05 to 0.4, typically between 0.1 and 0.3. In some specific embodiments, the NA is 0.15. For each selected NA, there are suitable ranges of pulse energy and beam quality (measured as an $M^2$ value) necessary to achieve a peak power density in the range required to cut the ocular tissue. Further considerations when choosing the NA include available laser power and pulse rate, and the time needed to make a cut. Further, in selection of an appropriate NA, it is preferable to ensure that there is a safe incidental exposure of the iris, and other ocular tissues, that are not targeted for cuts.

When UV wavelengths are used, the tissue modification is carried out using chromophore absorption without plasma formation and/or without bubble formation and an associated cavitation event. Here, chromophore absorption refers to the absorption of at least a portion of the ultraviolet light by one or more chemical species in the target area. The use of ultraviolet light significantly reduces the threshold for plasma formation and associated formation of cavitation bubbles but also decreases the threshold energy required for linear absorption enhanced photodecomposition without the formation of cavitation bubbles for a few reasons. First, the focused spot diameter scales linearly with wavelength which squares the peak radiant exposure within the focal plane. Second, the linear absorption of the material itself allows an even lower threshold for plasma formation or low density photodecomposition as initially more laser energy is absorbed in the target structure. Third, the use of UV laser pulses in the nanosecond and sub-nanosecond regime enables linear absorption enhanced photodecomposition and chromophore guided ionization.

Furthermore, this chromophore guided ionization when using ultraviolet wavelength strongly lowers the threshold for ionization in case of plasma formation as well lowers the threshold for low density photodecomposition for material modification or alteration without cavitation even under very weak absorption. The linear absorption also allows for the specific treatment of topical lens structures (e.g. the lens capsule) as the optical penetration depth of the laser beam is limited by the linear absorption of the lens. This is especially true for aged lenses which absorption in the UV-blue spectral region increases strongly compared to young lenses.

The laser assembly 12 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly and a fixed optical relay to transfer the laser pulses over a distance while accommodating laser pulse beam positional and/or directional variability, thereby providing increased tolerance for component variation.

In many embodiments, the laser assembly 12 and the confocal detection assembly 14 have fixed positions relative to the base assembly 26. The beam 28 emitted by the laser assembly 12 propagates along a fixed optical path through the confocal detection assembly 14 to the shared optics 16. The beam 28 propagates through the shared optics 16 along a variable optical path 30, which delivers the beam 28 to the scanning assembly 18. In many embodiments, the beam 28 emitted by the laser assembly 12 is collimated so that the beam 28 is not impacted by patient movement induced changes in the length of the optical path between the laser assembly 12 and the scanner 16. The scanning assembly 18 is operable to scan the beam 28 (e.g., via controlled variable deflection of the beam 28) in at least one dimension. In many embodiments, the scanning assembly 18 is operable to scan the beam 28 in two dimensions transverse to the direction of propagation of the beam 28 and is further operable to scan the location of a focal point of the beam 28 in the direction of propagation of the beam 28. The scanned beam is emitted from the scanning assembly 18 to propagate through the objective lens assembly 20, through the interface device 22, and to the patient 24.

The shared optics 16 is configured to accommodate a range of movement of the patient 24 relative to the laser assembly 12 and the confocal detection assembly 14 in one or more directions while maintaining alignment of the beam 28 emitted by the scanning assembly 18 with the patient 24. For example, in many embodiments, the shared optics 16 is configured to accommodate a range movement of the patient 24 in any direction defined by any combination of unit orthogonal directions (X, Y, and Z).

The shared optics 16 supports the scanning assembly 18 and provides the variable optical path 30, which changes in response to movement of the patient 24. Because the patient interface device 22 is interfaced with the patient 24, movement of the patient 24 results in corresponding movement of the patient interface device 22, the objective lens assembly 20, and the scanning assembly 18. The shared optics 16 can include, for example, any suitable combination of a linkage that accommodates relative movement between the scanning assembly 18 and, for example, the confocal detection assembly 24, and optical components suitably tied to the linkage so as to form the variable optical path 30.

A portion of the electromagnetic radiation beam 28 that is reflected by eye tissue at the focal point propagates back to the confocal detection assembly 14. Specifically, a reflected portion of the electromagnetic radiation beam 28 travels back through the patient interface device 22, back through the objective lens assembly 20, back through (and de-scanned by) the scanning assembly 18, back through the shared optics 16 (along the variable optical path 30), and to the confocal detection assembly 14. In many embodiments, the reflected portion of the electromagnetic radiation beam that travels back to the confocal detection assembly 14 is directed to be incident upon a sensor that generates an intensity signal indicative of intensity of the incident portion of the electromagnetic radiation beam. The intensity signal, coupled with associated scanning of the focal point within the eye, can be processed in conjunction with the parameters of the scanning to, for example, image/locate structures of the eye, such as the anterior surface of the cornea, the posterior surface of the cornea, the iris, the anterior surface of the lens capsule, and the posterior surface of the lens capsule. In many embodiments, the amount of the reflected electromagnetic radiation beam that travels to the confocal detection assembly 14 is substantially independent of expected variations in the length of the variable optical path 30 due to patient movement, thereby enabling the ability to ignore patient movements when processing the intensity signal to image/locate structures of the eye.

Figure 2:
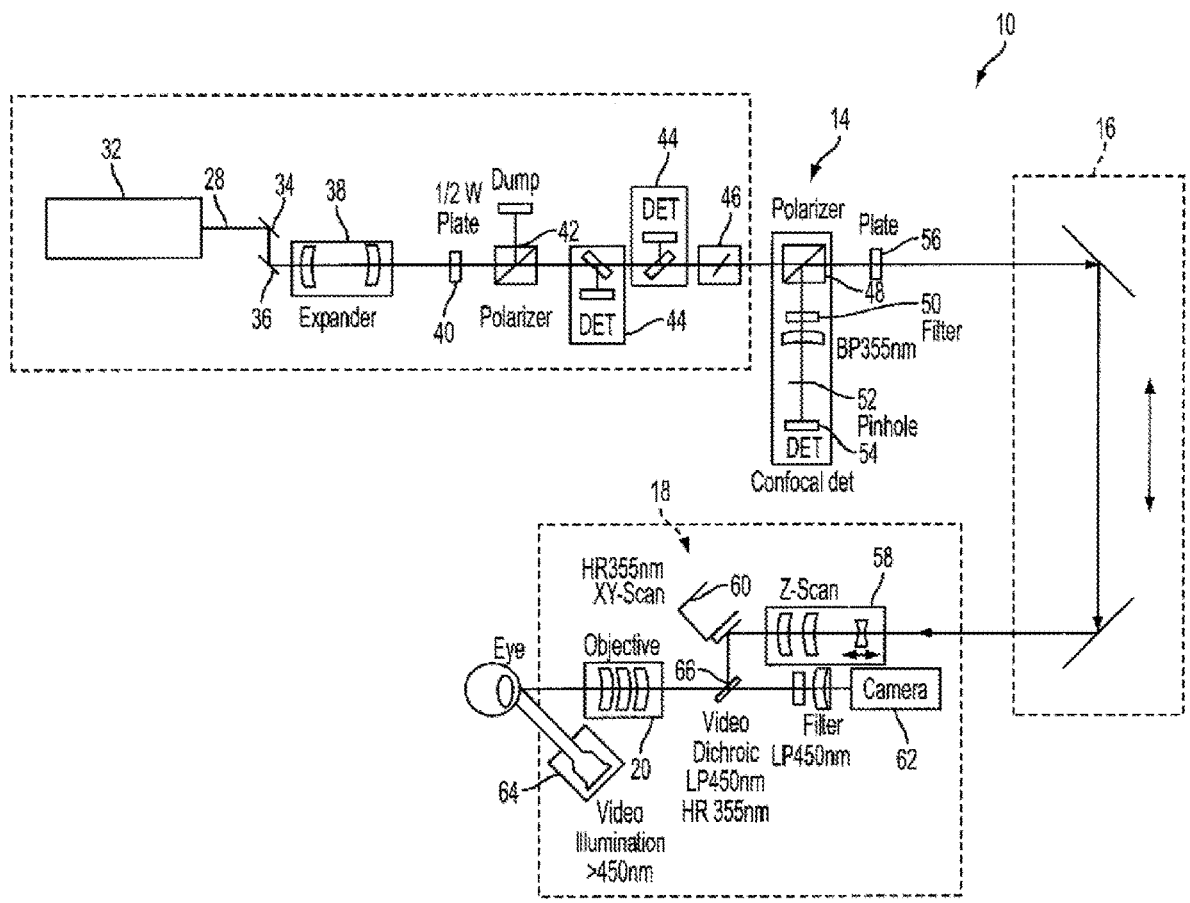
FIG. 2 is a schematic diagram of an embodiment of the laser surgery system of FIG. 1.

FIG. 2 schematically illustrates details of an embodiment of the laser surgery system 10. Specifically, example configurations are schematically illustrated for the laser assembly 12, the confocal detection assembly 14, and the scanning assembly 18. As shown in the illustrated embodiment, the laser assembly 12 can include an laser 32 (e.g., a femtosecond laser), alignment mirrors 34, 36, a beam expander 38, a one-half wave plate 40, a polarizer and beam dump device 42, output pickoffs and monitors 44, and a system-controlled shutter 46. The electromagnetic radiation beam 28 output by the laser 32 is deflected by the alignment mirrors 34, 36. In many embodiments, the alignment mirrors 34, 36 are adjustable in position and/or orientation so as to provide the ability to align the beam 28 with the downstream optical path through the downstream optical components. Next, the beam 28 passes through the beam expander 38, which increases the diameter of the beam 28. Next, the expanded beam 28 passes through the one-half wave plate 40 before passing through the polarizer. The beam exiting the laser is linearly polarized. The one-half wave plate 40 can rotate this polarization. The amount of light passing through the polarizer depends on the angle of the rotation of the linear polarization. Therefore, the one-half wave plate 40 with the polarizer acts as an attenuator of the beam 28. The light rejected from this attenuation is directed into the beam dump. Next, the attenuated beam 28 passes through the output pickoffs and monitors 44 and then through the system-controlled shutter 46. By locating the system-controlled shutter 46 downstream of the output pickoffs and monitors 44, the power of the beam 28 can be checked before opening the system-controlled shutter 46.

As shown in the illustrated embodiment, the confocal detection assembly 14 can include a polarization-sensitive device such as a polarized or unpolarized beam splitter 48, a filter 50, a focusing lens 51, a pinhole aperture 52, and a detection sensor 54. A one-quarter wave plate 56 is disposed downstream of the polarized beam splitter 48. The beam 28 as received from the laser assembly 12 is polarized so as to pass through the polarized beam splitter 48. Next, the beam 28 passes through the one-quarter wave plate 56, thereby rotating the polarization axis of the beam 28. A quarter rotation is a presently preferred rotation amount. After reflecting from the focal point in the eye, the returning reflected portion of the beam 28 passes back through the one-quarter wave plate 56, thereby further rotating the polarization axis of the returning reflected portion of the beam 28. Ideally, after passing back through the one-quarter wave plate 56, the returning reflected portion of the beam has experienced a total polarization rotation of 90 degrees so that the reflected light from the eye is fully reflected by the polarized beam splitter 48. The birefringence of the cornea can also be taken into account if, for example, the imaged structure is the lens. In such a case, the plate 56 can be adjusted and/or configured so that the double pass of the plate 56 as well as the double pass of the cornea sum up to a polarization rotation of 90 degrees. Because the birefringence of the cornea may be different from patient to patient, the configuration/adjustment of the plate 56 can be done dynamically so as to optimize the signal returning to the detection sensor 54. Accordingly, the returning reflected portion of the beam 28 is now polarized to be at least partially reflected by the polarized beam splitter 48 so as to be directed through the filter 50, through the lens 51, and to the pinhole aperture 52. The filter 50 can be configured to block wavelengths other than the wavelengths of interest. The pinhole aperture 52 is configured to block any returning reflected portion of the beam 28 reflected from locations other than the focal point from reaching the detection sensor 54. Because the amount of returning reflected portion of the beam 28 that reaches the detection sensor 54 depends upon the nature of the tissue at the focal point of the beam 28, the signal generated by the detection sensor 54 can be processed in combination with data regarding the associated locations of the focal point so as to generate image/location data for structures of the eye.

In this embodiment, the same laser assembly may be used both for treatment (i.e. modification) and imaging of the target tissue. For instance, the target tissue may be imaged by raster scanning pulsed laser beam 28 along the target tissue to provide for a plurality of data points, each data point having a location and intensity associated with it for imaging of the target tissue. In some embodiments, the raster scan is selected to deliver a sparse pattern in order to limit the patient's exposure, while still discerning a reasonable map of the intraocular targets. In order to image the target tissue, the treatment laser beam (i.e. the laser beam having the parameters suitably chosen as described above for the modification of tissue) is preferably attenuated to the nano-Joule level for imaging of the structures to be treated. When used for imaging, the attenuated laser beam may be referred to as an imaging beam. In many embodiments, the treatment beam and the imaging beam may be the same except that the pulse energy of the laser source is lower than the treatment beam when the laser beam is used for imaging. In many embodiments, the pulse energy of the laser beam when used for imaging is preferably from about 0.1 nJ to 10 nJ, preferably less than 2 nJ and more preferably less than 1.8 nJ. The use of the same laser beam for both treatment and imaging provides for the most direct correlation between the position of the focal locations for imaging and treatment—they are the same beam. This attenuated probe beam can is preferably used directly in a back reflectance measuring configuration, but, alternatively, may be used indirectly in a fluorescence detection scheme. Since increases in both backscatter and fluorescence within tissue structures will be evident, both approaches have merit.

In a preferred embodiment, imaging of a first target area to be modified is performed sequentially with the modification of the tissue in the first target area before moving on to a second, different, target area, i.e. imaging is performed sequentially with treatment in a predetermined target area. Thus, for instance imaging of the lens capsule is preferably followed by treatment of the lens capsule before imaging is carried out on other either structures, such as the cornea or iris. In another embodiment, imaging of a first target area where a first incision to be place is performed sequentially with the scanning the treatment beam to perform the incision in the first target area before moving on to a second target area for performing a second incision, i.e. imaging of the area to be incised is performed sequentially with scanning the treatment beam to perform in the predetermined target area.

In another embodiment, a cataract procedure comprises a capsulotomy incision, and at least one of a cataract incision and a limbal relaxing incision. In one embodiment, imaging of the target tissue where the capsulotomy is to be performed is followed by scanning of the treatment to perform the capsulotomy, and then the treatment beam is scanned to perform the capsulotomy. Subsequently, imaging of the target tissue where the at least one of the cataract incisions (CI) and the limbal relaxing incision (LRI) is carried out and then the treatment beam is scanned to perform the at least one of the LRI and the CI. When an LRI is selected, this minimizes the chance for the patient to move between imaging and treatment for the LRIs which are the most critical/sensitive to eye movements between image and treatment.

As shown in the illustrated embodiment, the scanning assembly 18 can include a z-scan device 58 and a xy-scan device 60. The z-scan device 58 is operable to vary a convergence/divergence angle of the beam 28 and thereby change a location of the focal point in the direction of propagation of the beam 28. For example, the z-scan device 58 can include one or more lenses that are controllably movable in the direction of propagation of the beam 28 to vary a convergence/divergence angle of the beam 28. The xy-scan device 60 is operable to deflect the beam 28 in two dimensions transverse to the direction of propagation of the beam 28. For example, the xy-scan device 60 can include one or more mirrors that are controllably deflectable to scan the beam 28 in two dimensions transverse to the direction of propagation of the beam 28. Accordingly, the combination of the z-scan device 58 and the xy-scan device 60 can be operated to controllably scan the focal point in three dimensions, for example, within the eye of the patient.

As shown in the illustrated embodiment, a camera 62 and associated video illumination 64 can be integrated with the scanning assembly 18. The camera 62 and the beam 28 share a common optical path through the objective lens assembly 20 to the eye. A video dichroic 66 is used to combine/separate the beam 28 with/from the illumination wavelengths used by the camera. For example, the beam 28 can have a wavelength of about 355 nm and the video illumination 64 can be configured to emit illumination having wavelengths greater than 450 nm. Accordingly, the video dichroic 66 can be configured to reflect the 355 nm wavelength while transmitting wavelengths greater than 450 nm.

Figure 3:
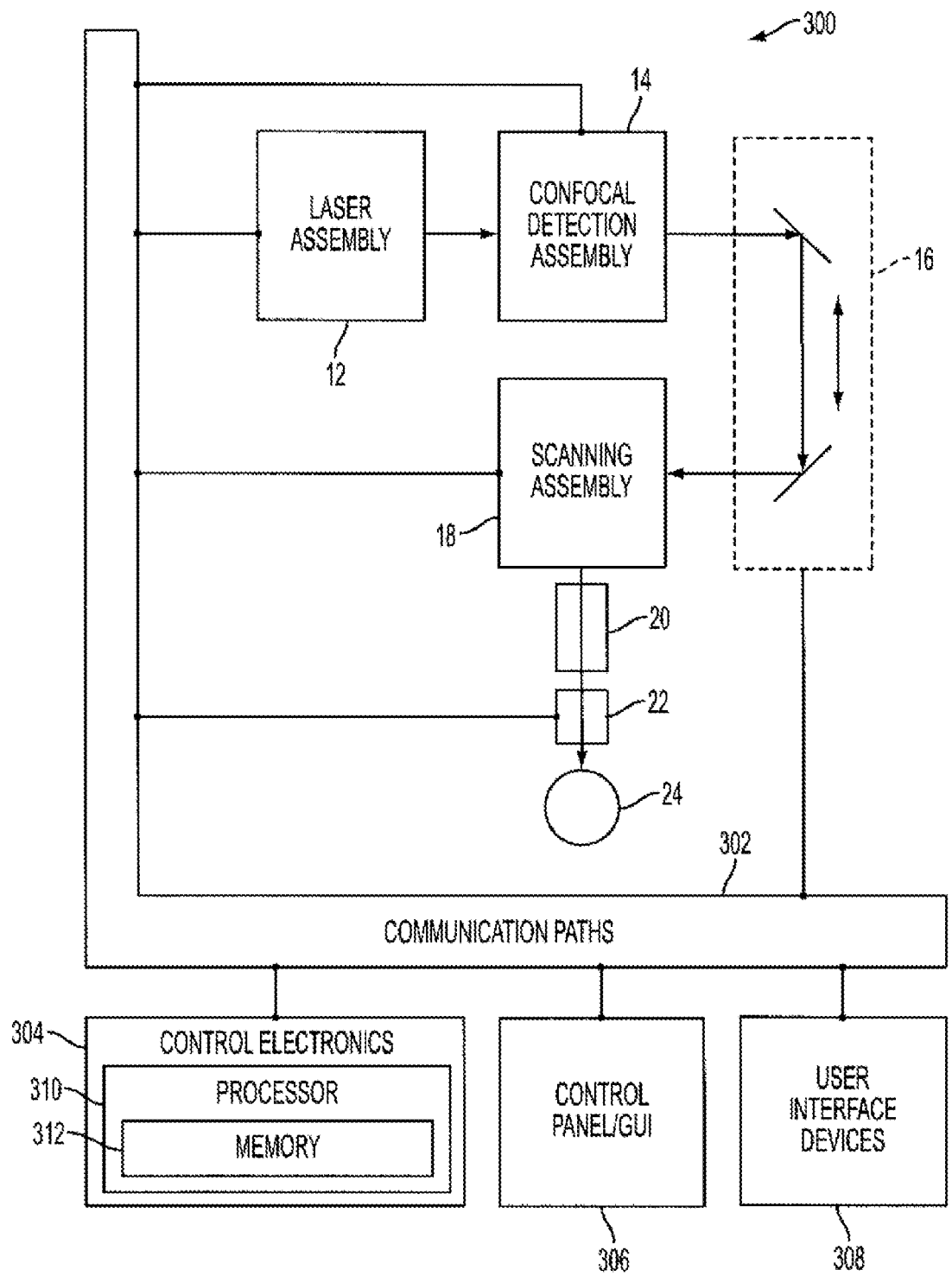
FIG. 3 is a schematic diagram of an embodiment of the laser surgery system of FIG. 1.

FIG. 3 schematically illustrates a laser surgery system 300, according to many embodiments. The laser surgery system 300 includes the laser assembly 12, the confocal detection assembly 14, the shared optics 16, the scanning assembly 18, the objective lens assembly 20, the patient interface 22, communication paths 302, control electronics 304, control panel/graphical user interface (GUI) 306, and user interface devices 308. The control electronics 304 includes processor 310, which includes memory 312. The patient interface 22 is configured to interface with a patient 24. The control electronics 304 is operatively coupled via the communication paths 302 with the laser assembly 12, the confocal detection assembly 14, the shared optics 16, the scanning assembly 18, the control panel/GUI 306, and the user interface devices 308.

The scanning assembly 18 can include a z-scan device and a xy-scan device. The laser surgery system 300 can be configured to focus the electromagnetic radiation beam 28 to a focal point that is scanned in three dimensions. The z-scan device can be operable to vary the location of the focal point in the direction of propagation of the beam 28. The xy-scan device can be operable to scan the location of the focal point in two dimensions transverse to the direction of propagation of the beam 28. Accordingly, the combination of the z-scan device and the xy-scan device can be operated to controllably scan the focal point of the beam in three dimensions, including within a tissue of the patient 24 such as within an eye tissue of the patient 24. The scanning assembly 18 is supported by the shared optics 16, which may be configured to accommodate patient movement induced movement of the scanning assembly 18 relative to the laser assembly 12 and the confocal detection assembly 14 in three dimensions.

The patient interface 22 is coupled to the patient 24 such that the patient interface 22, the objective lens assembly 20, and the scanning assembly 18 move in conjunction with the patient 24. For example, in many embodiments, the patient interface 22 employs a suction ring that is vacuum attached to an eye of the patient 24. The suction ring can be coupled with the patient interface 22, for example, using vacuum to secure the suction ring to the patient interface 22.

The control electronics 304 controls the operation of and/or can receive input from the laser assembly 12, the confocal detection assembly 14, the free-floating assembly 16, the scanning assembly 18, the patient interface 22, the control panel/GUI 306, and the user interface devices 308 via the communication paths 302. The communication paths 302 can be implemented in any suitable configuration, including any suitable shared or dedicated communication paths between the control electronics 304 and the respective system components.

The control electronics 304 can include any suitable components, such as one or more processors, one or more field-programmable gate arrays (FPGA), and one or more memory storage devices. In many embodiments, the control electronics 304 controls the control panel/GUI 306 to provide for pre-procedure planning according to user specified treatment parameters as well as to provide user control over the laser eye surgery procedure.

The control electronics 304 can include a processor/controller 310 that is used to perform calculations related to system operation and provide control signals to the various system elements. A computer readable medium 312 is coupled to the processor 310 in order to store data used by the processor and other system elements. The processor 310 interacts with the other components of the system as described more fully throughout the present specification. In an embodiment, the memory 312 can include a look up table that can be utilized to control one or more components of the laser system surgery system 300.

The processor 310 can be a general purpose microprocessor configured to execute instructions and data, such as a Pentium processor manufactured by the Intel Corporation of Santa Clara, California It can also be an Application Specific Integrated Circuit (ASIC) that embodies at least part of the instructions for performing the method according to the embodiments of the present disclosure in software, firmware and/or hardware. As an example, such processors include dedicated circuitry, ASICs, combinatorial logic, other programmable processors, combinations thereof, and the like.

The memory 312 can be local or distributed as appropriate to the particular application. Memory 312 can include a number of memories including a main random access memory (RAM) for storage of instructions and data during program execution and a read only memory (ROM), in which fixed instructions are stored. Thus, the memory 312 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 308 can include any suitable user input device suitable to provide user input to the control electronics 304. For example, the user interface devices 308 can include devices such as, for example, a touch-screen display/input device, a keyboard, a footswitch, a keypad, a patient interface radio frequency identification (RFID) reader, an emergency stop button, and a key switch.

Certain acts or steps in connection with the methods and systems of verifying the location of a laser scan in an object, preferably an eye, are shown in FIG. 2. In some embodiments, the object is an eye and the methods and acts of verifying the locations of the laser scan is operable to verify the location of an incision in ocular surgical procedures, including cataract surgery. In other embodiments, the object is a calibration apparatus, and the methods and acts are operable to verify the calibration of a laser surgical system, preferably a laser eye surgical system.

Figure 4:
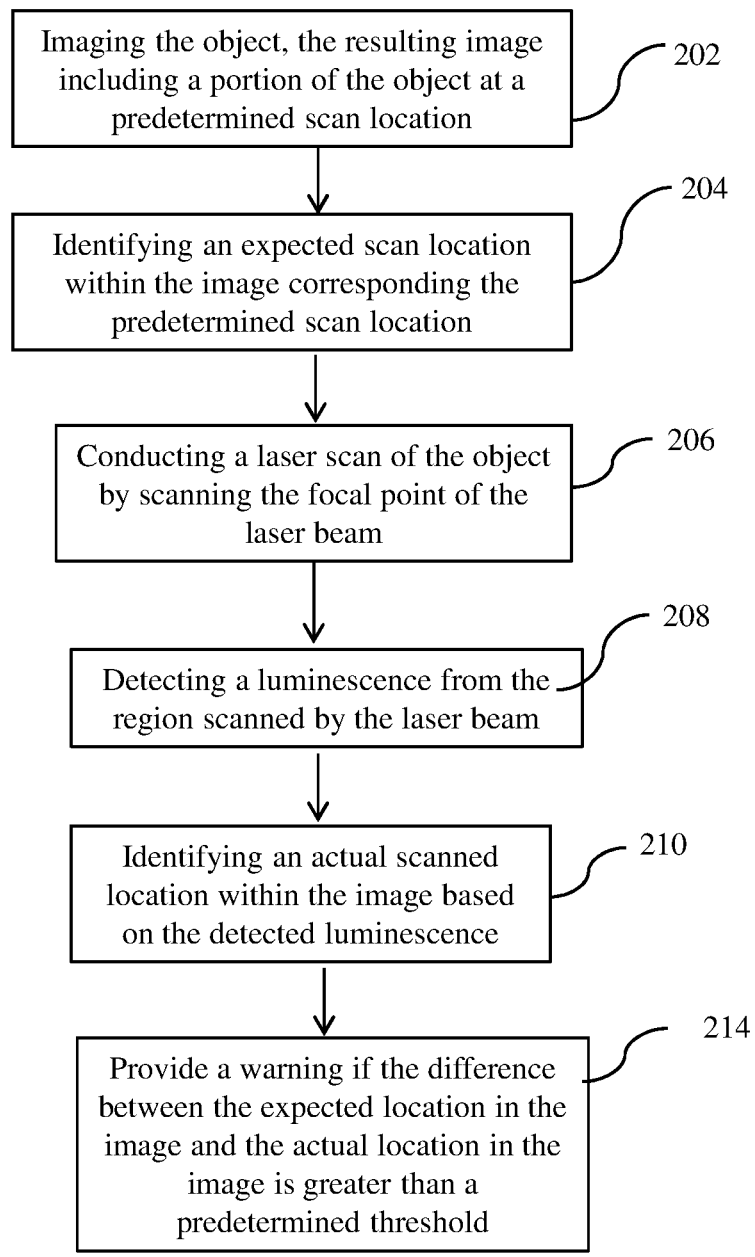
FIG. 4 is a block diagram illustrating several acts of the methods and acts for laser scan verification in many embodiments.
Figure 5:
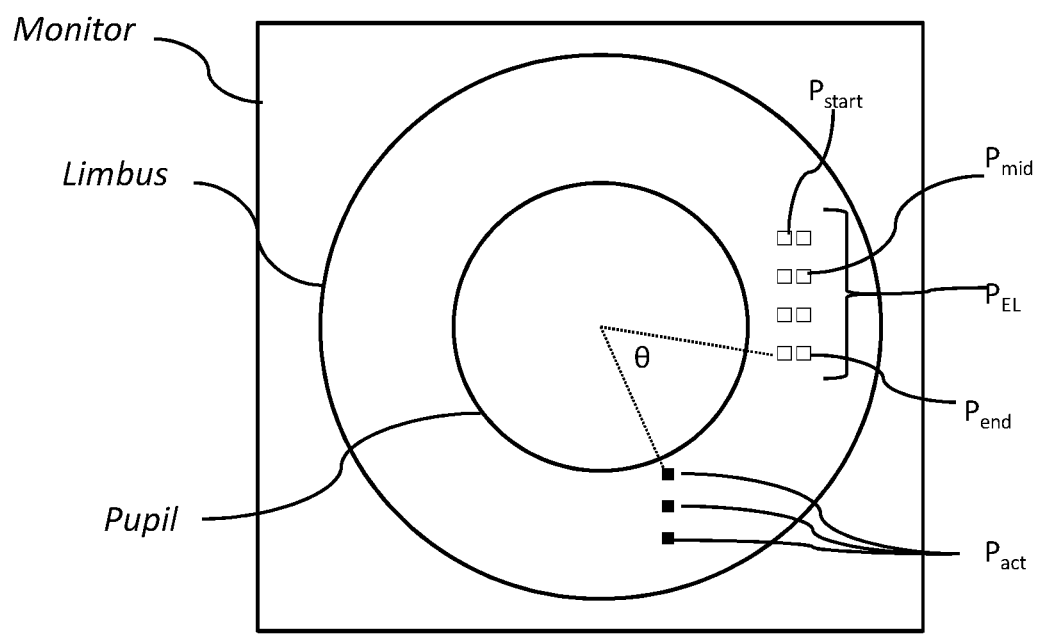
FIG. 5 illustrates an en face image of an eye.

The methods and/or acts of verifying the location of a laser scan within an object include, at Step 202 (FIG. 4), imaging the object, the resulting image including a portion of the object at a predetermined location to be scanned. The type or manner of imaging is not particularly limited, so long as the selected imaging method is capable of imaging the portion of the object in which the predetermined scan location is located. In many embodiments, the predetermined scan location includes the location of an incision that has been prescribed or identified by a health professional for placement in a tissue of the eye, such as the lens capsule, the lens, the cornea or the limbus. In this case, the selected imaging method should be capable of imaging the selected tissue. In one embodiment, the imaging method is optical imaging by a camera, and the image is presented as an en face image of the eye on monitor as shown in FIG. 5. The image may likewise be a video image in which successive images are captured in real time by a sensor and displayed on a monitor. The monitor may operate at, for instance, 60 Hz, 120 Hz or 240 Hz.

In another embodiment, the imaging method includes scanning the location of a focal point of a pulsed laser beam and confocally detecting light reflected from the location of the pulsed laser. Preferably, the pulsed laser beam is an ultraviolet pulsed laser beam having a wavelength of 320-370 nm. In many embodiments, the methods of verifying the location of a laser scan within an object include both video imaging and confocal imaging.

The methods and/or acts of verifying the location of a laser scan within an object include, at Step 204, identifying an expected scan location within the image corresponding to the predetermined scan location. In many embodiments, a camera 62 in the imaging system includes a sensor having an orthogonal array of pixels (e.g., in x and y directions where the corresponding z direction is in the direction of propagation of the electromagnetic radiation beam). Thus, in many embodiments, the image is comprised of an array of pixels, preferably color pixels. In many embodiments, a calibration of the system according to the methods described herein provides a known relationship between the location of a pixel in the orthogonal array of the image and a location of the tissue in the treatment space. This known correspondence between the pixels in the image and a location in treatment space makes it possible to identify an expected scan location in the image corresponding to the predetermined scan location. In many embodiments, the expected scan location within the image is a set of pixels, $P_{EL}$ illustrated visually in FIG. 5 (not to scale), that is a subset of the array of pixels comprising the image. The set of pixels, $P_{EL}$, may include a pixel denominated as an expected starting point pixel of the expected scan location, $P_{start}$, a pixel may be identified as an expected ending point pixel, $P_{end}$, of the expected scan location or a pixel denominated as a midpoint pixel, $P_{mid}$, located at some position between the starting point pixel and the ending point pixel.

The methods and/or acts of verifying the location of a laser scan within an object include, at Step 206, conducting a laser scan of the object by scanning a focal point of the laser beam through at least a portion of the object. The location of the scan is not particularly limited. But, in many embodiments, it will preferably include the predetermined scan location. The laser beam is preferably a pulsed laser beam, and preferably a pulsed ultraviolet laser beam. The laser scan is preferably a raster scan of the pulsed laser beam. In some embodiments, the laser beam may be of sufficient energy to modify the eye tissue scanned, and such that a succession of laser pulses within the eye tissue is sufficient to incise the tissue scanned. In other embodiments, the energy of the laser beam will be insufficient to modify the tissue scanned. The intensity of the laser beam is also preferably insufficient to cause the formation of a plasma, and also preferably insufficient to generate one or more cavitation events, such as the formation of a bubble.

The methods and/or acts of verifying the location of a laser scan within an object include, at Step 208, detecting the luminescence region scanned by the laser beam. As would be understood by those ordinarily skilled, individual photons of the ultraviolet laser beam, each having an energy, hv, will be absorbed by various components in the tissue scanned. This absorbed light will then be re-emitted by the component as a photon of lower energy (larger wavelength) either by fluorescence or phosphorescence from the scanned tissue. When ultraviolet light is used for the laser scan, the emitted luminescence generally includes light in the blue, indigo and violet portions of the visible spectrum, having wavelengths from about 400 nm to 475 nm. The emission of light from tissue, including by processes such as fluorescence or phosphorescence, is generally referred to herein as luminescence. In many embodiments, the luminescence, preferably in the range of 400 nm to 475 nm light is detected using the same camera 62 and same sensor having the orthogonal array of pixels which was used to image an object.

The methods and/or acts of verifying the location of a laser scan within an object include, at Step 208, detecting the luminescence from the region scanned by the laser beam. As would be understood by those ordinarily skilled, each pixel has red (R), Green (G) and Blue (B) components ("R, G, B components"), each having an intensity, I, associated with it that has a value from $I_{min}$ to $I_{max}$. In many embodiments, $I_{min}=0$ and $I_{max}=255$. According to some embodiments, the actual scanned location within the image may be determined monitoring the intensity, $I_B$, of the B component of the pixels that make up the image. In many embodiments, the actual scanned location may be comprised of one or more Pixels, $P_{act}$ in the image. In many embodiments, a pixel, $P_{act}$, is identified as being an actual scanned location if the measured value of $I_b$ for the pixel is greater than a predetermined threshold value, $I_p$. More than one $P_{act}$ may be identified in one image or frame. The predetermined threshold value may be empirically determined based on the object to be imaged. For instance, if the object to be imaged contains very few blue components, it may be possible to determine luminescence based on a relatively small $I_b$. In contrast, if the object to be imaged contains a relatively large amount of blue components, it may be necessary to determine luminescence based on a relatively large $I_B$. Those skilled in the art thus instructed can suitably determine the necessary threshold for each application. In some embodiments, the predetermined threshold value, $I_p$, may be $0.9I_{max}$, $0.8I_{max}$, $0.7I_{max}$, $0.6I_{max}$, $0.5I_{max}$, $0.4I_{max}$, $0.3I_{max}$, $0.2I_{max}$, or $0.1I_{max}$. This may be termed a "pixel thresholding" approach.

In other embodiments, the actual scanned location within the image may be determined by comparing the intensity, $I_B$, of the B component of a pixel in successive images or frames in an image. In this embodiment, the actual scanned location is determined by calculating a difference between an $I_b$ value of a pixel in a first frame, $I_{b1}$, and the $I_b$ value of the same pixel in a second successive frame, $I_{b2}$. In many embodiments, a pixel is identified as being an actual scanned location if the measured value difference, $I_{b2}-I_{b1}$ for a pixel is greater than a predetermined threshold value, $I_P$. The predetermined threshold value may be empirically determined based on the object to be imaged; however, since the identification is based on a difference in the same pixel in successive frames, the threshold may not be as sensitive to the amount of blue in the components of the image. In some embodiments, the predetermined threshold value, $I_p$, may be $0.9I_{max}$, $0.8I_{max}$, $0.7I_{max}$, $0.6I_{max}$, $0.5I_{max}$, $0.4I_{max}$, $0.3I_{max}$, $0.2I_{max}$, or $0.1I_{max}$. This may be termed a "consecutive differential" approach.

In other embodiments, the actual scanned location within the image may be determined by comparing an intensity, $I_B$, of the B component of a pixel in a first frame or image and then calculating a difference in intensity value for the pixel in each successive image or frame compared to its intensity of the first frame. In this embodiment, the actual scanned location is determined by comparing an $I_b$ value of a pixel in a first frame, $I_{b1}$, with the $I_b$ value of the same pixel in each successive i=2, n frames, i.e. $I_{b2}, I_{b3}, I_{b4} \ldots I_{bn \; etc.}$. In many embodiments, a pixel is identified as being an actual scanned location if the measured value difference, $I_{bi}-I_{b1}$ for a pixel is greater than a predetermined threshold value, $I_P$. The predetermined threshold value may be empirically determined based on the object to be imaged; however, since the identification is based on a difference in the same pixel in successive frames, the threshold may not be as sensitive to the amount of blue in the components of the image. In some embodiments, the predetermined threshold value, $I_p$, may be $0.9I_{max}$, $0.8I_{max}$, $0.7I_{max}$, $0.6I_{max}$, $0.5I_{max}$, $0.4I_{max}$, $0.3I_{max}$, $0.2I_{max}$, or $0.1I_{max}$. This may be termed an "absolute differential" approach.

In some embodiments, a statistical approach may be implemented for determining the actual scanned location within the image. In these probabilistic approaches, the values for the intensity, $I_B$ of the thresholding approach, the value of $I_{b2}-I_{b1}$ in the consecutive differential approach and the value $I_{bi}-I_{b1}$ in the absolute differential is assigned a probability of being an actual scanned location, and is determined to be an actual scanned location if the value of the probability is greater than a predetermined probability, for instance 50% (i.e., 0.5), or 60%, 70%, 80% or 90%.

Since a scan is conducted over a period of time, the pixels which are identified as being an actual scanned location, $P_{act}$, may change during the time course of the scan. Analysis, such as by overlaying successive frames or obtaining difference images between frames, either of individual pairs of frames or of all successive images/frames during the scan permits the determination of all the actual scanned locations and of the direction of the scan during the scan. In some embodiments, all actual scanned locations may be determined before a comparison of the actual scanned location with the expected scan location is completed.

The methods and/or acts of verifying the location of a laser scan within an object include, at Step 214, providing a warning if a difference between the actual location in the image and an expected scan location in the image is greater than a threshold distance, $D_T$. The nature of the warning is not particularly limited. For instance, a warning message may be placed on the image indicating a difference in the expected scan location and actual scan location has been detected. The warning may optionally include stopping the scan and alerting a user. Where the object is an eye, the warning may also optionally include reducing the intensity of the laser beam below a level necessary to incise the tissue.

The manner of calculating the difference between the expected scan location and the actual scan location is not particularly limited. In many embodiments, the calculated difference may be a distance between the expected scan location and the actual scanned location. The distance may be between any of the one or more pixels, $P_{act}$, identified as an actual scan location and any pixel from the set of pixels, $P_{EL}$, that comprises the expected scan locations. In some embodiments, one $P_{act}$ from the actual scan locations is selected for the distance measurement and one pixel is selected from the set of $P_{EL}$ pixels for the distance measurements. In some embodiments, the selected expected scan location pixel may be either $P_{start}$, $P_{end}$ or a $P_{mid}$. The distance may be calculated as a number of pixels separating the selected pixels. Alternatively, the distance may be calculated as a physical distance in, for instance, units of microns. In another alternative, it may be suitable to calculate the distance as an angular distance between the pixels, for instance, by an angle theta, $\theta$, around an axis centered at the pupil center in the direction of propagation of the laser light source. The threshold difference, $D_T$, may be chosen based on the units selected. In the case of a distance measured in microns, the threshold difference $D_T$, may be 5000 microns, or 1000 microns, or 500 microns or 200 microns or 100 microns, or 50 microns or 5 microns. In the case of angular distance, the distance $D_T$, may be 120°, or 90°, or 60°, or 45°, or 30°, or 15°.

The methods and/or acts of verifying the location of a laser scan may be used in connection with laser eye surgery systems and methods to verify the placement of one or more ocular incisions, including in methods for cataract surgery using a laser eye surgery system for verifying the placement of incisions in a cataract surgery. The laser eye surgery system may be the one shown in FIGS. 1-3 and described herein. Thus, some embodiments are a laser surgical system configured to carry out the methods described herein. In some embodiments, a user or physician will define one or more incisions to be performed by the laser surgical system during cataract surgery selected from capsulotomy incisions, primary incisions, sideport incisions and arcuate incisions by entering the necessary parameters into system to define the incision. The laser surgical system is configured to receive those parameters, image the eye, identify the expected scan location within the image corresponding to the selected incisions, conduct a laser scan of the eye by scanning the focal point of a laser beam, detect luminescence from the region scanned, identify the actual scanned location within the image based on the detected luminescence, and provide a warning to the user if the difference between the expect location in the image and the actual location in the image is greater than a predetermined threshold. In some embodiments, the laser scan that is conducted is a confocal imaging scan of the eye to verify that the confocal imaging scan is imaging the actual location to be incised. In some embodiment, the laser scan conducted is a treatment scan of sufficient energy to incise the tissue to be treated. In other embodiments, the scan conducted is the same as the treatment scan but at energies insufficient to incise human tissue. This scan can be done in order to verify the placement of the incisions prior to conducting a treatment scan capable of incising tissue.

Figure 6A:
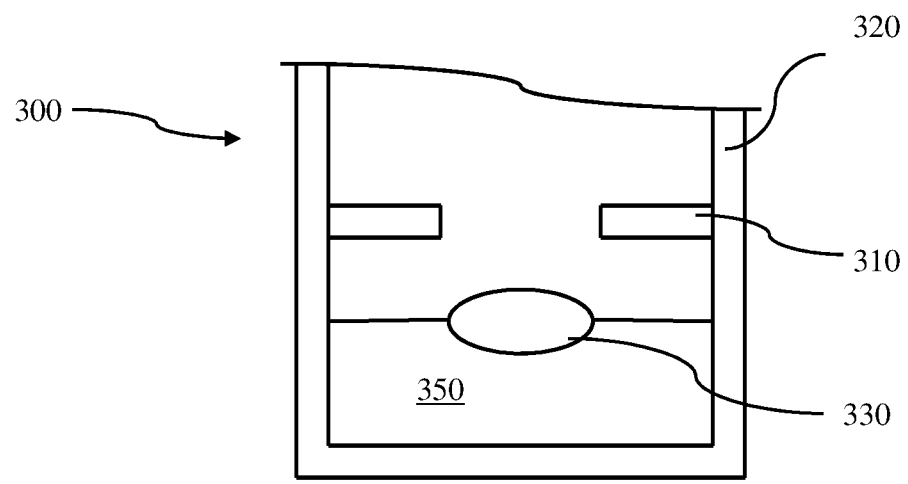
FIGS. 6A and 6B illustrate a calibration apparatus.
Figure 6B:
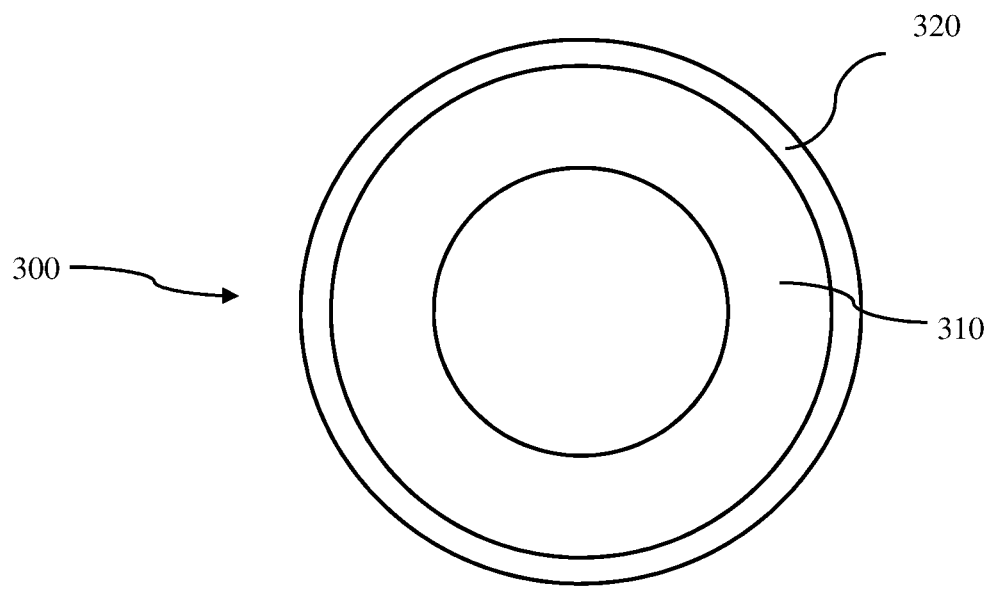

The methods and/or acts of verifying the location of a laser scan may be used in connection with laser eye surgery systems and methods to verify the calibration of an eye surgical system prior to treatment. The methods or acts of verifying the calibration may include a calibration apparatus 300 shown in FIGS. 6A and 6B. The calibration apparatus 300 includes sidewall 320 and also comprises structures similar to structures of an eye. For example, the calibration apparatus 300 may include a container 350 having a viscous substance or solid substance that is similarly optically transmissive to the structures of the eye. The material 350 may comprise of visco-elastic fluid, a gel or other optically transmissive structure and material, for example. The calibration apparatus 300 comprises an iris structure 310 and, optionally, a lens structure 330, either of which can provide a suitable surface for calibration. At least one of the surfaces of lens structure 330 or iris structure 310 should emit blue wavelength light when irradiated by ultraviolet light. Here, a structure or property is "similar" if it is within 10%, preferably within 5% and more preferably within about 1% of a typical measurement of that structure or property in an adult human eye. The calibration structure 300 may connect to the patient interface as described herein and a fluid (note shown) can be provided above the calibration apparatus, for example.

A method and/or acts of verifying the calibration of laser surgical system, including a laser eye surgical system, include imaging a calibration apparatus, identifying an expected scan location within the image corresponding to a predetermined scan pattern within the calibration apparatus, conducting a laser scan of the calibration apparatus by scanning the focal point of a laser beam, detecting luminescence from the region of the calibration area scanned, identifying the actual scanned location within the image based on the detected luminescence, and identifying the laser surgical system as not calibrated if a difference between the expected scan location in the image and the actual location in the image is greater than a predetermined threshold. The method can also include identifying the laser surgical system as calibrated if a difference between the expected scan location in the image and the actual location in the image is less than a predetermined threshold.

System Calibration

In many embodiments, a calibration of the system is carried out to provide a known relationship between the location of a pixel in the orthogonal array of the image and a location of the tissue in the treatment space. This known correspondence between the pixels in the image and a location in treatment space makes it possible to identify an expected scan location in the image corresponding to the predetermined scan location, an actual scanned location of a laser scan in the image and a difference between the actual scanned location and the expected scan location. The method for performing the calibration is not particularly limited. Examples of suitable calibration methods can be found, for instance, in U.S. Publication No. U.S. 2014-0128853 A1 (U.S. patent application. Ser. No. 14/069,703, filed Nov. 1, 2013, entitled "Laser Surgery System Calibration") and U.S. Publication No. 2014-0316389 A1 (U.S. patent application Ser. No. 14/191,095, filed Feb. 26, 2014, entitled "Laser Eye Surgery System"), the entire contents of which are hereby incorporated by reference herein in their entirety.

In brief, the laser surgery system 10 can be calibrated to relate locations in a treatment space with pixels in the camera 62 and with control parameters used to control the scanning assembly 18 such that the focal point of the electromagnetic radiation beam can be accurately positioned within the intraocular target. Such calibration can be accomplished at any suitable time, for example, prior to using the laser surgery system 10 to treat a patient's eye.

FIG. 7A is a top view diagram of a calibration plate 402 that can be used to calibrate the laser surgery system 10. In many embodiments, the calibration plate 402 is a thin plate having an array of target features, for example, through holes 404 therein. In alternate embodiments, the calibration plate 402 is a thin plate having a field of small dots as the target features. While any suitable arrangement of the target features can be used, the calibration plate 402 of FIG. 7A has an orthogonal array of through holes 404. Any suitable number of the target features can be included in the calibration plate 402. For example, the illustrated embodiment has 29 rows and 29 columns of the through holes 404, with three through holes at each of the four corners of the calibration plate 402 being omitted from the orthogonal array of through holes 404.

In many embodiments, each of the through holes 404 is sized small enough to block a suitable portion of an electromagnetic radiation beam when the focal point of the electromagnetic radiation beam is not located at the through hole. For example, each of the through holes 404 can have a diameter slightly greater than the diameter of the focal point of the electromagnetic radiation beam so as to not block any of the electromagnetic radiation beam when the focal point is positioned at one of the through holes 404. In the embodiment shown, the through holes 404 have a diameter of 5 µm, which is sized to be used in conjunction with a focal point diameter of 1 µm.

FIG. 7B schematically illustrates using the calibration plate 402 to calibrate the camera 62 of the laser surgery system 10. The calibration plate 402 is supported at a known fixed location relative to the objective lens assembly 20. In many embodiments, the objective lens assembly 20 is configured for telecentric scanning of the electromagnetic radiation beam and the calibration plate 402 is supported to be perpendicular to the direction of propagation of the electromagnetic radiation beam. The calibration plate 402 is disposed between the objective lens assembly 20 and a light source 406. The light source 406 is used to illuminate the calibration plate 402. A portion of the illumination light from the light source 406 passes through each of the through holes 404, thereby producing an illuminated location within the field of view of the camera 62 at each of the through holes 404. A light beam 408 from each of the through holes 404 passes through the objective lens assembly 20, through the video dichroic 66, an into the camera 62. In many embodiments, the camera 62 includes a sensor having an orthogonal array of pixels (e.g., in x and y directions where the corresponding z direction is in the direction of propagation of the electromagnetic radiation beam). In many embodiments, X and Y pixel values for each of the light beams 408 is used in conjunction with the known locations of the through holes 404 relative to the objective lens assembly 20 to determine the relationship between the camera X and Y pixel values and locations in the treatment space for dimensions transverse to the propagation direction of the electromagnetic radiation beam.

FIG. 7C schematically illustrates using the calibration plate 402 to calibrate the scanning assembly 18. The calibration plate 402 is supported at a known fixed location relative to the objective lens assembly 20. In many embodiments, the objective lens assembly 20 is configured for telecentric scanning of the electromagnetic radiation beam and the calibration plate 402 is supported to be perpendicular to the direction of propagation of the electromagnetic radiation beam. The calibration plate 402 is disposed between the objective lens assembly 20 and a detector 410. The detector 410 is configured to generate a signal indicative of how much of the electromagnetic radiation beam is incident thereon, thereby being indirectly indicative of how much of the electromagnetic radiation beam is blocked by the calibration plate 402. For example, when the focal point of the electromagnetic radiation beam is positioned at one of the through holes 404 (as illustrated for the focal point disposed on the right side of the detection plate 402 in FIG. 7B), a maximum amount of the electromagnetic radiation beam passes through the through hole and is incident on the detector 410. In contrast, when the focal point of the electromagnetic radiation beam is not positioned at one of the through holes 404 (as illustrated for the focal point disposed above the left side of the detection plate 402 in, a portion of the electromagnetic radiation beam is blocked from reaching the detector 410.

Control parameters for the z-scan device 58 and the xy-scan device 60 are varied to locate the focal point of the electromagnetic radiation beam at each of a suitable set of the through holes, thereby providing data used to determine the relationship between the control parameters for the scanning assembly 18 and the resulting location of the focal point of the electromagnetic radiation beam. The z-scan device 58 is operable to vary a convergence/divergence angle of the electromagnetic radiation beam, thereby being operable to control the distance of the focal point from the objective lens in the direction of propagation of the electromagnetic radiation beam. The xy-scan device 60 is operable to vary a direction of the electromagnetic radiation beam in two dimensions, thereby providing the ability to move the focal point in two dimensions transverse to the direction of propagation of the electromagnetic radiation beam.

A suitable existing search algorithm can be employed to vary the control parameters for the z-scan device 58 and the xy-scan device 60 so as to reposition the focal point to be located at each of a suitable set of the through holes 404. In many embodiments where the objective lens assembly 20 is configured to telecentrically scan the electromagnetic radiation beam, the resulting control parameter data for the scanning assembly 18 can be used to calibrate the scanning assembly 18 relative to directions transverse to the direction of propagation of the electromagnetic radiation beam (e.g., x and y directions transverse to a z direction of propagation of the electromagnetic radiation beam).

Application to Cataract Surgery

In many embodiments, the methods and/or acts of verifying the location of a laser scan is used with laser eye surgery systems and methods to verify the placement of one or more ocular incisions. In many embodiments, the methods and/or acts are used in cataract surgery using a laser eye surgery system for verifying the placement of incisions in a cataract surgery.

In cataract surgery, a capsulotomy incision, often in the form of a small round hole is formed in the anterior side of the lens capsule to provide access to the lens nucleus.

In addition, cataract surgery may include three types of cornea incisions: arcuate, primary, and sideports. Parameters that may be used to define the capsulotomy include shape (i.e. circular, elliptical, rectangular or polygonal) and size. The systems described herein are designed to receive these parameters based on user or physician's input and preferably, to provide a prompt for their input where not received.

Primary incisions and sideport incisions may have the same structure. They are generally multiplanar structures that create an opening that allow the physician access into the anterior chamber. The primaries are used for insertion of the aspiration tool and the insertion of the IOL. Sideport incisions may be used for inserting smaller instrumentation into the anterior chamber. The location and shape of both the primary incisions and the sideport incisions are determined by the user parameters and, optionally, by information from a section scan as described herein, where the cornea anterior and posterior surfaces may be modeled by circles. The anterior and posterior curvatures of the cornea as measured in the circular fits of the section scans may optionally be used to position the cuts. Parameters that may be used to define the primary cataract incision or the sideport incision are preferably selected from the group consisting of limbus offset, width, side cut angle, plane depth, and length. The systems described herein are designed to receive these parameters based on user or physician's input and preferably, to provide a prompt for their input where not received.

Arcuate incisions may be used to correct a patient's astigmatism. For instance, they may adjust the curvature of the cornea to a more spherical shape by means relaxing stresses along the meridian on which they are placed. They are parts of a conical surface that crosses both the anterior and posterior surfaces of the cornea. In some embodiments, the anterior curvature and posterior curvature of the cornea, as measured in a circular fit to a section scan, are used to position an "along-the-cut" scan. The along-the-cut scan lays on the surface of a cone that transverses the cornea. The arcuate incision can be located within the along-the-cut scan. Parameter that may be used to define the arcuate incision may include the size of the optical zone, arc length, uncut anterior portion, uncut posterior portion and side cut angle. The systems described herein are designed to receive these parameters based on user or physician's input and preferably, to provide a prompt for their input where not received.

Capsulotomy Incisions

The laser surgery system 10 can be used to form any suitably shaped capsulotomy. For example, while the anterior and posterior capsulotomies in the illustrated embodiments are circular, any other suitable shape, including but not limited to, elliptical, rectangular, and polygonal can be formed. And the anterior and/or posterior capsulotomy can be shaped to accommodate any correspondingly suitably shaped IOL.

Figure 8:
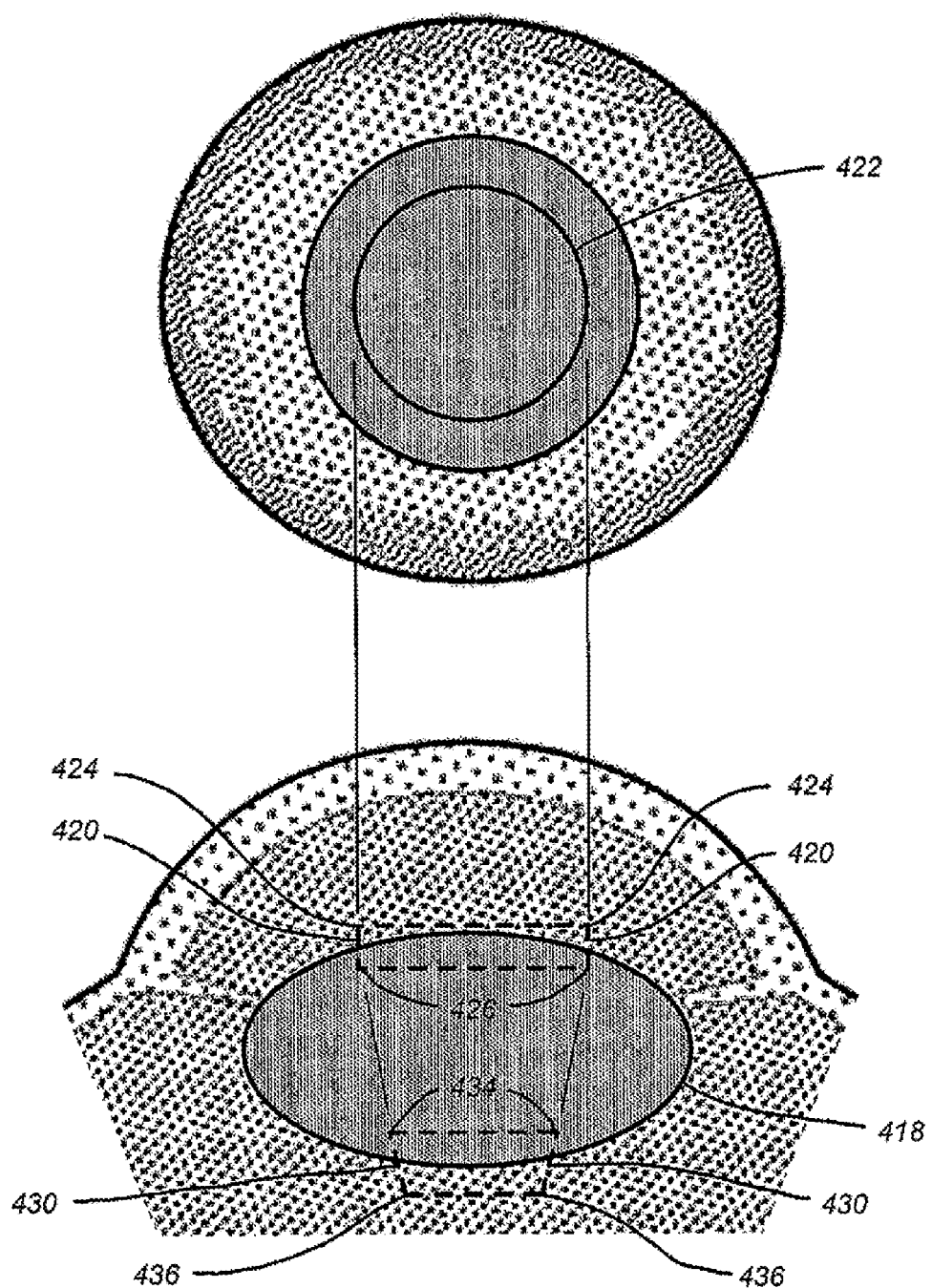
FIG. 8 shows a plan view of a capsulotomy incision locator and a cross-sectional view showing projection of the capsulotomy incision locator on the lens anterior capsule, according to many embodiments.

For example, referring now to FIG. 8, the laser surgery system 10 can be used to incise an anterior capsulotomy and/or a posterior capsulotomy in the anterior portion of a lens capsule 418. The focal point of the electromagnetic radiation beam can be scanned to form an anterior capsulotomy closed incision boundary surface 420 that transects the anterior portion of the lens capsule 418. Likewise, the focal point of the electromagnetic radiation beam can be scanned to form a posterior capsulotomy closed incision boundary surface 430 that transects the posterior portion of the lens capsule 418.

The anterior and/or posterior closed incision boundary surfaces 420, 430 can be designated using any suitable approach. For example, a plan view of the patient's eye can be obtained using the camera 62. A capsulotomy incision designator 422 can be located and shown superimposed on the plan view of the patient's eye to illustrate the size, location, and shape of a planned capsulotomy relative to the patient's eye. The capsulotomy incision designator 422 can be manually defined by an operator of the laser surgery system 10 and/or the laser surgery system 10 can be configured to generate an initial capsulotomy incision designator 422 for operator verification and/or modification.

The anterior capsulotomy closed incision boundary surface 420 can be defined on a projection of the capsulotomy incision designator 422 such that the anterior capsulotomy closed incision boundary surface 420 transects the anterior portion of the lens capsule 418 at all locations around the anterior capsulotomy incision boundary surface 420 for all expected variations in the location of the anterior portion of the lens capsule 418 relative to the projection of the capsulotomy incision designator 422. For example, a curve corresponding to the capsulotomy incision designator 422 can be projected to define an intersection with a minimum depth mathematical surface model (e.g., a spherical surface) defining a minimum expected depth configuration for the anterior portion of the lens capsule 418 with the resulting intersection being an anterior capsulotomy upper closed curve 424 that defines an upper boundary for the anterior capsulotomy closed incision boundary surface 420. Likewise, the curve corresponding to the capsulotomy incision designator 422 can be projected to define an intersection with a maximum depth mathematical surface model (e.g., a spherical surface) defining a maximum expected depth configuration for the anterior portion of the lens capsule 418 with the resulting intersection being an anterior capsulotomy lower closed curve 426 that defines a lower boundary for the anterior capsulotomy closed incision boundary surface 420. Alternatively, the focal point can be scanned using a low imaging-only power level (e.g., a power level sufficient to provide for imaging of the intraocular target via processing of the signal generated by the detection sensor 54 of the confocal detection assembly 14 without modifying the intraocular target) along the projection of the capsulotomy incision designator 422 while varying the depth of the focal point to determine the depth of the anterior lens capsule at a sufficient number of locations around the projection of the capsulotomy incision designator 422. The measured depths of the anterior lens capsule can then be used to determine suitable anterior capsulotomy upper and lower boundary curves 424, 426 of the anterior capsulotomy closed incision boundary surface 420.

Corneal Incisions

The laser surgery system 10 can be used to form any suitably shaped arcuate, primary or sideport incisions.

Figure 9A:
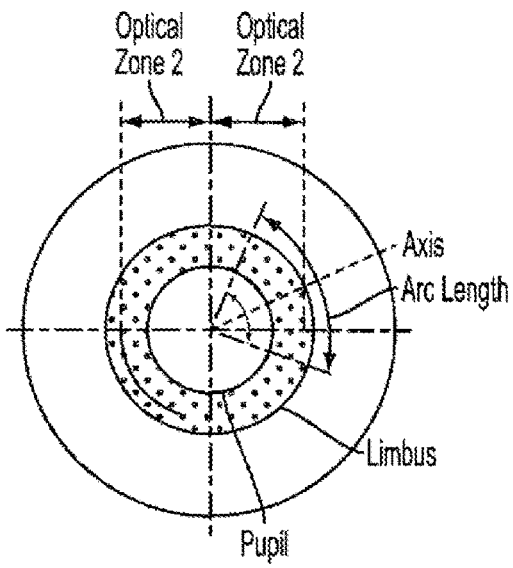
FIGS. 9A, 9B and 9C illustrate aspects of arcuate incisions of a cornea that can be formed by the laser surgery system of FIG. 1, according to many embodiments.
Figure 9B:
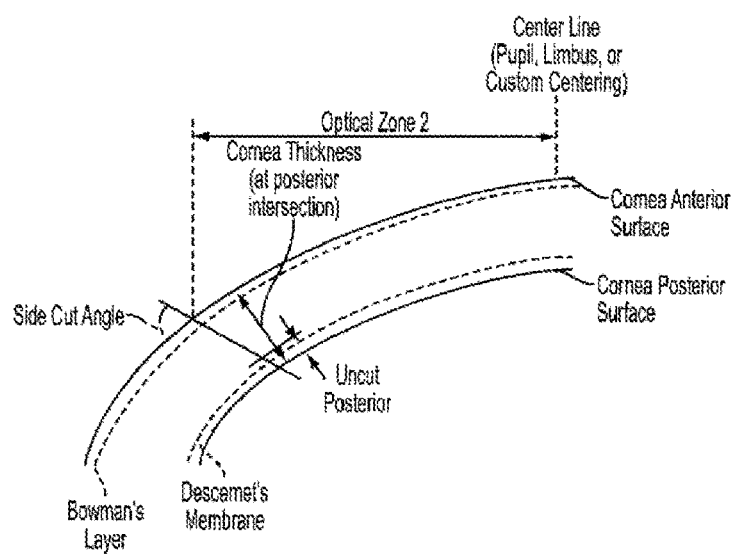
Figure 9C:
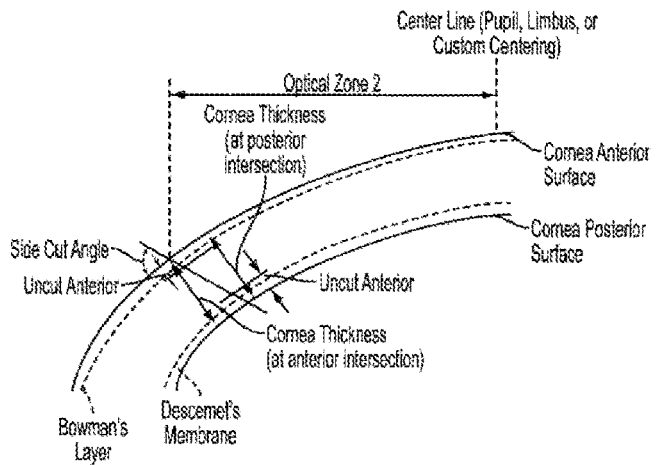

FIGS. 9A through 9C illustrate aspects of arcuate incisions of a cornea that can be formed by the laser surgery system 10, according to many embodiments. FIG. 9A shows an en face view of arcuate incisions within the optical zone of the cornea that can be formed using the laser surgery system 10. The optical zone can be user-adjustable within, for example, the range of 2 mm-11 mm. For asymmetric arcuate incisions, the optical zone can be independently adjustable for each incision. Arc length can be user-adjustable within, for example, the range of 10°-120°.

FIG. 9B shows a cross-sectional view of an arcuate incision in the cornea that can be formed using the laser surgery system 10 and that penetrates the cornea anterior surface and has an uncut posterior portion. FIG. 9C shows a cross-sectional view of an arcuate intrastromal incision in the cornea that can be formed using the laser surgery system 10. The arcuate intrastromal incision has an uncut anterior portion and an uncut posterior portion. Side cut angle can be user-adjustable within, for example, the range of 30°-150°. Uncut posterior and anterior portions can be user-adjustable within, for example, the range of 100 µm-250 µm or 20%-50% of the cornea thickness. Cornea thickness can be measured at the projected intersection of the incision with the cornea anterior/posterior measured at 90° to anterior/posterior cornea surface regardless of what side cut angle is chosen.

Figure 10A:
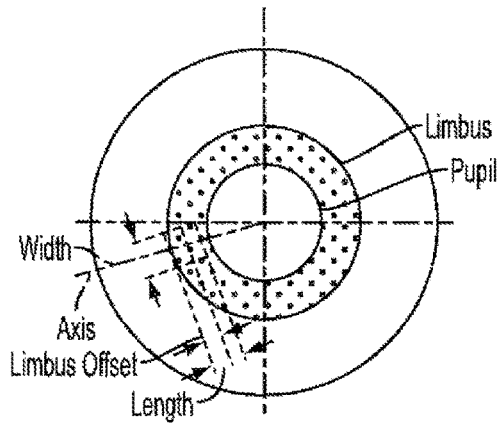
FIGS. 10A, 10B, 10C, 10D, 10E and 10F illustrate aspects of primary cataract surgery access incisions of a cornea that can be formed by the laser surgery system of FIG. 1, according to many embodiments.
Figure 10B:
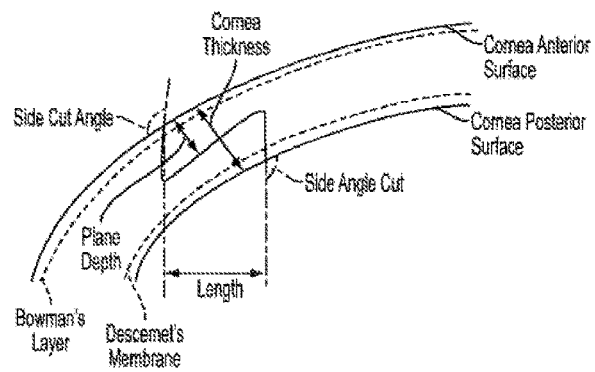
Figure 10C:
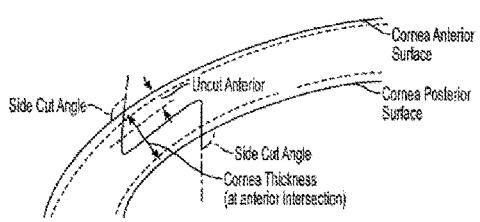
Figure 10D:
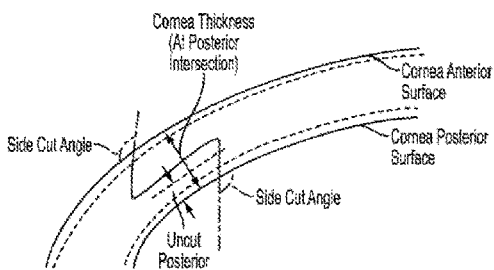
Figure 10E:
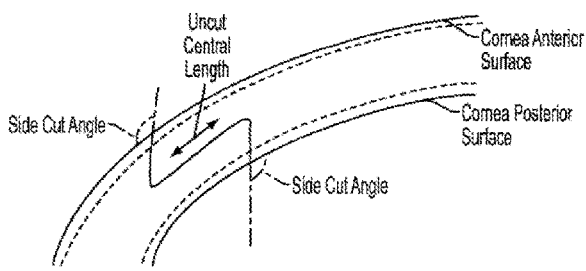
Figure 10F:
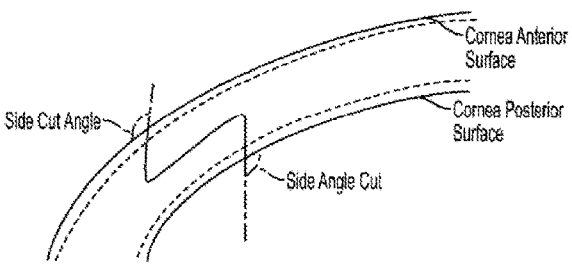

FIG. 10A shows an en face view of a primary cataract incision in the cornea that can be formed using the laser surgery system 10. The primary cataract incision provides access to surgical tools used to, for example, remove a fragmented crystalline lens nucleus and insert in an IOL. FIG. 10B shows a cross-sectional view of a primary cataract incision of the cornea that can be formed using the laser surgery system 10. Limbus offset can be user-adjustable within, for example, the range of 0.0 mm-5.0 mm. Width can be user-adjustable within, for example, the range 0.2 mm-6.5 mm. Length can be user-adjustable within, for example, the range of 0.5 mm-3.0 mm. Side Cut Angle can be user-adjustable within, for example, the range of 30°-150°. Plane depth can be user-adjustable within, for example, the range of 125 µm-375 µm or 25%-75% of the cornea thickness. Length can be defined as the en face view distance between the projected incision intersection with the cornea anterior and the cornea posterior. FIG. 10C shows a cross-sectional view of a primary cataract incision that includes an uncut anterior portion. FIG. 10D shows a cross-sectional view of a primary cataract incision that includes an uncut posterior portion. FIG. 10E shows a cross-sectional view of a primary cataract incision that includes an uncut central length. And FIG. 10F shows a cross-sectional view of a primary cataract incision that includes no uncut portion. Side Cut Angle can be user-adjustable within, for example, the range of 30°-150°. Uncut central length can be user-adjustable within, for example, the range of 25 µm-1000 µm.

Figure 11A:
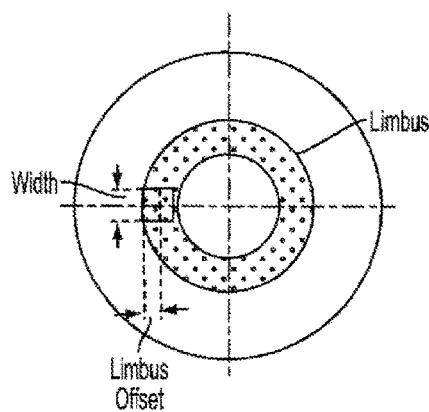
FIGS. 11A, 11B, 11C, 11D and 11E illustrate aspects of sideport cataract surgery access incisions of a cornea that can be formed by the laser surgery system of FIG. 1, according to many embodiments.
Figure 11B:
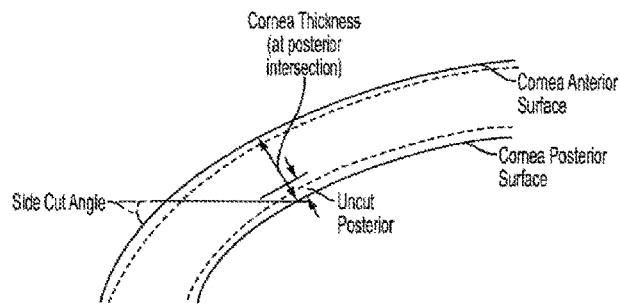
Figure 11C:
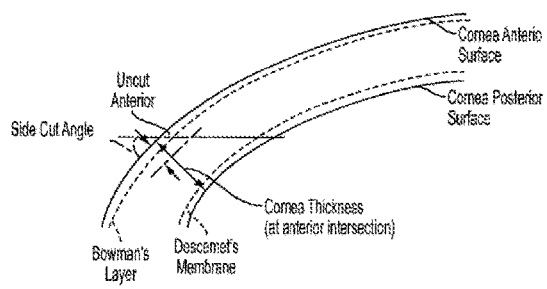
Figure 11D:
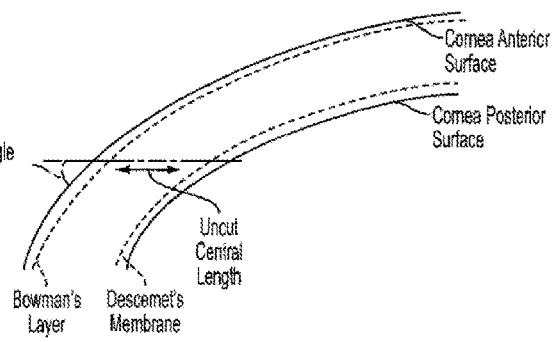
Figure 11E:
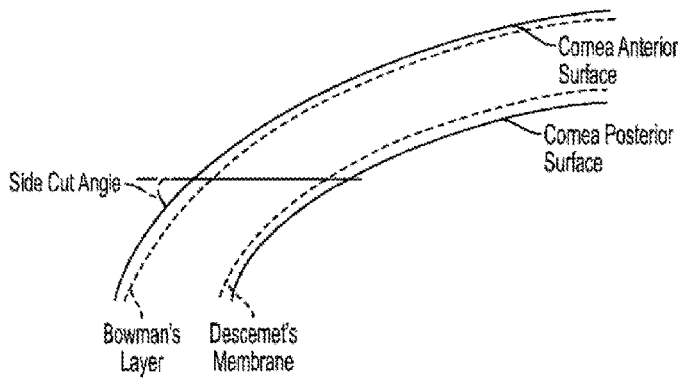

FIG. 11A shows an en face view of a sideport cataract incision in the cornea that can be formed using the laser surgery system 10. The sideport cataract incision provides access for surgical tools used, for example, to assist in the removal of a fragmented crystalline lens. FIG. 11B shows a cross-sectional view of a sideport cataract incision of the cornea that has an uncut posterior portion and can be formed using the laser surgery system 10. Limbus offset can be user-adjustable within, for example, the range of 0.0 mm-5.0 mm. Width can be user-adjustable within, for example, the range 0.2 mm-6.5 mm. Length can be user-adjustable within, for example, the range of 0.5 mm-3.0 mm. FIG. 11C shows a cross-sectional view of a sideport cataract incision that includes an uncut anterior portion. FIG. 11D shows a cross-sectional view of a sideport cataract incision that includes an uncut central length. And FIG. 11E shows a cross-sectional view of a sideport cataract incision that includes no uncut portion. Side Cut Angle can be user-adjustable within, for example, the range of 30°-150°. Uncut central length can be user-adjustable within, for example, the range of 100 µm-250 µm or 20%-50% of the cornea thickness. Cornea thickness can be measured at the projected intersection location of the incision with the cornea anterior/posterior measured at 90° to the anterior/posterior cornea surface regardless of what side cut angle is chosen.

Video and Confocal Imaging of Incision Locations

Although many different imaging techniques may be used in different embodiments, a combination of video/camera imaging and confocal imaging based on pulsed laser raster scanning of the tissue to be treated is preferred.

Figure 13:
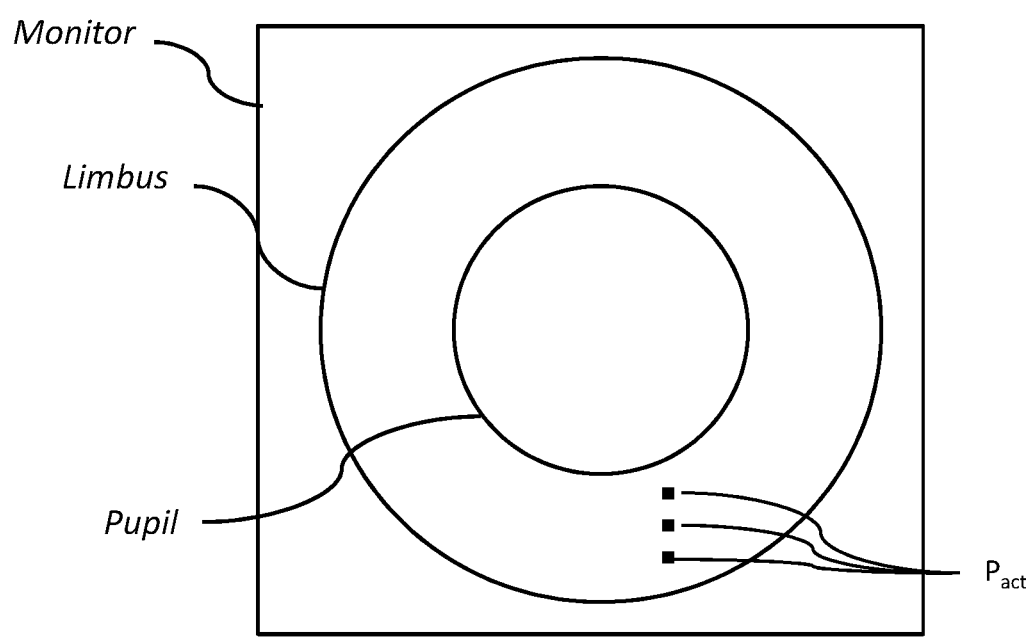
FIG. 13 is a schematic diagram illustrating an en face image of the eye projected onto a monitor using a laser surgery system such as described in FIG. 1.

As illustrated in the embodiment of FIG. 1, video imaging of the tissue to be treated, preferably a human eye, can be achieved by a camera 62 and associated video illumination 64 integrated with the scanning assembly 18. The camera 62 and the beam 28 share a common optical path through the objective lens assembly 20 to the eye. A video dichroic 66 is used to combine/separate the beam 28 with/from the illumination wavelengths used by the camera. In one embodiment, the beam 28 can have a wavelength of between 320 and 370 nm, preferably about 355 nm, and the video illumination 64 can be configured to emit illumination having wavelengths greater than 370 nm, or more than 400 or more than 450 nm. Accordingly, the video dichroic 66 can be configured to reflect the beam between 320 and 370 nm wavelength while transmitting wavelengths greater than 370 nm, thus facilitating video imaging of the eye without interference from beam 28. The resulting video image is preferably an en face image as shown in FIG. 13. The location(s) of the capsulotomy incision and any corneal incision specified by the physician can be projected onto the video image prior to treatment as expected scan locations for each respective incision.

In many embodiments, the imaging of the eye 24 further includes confocally imaging one or more portions of the tissue, preferably the eye, to be treated. Any suitable device, assembly, and/or system, such as described herein, can be used to confocally image one or more portions of the eye or other tissue to be imaged. The confocal imaging methods used herein generally include using a beam source, preferably a pulsed laser source, to generate an electromagnetic radiation beam; propagating the electromagnetic radiation beam to a scanner along an optical path to the eye; focusing the electromagnetic radiation beam to a focal point at a location within the eye; using the scanner to scan, preferably raster scan, the focal point to different locations within the eye; propagating a portion of the electromagnetic radiation beam reflected from the focal point location back along the shared optical path to a sensor; and generating an intensity signal indicative of the intensity of a portion of the electromagnetic radiation beam reflected from the focal point location and propagated to the sensor. The method can include modifying polarization of at least one of the electromagnetic radiation beam and a portion of the electromagnetic radiation beam reflected from the focal point location. The method can include using the polarization-sensitive device to reflect a portion of the electromagnetic radiation beam reflected from the focal point location so as to be incident upon the sensor.

Based on the calibration of the system described herein, the focal point location of the confocally detected light can be related to the physical location of the focal point within the eye, and the location within the eye and the magnitude of the intensity at each location can be used to identify boundaries, edges and layers within the eye. Boundaries, edges and layers may be located in a confocal image by, for instance, Delaunay triangulation and Dijkstra segmentation. These confocal images, including the boundaries, edges and layers can then be displayed to a user as a graphical representation of the areas of the eye to be treated.

In many embodiments, the lens capsule, and optionally a portion or all of the lens, are imaged using confocal imaging, and preferably, these portions include the area of the lens capsule where the capsulotomy will be placed. In general, the parameters necessary to define the capsulotomy are input by a user or physician, and a raster scan with a pulsed laser beam sweeps through the relevant portion of the lens capsule for imaging the lens capsule. Based on the recorded location and magnitude of the confocally reflected intensity measurements at each location, the capsule is identified by image recognition, such as by Delaunay triangulation and Dijkstra segmentation, and the capsule shape is fit to the segmented image. The resulting confocal image of lens may then be shown to the physician for use in visualizing the capsulotomy incision.

Figure 14:
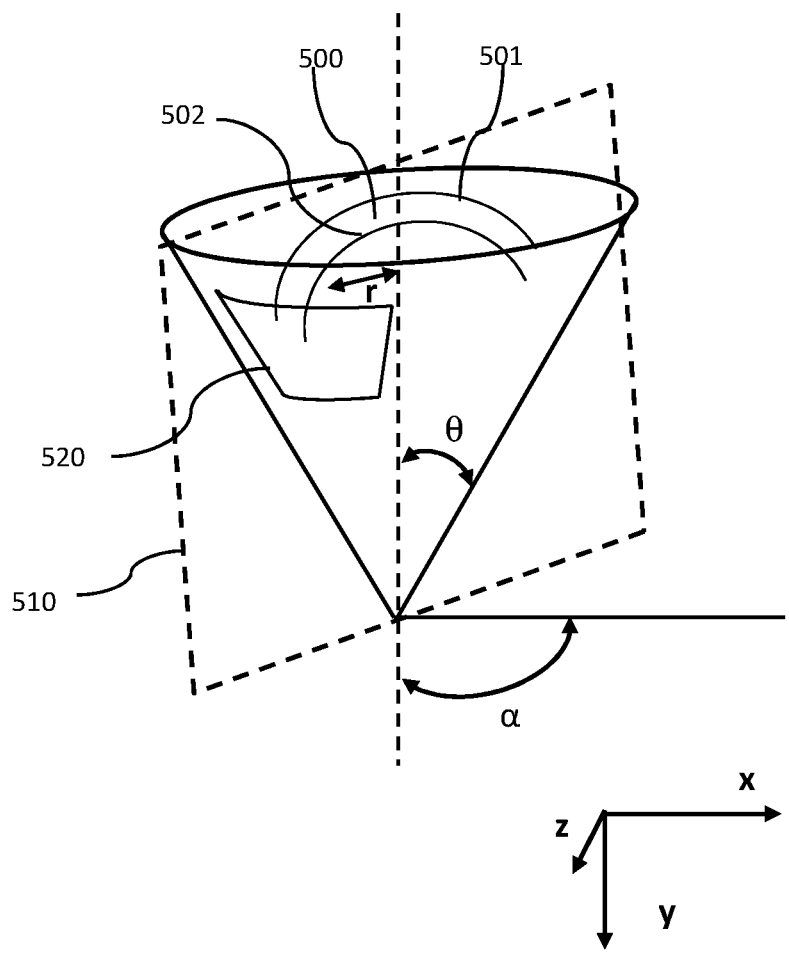
FIG. 14 is a schematic diagram of aspects of a section scan and an along-the-cut scan for imaging areas of a cornea.

In many embodiments, the methods and systems may include confocally imaging a cornea by scanning one or more of portions of the cornea where a primary incision, sideport incision or arcuate incision is to be placed. In a preferred embodiment, one sectional image of the cornea is performed for each selected corneal incision. These images are preferably in the form of a section scan. As shown in FIG. 14, a section scan crosses cornea 500 along plane 510 and measures the confocal intensity at every location of a pulsed laser during the scan. Preferably, a section scan 510 comprises a raster scan of a pulsed laser beam along the cornea 500, including the anterior surface 501 and posterior surface 502, on a vertical plane 510 centered at the cornea incision center and oriented along an incision's meridian. The trajectory goes from deep to shallow, inside the eye, crossing the cornea. The posterior and anterior boundaries of the cornea may be identified in the image by, for instance, Dijkstra segmentation of the image, and the resulting image may be provided to the user.

If the selected corneal incision is an arcuate incision, an "along-the-cut" imaging scan is also preferably performed. An along-the-cut imaging scan may assist a physician in choosing the correct location for the arcuate incision in order to maintain an adequate depth and avoid posterior penetration. The "along the cut" scan preferably has the same conical shape as the arcuate incision and is inclusive of the entire area to be covered arcuate incision. The conical sector in the "along the cut" scan is mapped into a rectangular domain 520 defined by the conical coordinates. The resulting conical image is segmented and fit. Optionally, the resulting fits to the anterior and posterior surfaces of the cornea are used to construct the arcs, which can then be overlaid on their sections and "along the cut" scans.

In many embodiments, the optical surface of the eye is fit with one or more with one or more of a Fourier transform, polynomials, a spherical harmonics, Taylor polynomials, a wavelet transform, or Zernike polynomials. The optical tissue surface may comprise one or more of the anterior surface of the cornea, the posterior surface of the cornea, the anterior surface of the lens capsule, the posterior surface of the lens capsule, an anterior surface of the lens cortex, a posterior surface of the lens cortex, an anterior surface of the lens nucleus, a posterior surface of the lens nucleus, one or more anterior surfaces of the lens having a substantially constant index of refraction, one or more posterior surfaces of the lens having a substantially constant index of refraction, the retinal surface, the foveal surface, a target tissue surface to correct vision such as a target corneal surface, an anterior surface of an intraocular lens, or a posterior surface of an intraocular lens, for example.

Generating a Treatment Scan

After the relevant portions of the lens, lens capsule and cornea have been imaged, the incisions defined by the physician parameters may be projected onto the image, and a treatment scan of the laser light beam is generated. The treatment scan preferably consists of a continuous set of x, y, z points arranged in space that are designed to carry out the incisions defined by the user. The location of the treatment scans are projected onto at least one of the video and confocal images in order to define the set of expected scan locations of the incisions.

Detecting an Actual Location of a Scan by Luminescence

Certain components of eye tissue absorb light having wavelengths of 370 nm and less and emit red-shifted light (due for instance, to either fluorescence or phosphorescence) at wavelengths greater than 370 nm. The emitted light from the eye tissue is also passed by dichroic 66 in FIG. 12. Thus, when the focal point of beam 28 is scanned across the tissue to be treated, the location of the focal point of beam 28 within the target tissue can be tracked by camera 62 based on the known relationship between the pixels of the camera 62 and the location of the focal point in the treatment space as established by the calibration described above.

Figure 12:
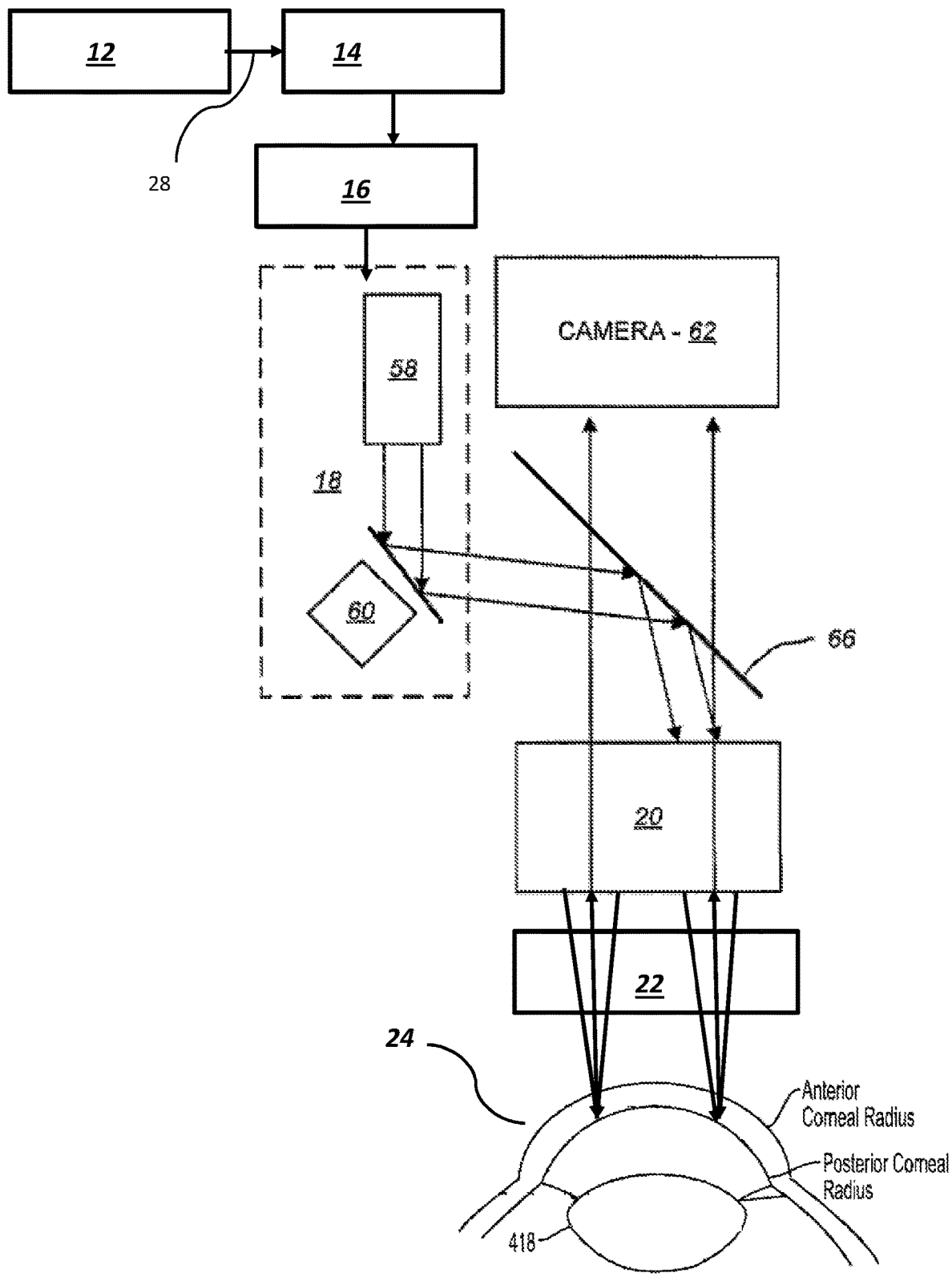
FIG. 12 is a schematic diagram illustrating the use of emission from eye tissue to verify the location scan with a camera of the laser surgery system of FIG. 1.

FIG. 12 schematically illustrates using a luminescence from an eye 24 to obtain a video image of the actual location of a laser scan. Eye 24 includes one or more components that emit light in response to absorbing electromagnetic radiation at wavelengths preferably less than 370 nm. The eye 24 is preferably connected to the objective 20 and scanning assembly 18 via patient interface 22. Light from light source 12 is directed to eye 24 via the confocal assembly 14, the shared optics 16 the scanner 18 and the objective 20. With the focal point of the electromagnetic radiation beam from light source 12 disposed, preferably sequentially, within the eye, the camera 62 is used to detect the actual location of the resulting emission from eye 24 based on the position of the focal point within eye 24. The luminescence is generally detected as one or more pixels, $P_{act}$. The observed location of the resulting fluorescent emission can be used in conjunction with calibration data for the camera 62 to determine x and y coordinates of the associated focal point in the treatment space and can be compared to the expected scan location of the incisions.

The camera image of the eye is preferably presented to a user as an en face image, such as shown in FIG. 13 with the pixels, Pact, corresponding to the actual location of the scan illuminated on the image.

The above described methods and systems permit a physician to verify the actual scan location of a contemplated incision in comparison to its expected location and also to confirm that the laser surgical system is adequately calibrated. For example, if the physician desired to make a cut at a predetermined position in an eye, the physical need only enter the necessary parameters to define the location and type of incision the physician intends to make. In one embodiment, the laser surgical system of the present invention is configured to receive these parameters and to project the defined incision onto a video image. In some embodiments, the video image then illustrates the expected position of the incision on the image, by, for instance, illuminating a set of Pixels, $P_{EL}$, corresponding to the intended location of the incision. The laser system is also preferably configured to carry out a treatment scan configured to make the incision at the predetermined location. As the pulsed laser scans the tissue, a resulting luminescence from the location of the treatment scan is detected and subsequently used to identify the actual location in the eye where the treatment scan was performed. Preferably, the actual location is illustrated on the video image by illuminating a set of pixels, $P_{act}$, corresponding to the position of the actual scan. Thus, in some embodiments, if the actual location of the scan differs from the expected location, the physician can visually make this determination by inspection of the video image.

In another embodiment, a warning is issued if a difference between the actual location and the expected location is greater than a predetermined threshold amount. This makes it possible to warn a physician or user, or stop the scan completely, even if the physician is not actively viewing the image.

Preferably, the system and methods are used throughout the entirety of the treatment scan. Specifically, in some embodiments, the progression of the treatment scan is monitored by successive images/frames captured during the treatment. In a preferred embodiment, successive frames of the image capture the progression of the treatment scan in real time. In some embodiments, the difference in detected luminescence between frames track the actual location and actual direction of the treatment scan. For example, when a confocal scan is being taken, a video is taken at the same time. In this manner, the system and methods can ensure that the entirety of the incision is placed at its expected location.

The methods described herein also provide a convenient method for confirming that a laser eye surgery system is adequately calibrated. With conventional imaging, a number of safeguards are generally in place to ensure proper calibration; however, a physician may have limited convenient procedures for determining whether the instrument is calibrated. The present invention allows the physician or other user to quickly assess the calibration of the laser surgical system.

It is also noted that the present invention provides a safeguard should the physician inadvertently type in the wrong coordinates for his cuts. In that scenario, the calibration would not necessarily be wrong but the physician would notice that the cutting was not taking place in the correct locations. This event would presumably prompt the physician to double check to see if he typed in the correct geometric coordinates. Further, this method would provide a safeguard should the calibration be off before a procedure by the inadvertent bumping of the camera or things of that nature.

In sum, many embodiments provide a method or system that detects an actual location of a laser scan within an object and verifies whether the laser scan is at the expected location. Other embodiments provide a method or system that detects an actual placement of an ocular incision within an eye and verifies whether the ocular incision is at the intended location. Other embodiments provide a method of verifying the calibration of a laser eye surgical system.

Alignment Examples

In certain examples, when an operator is utilizing the systems above, the operator may only be able to view the patient eye through a camera image. In certain examples, this may be a view of just the eyeball and no other reference features. Without other references, a user may become disoriented as to the direction the image of the eye is relative to the patient, and even which eye is being viewed. In certain example embodiments, it may be useful to include fiducials in the patient interface, so that a user may be able to better orient the image to the patient.

Figure 15A:
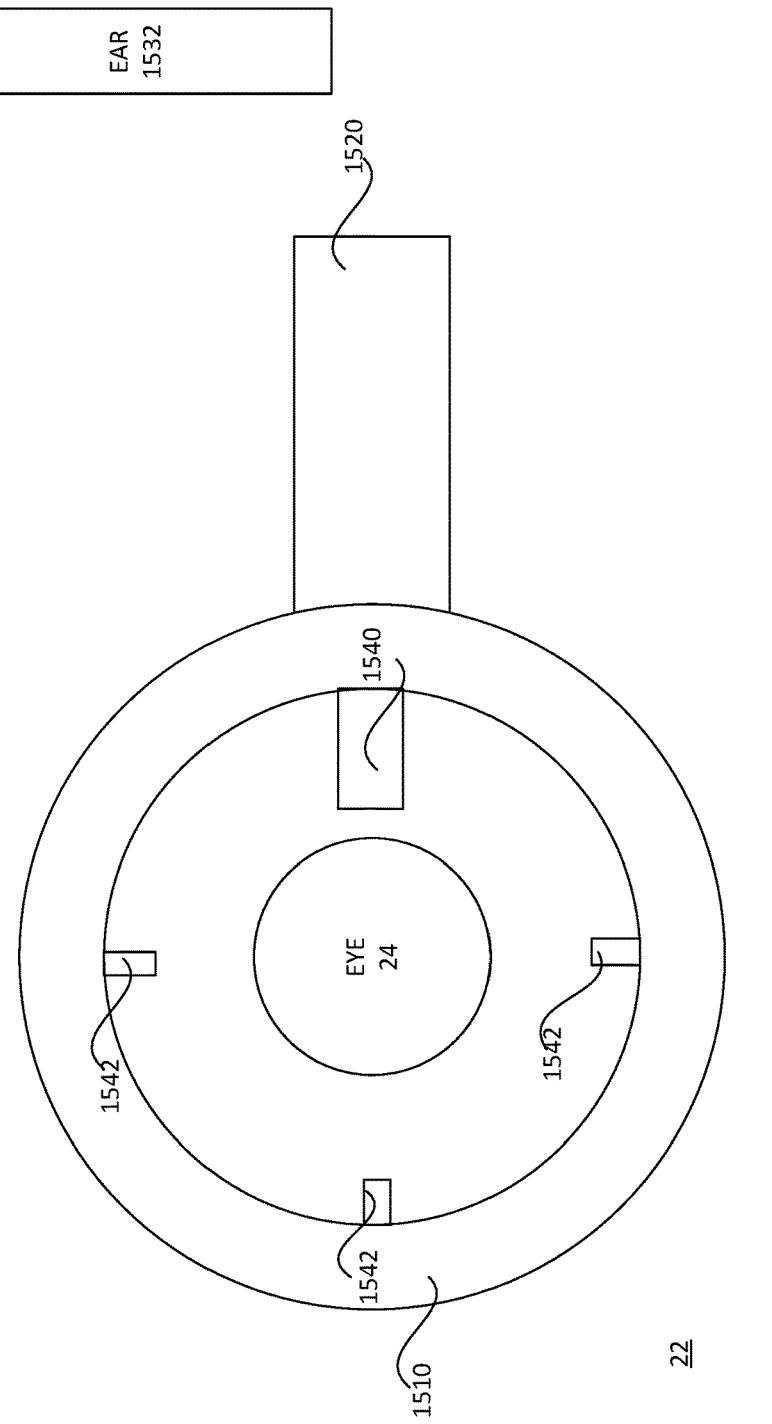
FIG. 15A is a diagram showing an example alignment embodiment as disclosed herein.

Referring now to FIG. 15A, various embodiments of the liquid optics patient interface 22 are discussed. The patient interface 22 allows for a liquid optics docking to take place between the eye 24 and the system 2 for conducting laser procedures on a patient's eye as described above.

The patient interface 22 may be placed on a patient during procedure, and can hold the liquid used as the interface for the laser systems described above. But during the procedure, the surgeon user may view the patient interface 22 and the patient's eye through a camera arrangement. In doing so, the surgeon may become disoriented as to the eye's orientation in the patient's head. In order to help the surgeon to understand the orientation of the patient's eye, it may be useful to indicate orientation markers on the patient interface itself, because the eyeball, when viewed through the camera arrangement, may not indicate any type of orientation.

Thus, from the top down, a video camera 62 can capture an image of the eye 24 and the patient interface 22. With the addition of various fiducials inside the patient interface, within the field of view of a camera looking down at the eye 24 and the patient interface 22, a surgeon or other operator could more easily understand the orientation of the eye 24 to the patient interface 22 and its relation to the ear 1532 and nose 1530 of the patient.

Any of various steps, dots, lines, arrows, notches, and/or other fiducials could be used in the patient interface 22 to show such orientation. Examples include but are not limited to raised steps, indented steps, colored indicators, lines, etched grooves, raised bumps, notches, arrows, boxes and/or any combination of these or other indicators.

In certain example embodiments, the patient interface 22 may have a rim 1510 and a cup for containing the liquid interface. The patient interface 22 may include an optional tool access portion 1520 which may extend laterally from the rim 1510 of the patient interface 22. This tool access portion 1520 may be used in some embodiments and may be a tunnel through which the surgeon may insert tools to access the eye 24 during procedure. In such embodiments, this tool access portion 1520 requires the proper amount of space for operation of the various tools, it should be orientated on the patient so that the tool access portion 1520 is pointed temporally, toward the temple of the patient and not toward the bridge of the nose of the patient. This may allow for enough room for the surgical tools to access the tool access portion 1520 from the side of the head area.

In one example, as shown in FIG. 15A, a large step 1540 is shown. In some embodiments, this step 1540 is close to the tool access portion 1520 if one is used. Certain embodiments include steps at various intervals to help orientation. In one example, at 90 degree intervals, around the inside of the rim 1510 of the patient interface 22, smaller steps 1542 are shown. In this way, a surgeon looking down at the patient interface 22 would quickly orient the surgeon to the position of the interface 22 on the eye 24.

Figure 15B:
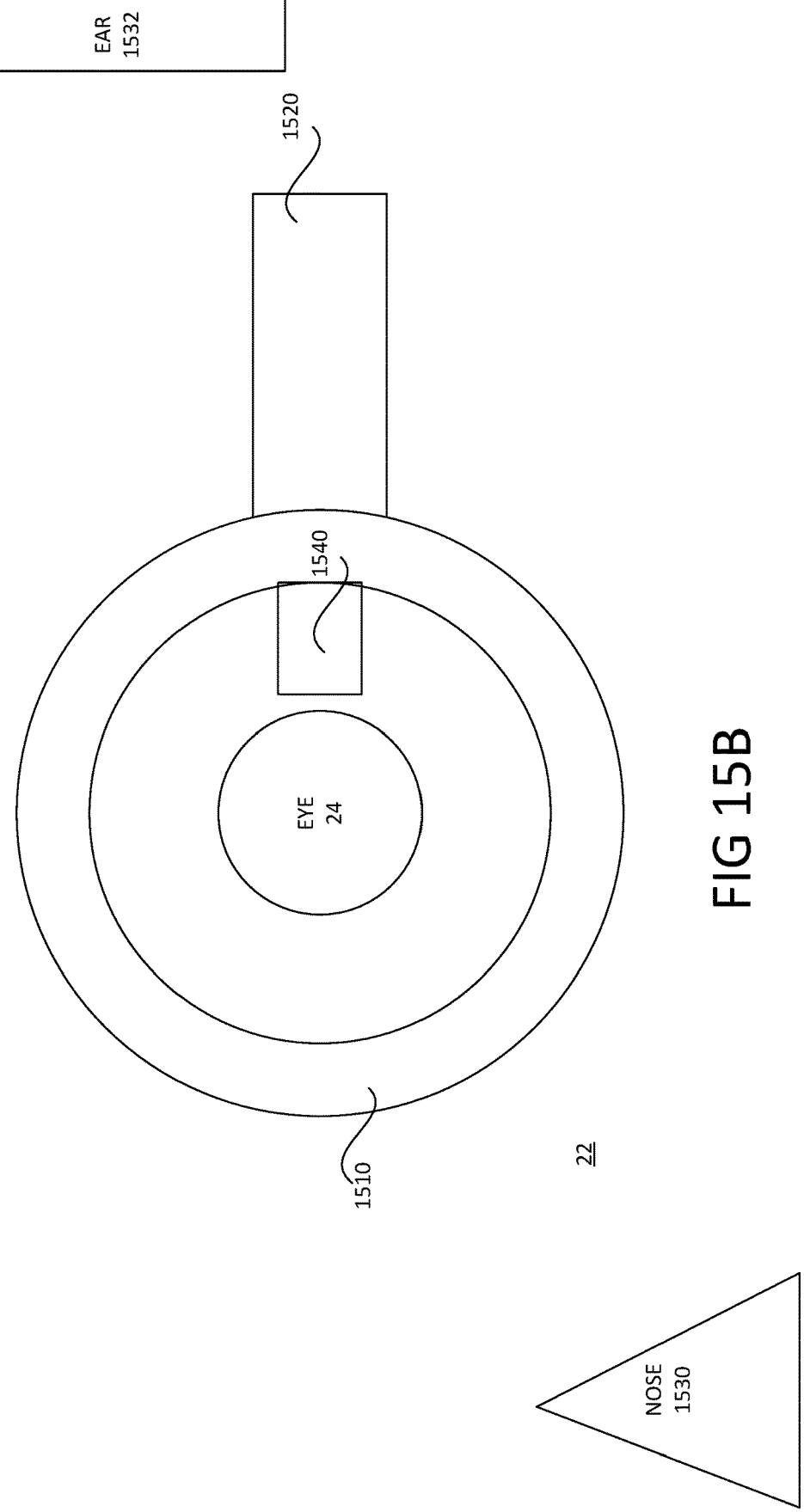
FIG. 15B is a diagram showing an example alignment embodiment as disclosed herein.

In the example embodiment shown in of FIG. 15B, instead of four steps at 90 degree intervals, only one large step 1540 is shown. In embodiments using a tool access portion 1520, this large step is oriented near the tool access port 1520 so an operator could orient the patient interface 22 on the patient, with the nose 1530 and ear 1532 in the correct orientation. It is shown that the patient interface 22 is orientated with the tool access portion 1520 orientated toward the temple or ear 1532 of the patient and not toward the nose 1530 of the patient. In embodiments without such tool access portion, the steps can be used to orient the interface 22 to the patient.

Figure 15C:
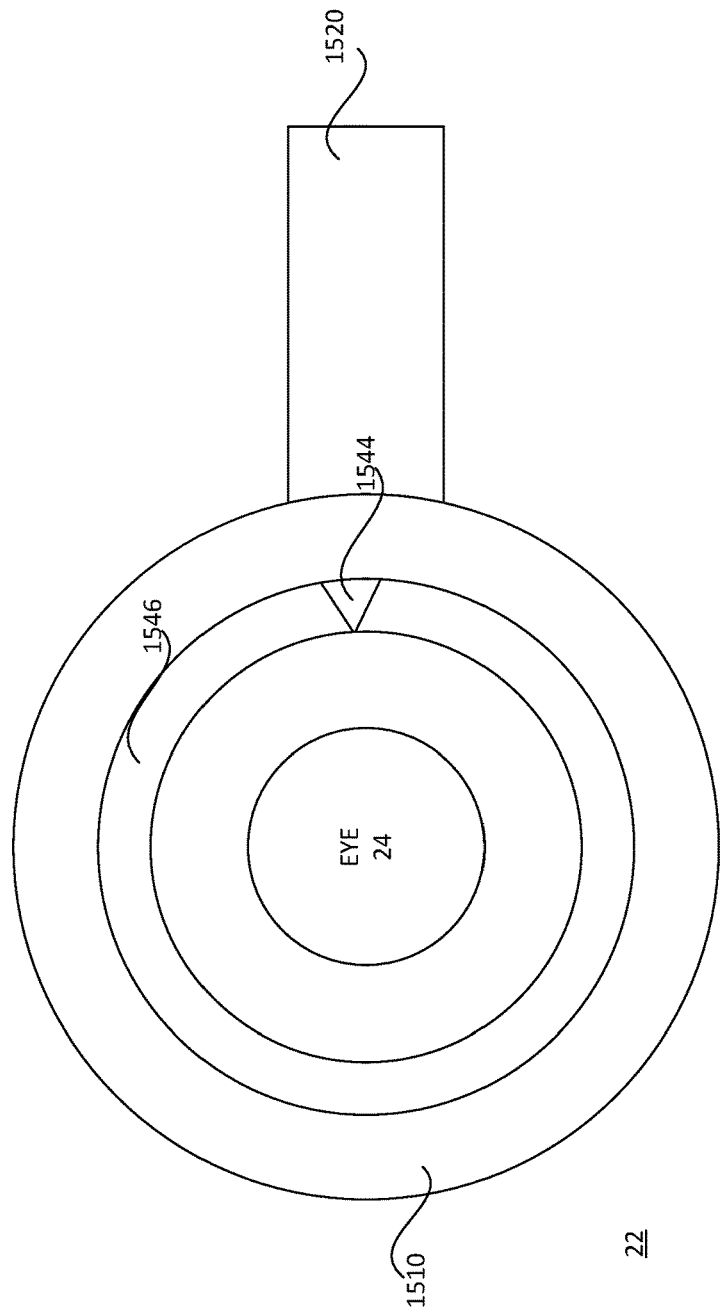
FIG. 15C is a diagram showing an example alignment embodiment as disclosed herein.
Figure 15C:
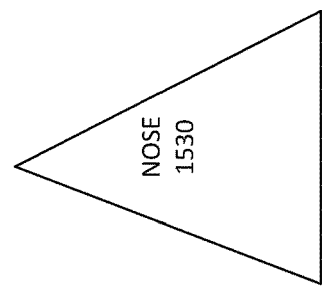

FIG. 15C shows another example where instead of a step, there is a notch 1544 cut out of an interior rim 1546 of the patient interface. In some examples, this notch is located near the tool access portion 1520 just as the large step was located in FIG. 15A and FIG. 15B. Again, certain embodiments may not use a tool access portion in which case the notches 1544 may be used to merely indicate the patient orientation. In various embodiments, any number of notches could be arranged of various sizes and colors, in any combination.

Figure 15D:
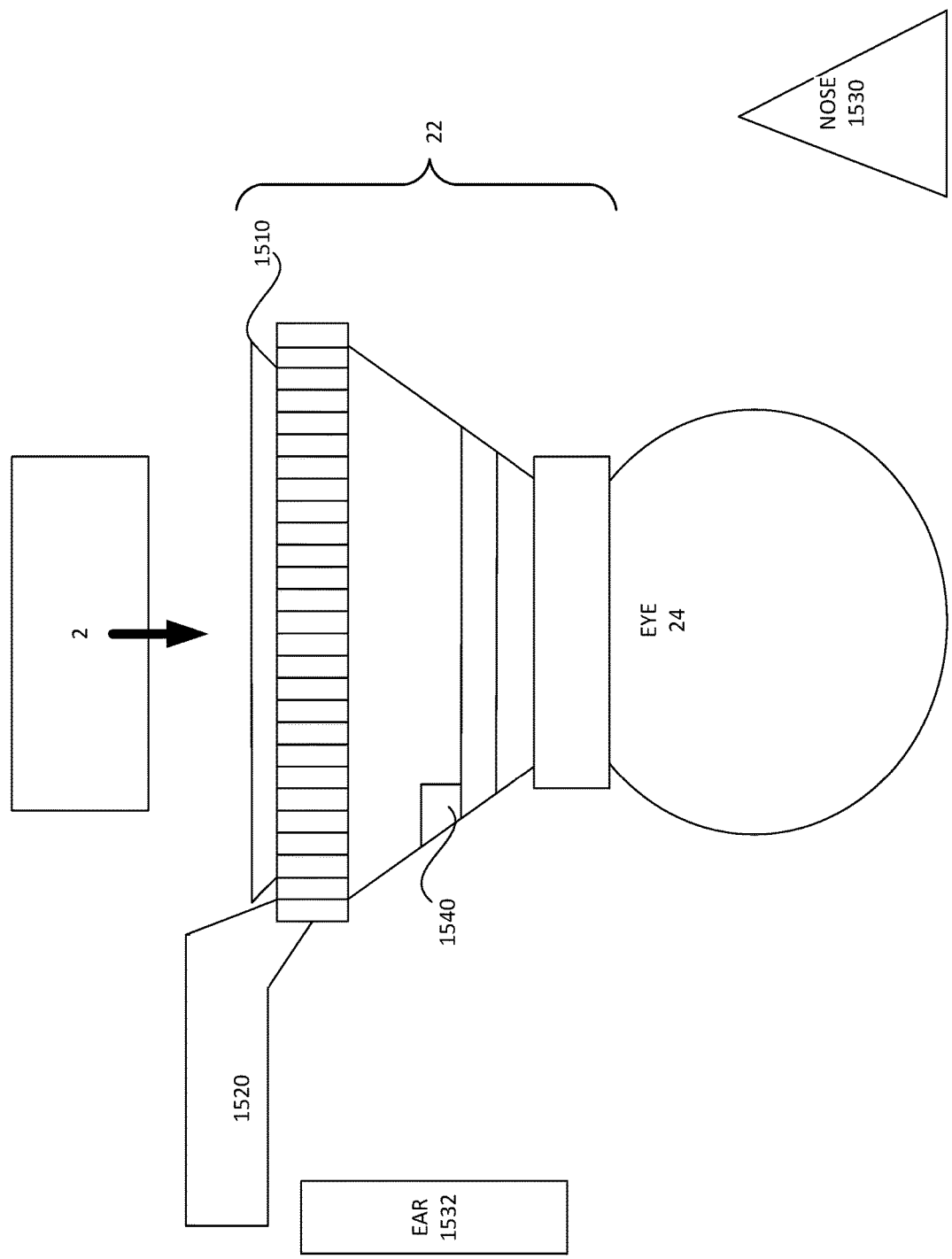
FIG. 15D is a diagram showing an example alignment embodiment as disclosed herein.

FIG. 15D shows an example side view of the patient interface 22 attached to a patient eye 24 as for procedure. The nose 1530 and ear 1532 of the patient are again shown for orientation purposes. In this example side view, the tool access portion 1520 is properly oriented toward the ear 1532 of the patient. In examples without such tool access portions, the interface may orient to the patient for the laser system only. The rim 1510 of the patient interface 22 is shown with the system 2 configured to dock with the patient interface 22 for procedure.

In the example, a large step 1540 is shown as a step of an interior portion of the patient interface 22. The large step 1540 is oriented to the patient interface 22 in the same direction as the tool access portion 1520 if such a portion exists. Because the large step 1540 is positioned in line with the tool access portion 1520, the user looking down, from the perspective of the system 2 would be able to orient the image and know which direction the patient interface is oriented. In embodiments using a tool access portion 1520, such a portion may be indicated by the step 1540 as it may stick out of the patient interface 22.

Figure 15E:
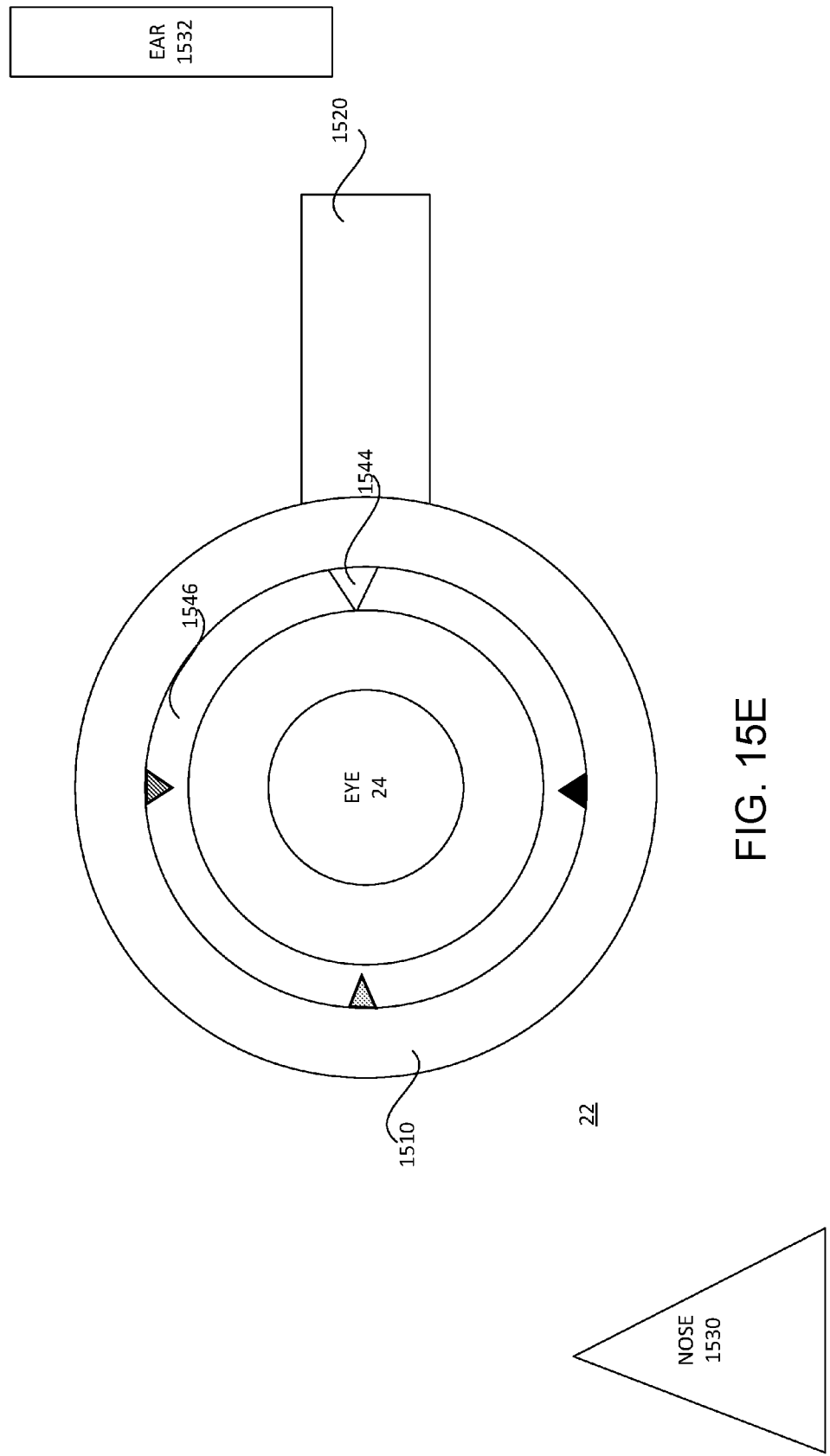
FIG. 15E is a diagram showing yet another example alignment embodiment as disclosed.

FIG. 15E is a diagram showing yet another example alignment embodiment. As shown in FIG. 15E, the notched interior rim includes colored notches as direction indicators of 90 degree increments around the inside of the cup, wherein the direction indicators are colored differently than the notch indicating the location of the tool access portion, and wherein at least two direction indicators are of different sizes.

Figure 16:
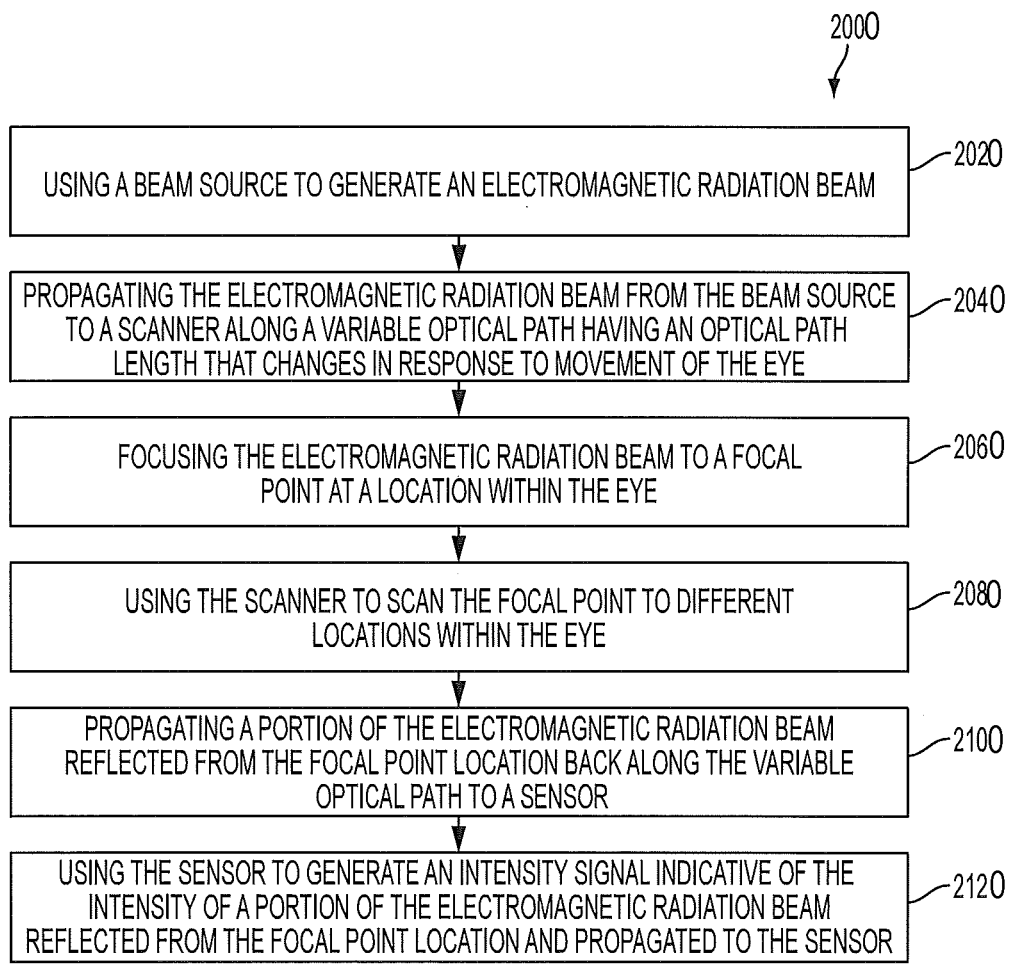
FIG. 16 is a simplified process of imaging and/or modifying an intraocular target according to an embodiment of the invention.

FIG. 16 is a simplified block diagram of acts of a process 2000 of the laser surgery system 10 according to many embodiments for imaging an eye. The laser surgery system 10 uses a beam source to generate an electromagnetic radiation beam (Action Block 2020). The laser surgery system 10 propagates the electromagnetic radiation beam from the beam source to a scanner along a variable optical path having an optical path length that changes in response to movement of the eye (Action Block 2040). The laser surgery system 10 focuses the electromagnetic radiation beam to a focal point at a location within the eye (Action Block 2060). A scanner of the laser surgery system 10 scans the focal point to different locations within the eye (Action Block 2080). The laser surgery system 10 propagates a portion of the electromagnetic radiation beam reflected from the focal point location back along the variable optical path to a sensor (Action Block 2100). The sensor generates an intensity signal indicative of the intensity of a portion of the electromagnetic radiation beam reflected from the focal point location and propagated to the sensor (Action Block 2120).

Figure 17:
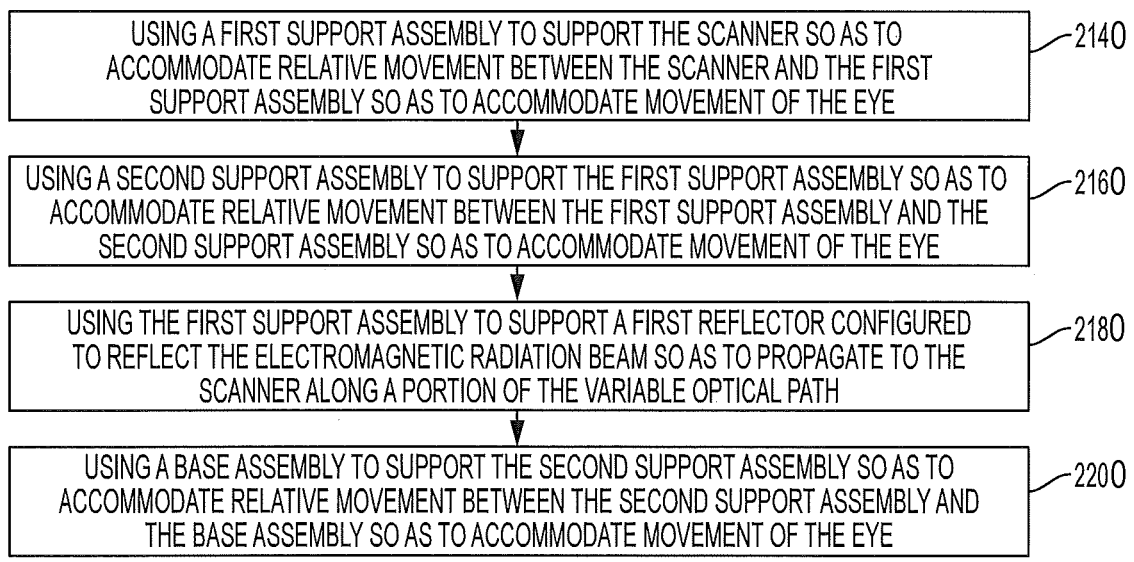
FIGS. 17, 18, and 19 are simplified processes that can be accomplished as part of the process of FIG. 3 according to an embodiment of the invention.
Figure 18:
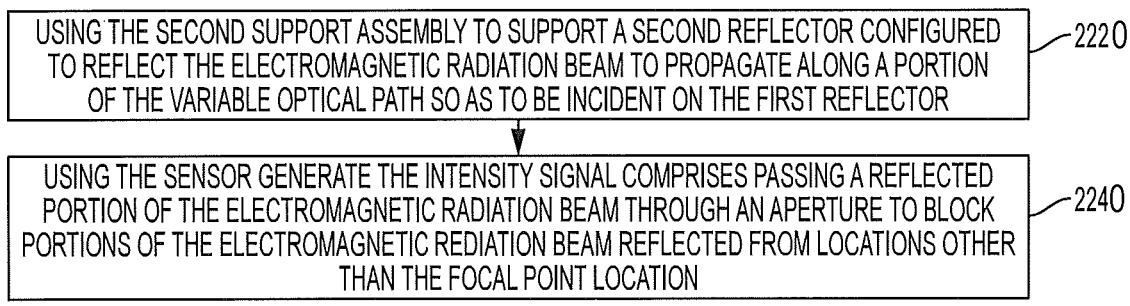
Figure 19:
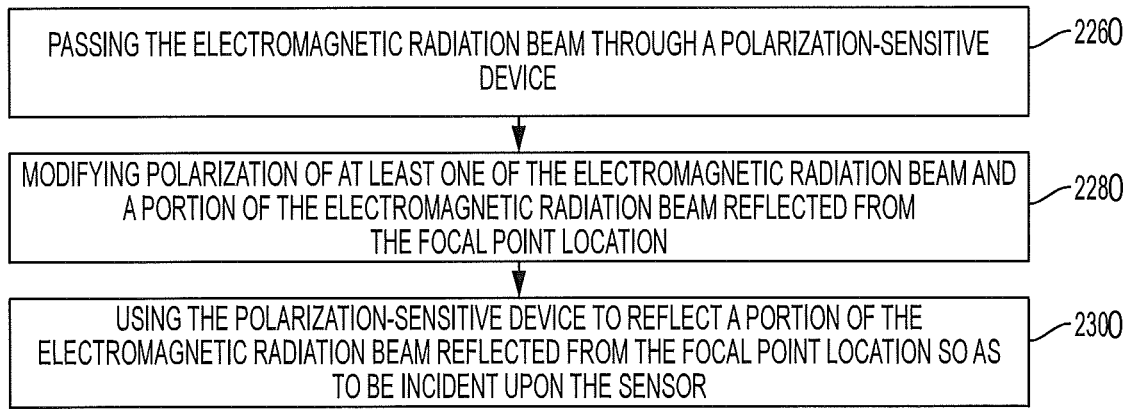

FIGS. 17, 18, and 19 illustrate options that may be accomplished as part of the process 2000. For example, the laser surgery system 10 may include a first support assembly for supporting the scanner to accommodate movement of the eye (Action Block 2140). The laser surgery system 10 may also use a second support assembly to further support the first support assembly to accommodate movement of the eye (Action Block 2160). The first support assembly supports a first reflector configured to reflect the electromagnetic radiation beam so as to propagate to the scanner along a portion of the variable optical path (Action Block 2180). A base assembly supports the second support assembly to accommodate movement of the eye (Action Block 2200). The second support assembly may support a second reflector configured to reflect the electromagnetic radiation beam to propagate along a portion of the variable optical path so as to be incident on the first reflector (Action Block 2220). The sensor generates the intensity signal by passing a reflected portion of the electromagnetic radiation beam through an aperture to block portions of the electromagnetic radiation beam reflected from locations other than the focal point location (Action Block 2240). The electromagnetic radiation beam passes through a polarization-sensitive device (Action Block 2260) which modifies the polarization of at least one of the electromagnetic radiation beam and a portion of the electromagnetic radiation beam reflected from the focal point location (Action Block 2280). The polarization-sensitive device reflects a portion of the electromagnetic radiation beam reflected from the focal point location so as to be incident upon the sensor (Action Block 2300).

Figure 20A:
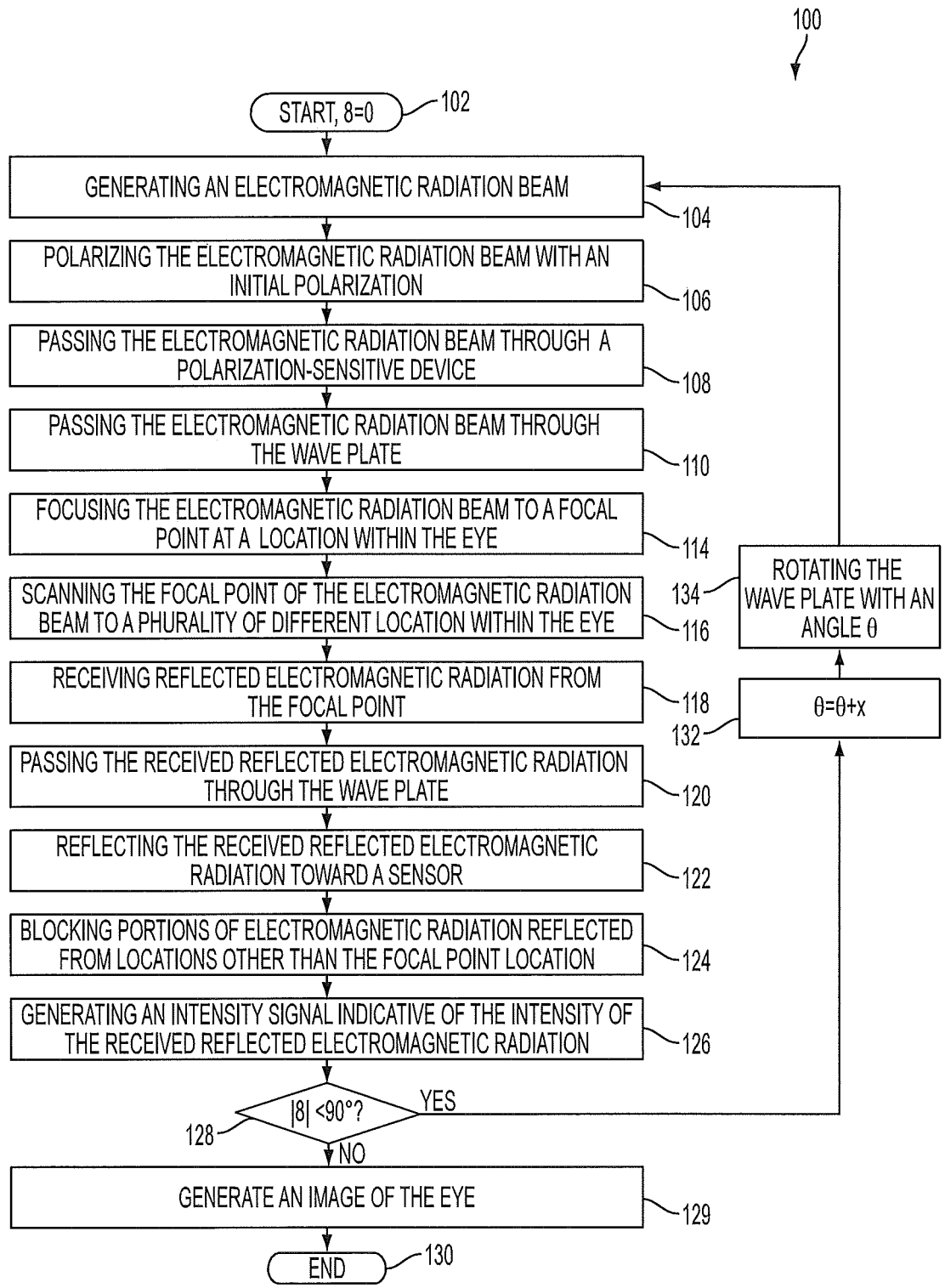
FIG. 20A is a process for imaging an eye, according to an embodiment of the invention.

FIG. 20A shows a process 100 of a laser surgery system for imaging a cornea of an eye according to some embodiments of the invention. In some situations, it may be desirable to accurately image the cornea with a confocal detector. Further, it may be desirable to accurately identify or detect the anterior and posterior boundaries of the cornea, for example, to determine a thickness of the cornea. The intensity of a confocal signal may change substantially between the front of the cornea and the back of the cornea, which can make detection more difficult than would be ideal. This change in intensity may be related to local changes in birefringence of the cornea, which may cause signal loss at a confocal detector. Additionally, in at least some eyes, the birefringence properties of the cornea may vary with corneal depth. Further, corneal birefringence properties may vary laterally and radially in unpredictable amounts. Thus, in some embodiments, the light passing back through the one-quarter wave plate may be rotated by an angle other than ninety degrees on the second pass through a polarizing beam-splitter, such that some of the light is reflected toward the light source instead of toward the sensor. The process 100 provided in FIG. 7A may address some of the difficulties of imaging the back surface of the cornea. Process 100 may start (Action Block 102) with a variable θ equal to zero. The variable θ may represent a rotation angle of the wave plate relative to an initial position of the wave plate. Accordingly, the wave plate may be at an initial position at the start (Action Block 102) of process 100. The laser surgery system generates an electromagnetic radiation beam using a beam source, e.g., laser 32 (Action Block 104). The electromagnetic beam is polarized (Action Block 106) with an initial polarization. The electromagnetic radiation beam passes through a polarization-sensitive device (Action Block 108) and through the wave plate (Action Block 110). The electromagnetic radiation beam may be focused to a focal point at a location within the eye (Action Block 114), and may scan the focal point to a plurality of different locations within the eye (Action Block 116). In response to focusing the electromagnetic radiation beam and/or scanning the focal point of the electromagnetic radiation, electromagnetic radiation may be reflected from the focal point and received by the laser surgery system (Action Block 118). The received reflected electromagnetic radiation may be passed through the wave plate (Action Block 120), and further reflected by the polarization-sensitive device toward a sensor (Action Block 122). Portions of electromagnetic radiation reflected from locations other than the focal point location may be blocked (Action Block 124), for example, by an aperture. An intensity signal indicative of the intensity of the received reflected electromagnetic radiation may be generated by the sensor (Action Block 126). Once the magnitude of angle θ is greater than or equal to ninety degrees (e.g., the wave plate has rotated ninety degrees from the initial position of the wave plate) (Decision Block 128), the laser surgery system generates an image of the eye (Action Block 129 and End 130). If the magnitude of angle θ is less than ninety degrees (Decision Block 128), variable θ may be increased by an incremental amount x. The wave plate may be mechanically rotated by a rotation angle θ (Action Block 134). Thereafter, the laser surgery system may loop back and repeat Action Blocks 104-126 with the wave plate rotated by an angle θ. Process 100 may end when steps 104-126 are performed with the wave plate rotated by ninety degrees from the initial position of the wave plate.

As should be appreciated, in an embodiment of process 100, the laser surgery system 10 scans the eye with focal points of more than one electromagnetic radiation beam, where the electromagnetic radiation beams have varying degrees of polarization due to a varying wave plate orientation. The plurality of scans, and hence the plurality of intensity signals, may help compensate for difficulties in imaging the anterior and posterior surface of the cornea due to the birefringence of the cornea. Some intensity signals may include strong intensity signals from an anterior portion of a cornea of the eye. Other intensity signals may include strong intensity signals from posterior portions of the cornea. In some embodiments, the plurality of intensity signals may be used in-part or in whole to form a composite signal to accurately identify anterior and posterior details of a cornea, such as the anterior and posterior surfaces. Accordingly, the plurality of scans may compensate for imaging signal loss due to local cornea birefringence properties.

In many embodiments, the above methods may be performed by the laser surgery system 10 illustrated in FIG. 1 and FIG. 2. For example, laser 32 may be used to perform step 104. Polarizer and beam dump device 42 may be used to perform step 106. At step 108, the electromagnetic radiation beam may pass through the polarized beam-splitter 48. The one-quarter wave plate 56 may be used to modify the initial polarization of the electromagnetic radiation beam to perform step 110. XY-scan device 60 and Z-scan device 58 may be used to perform step 114 and step 116. At step 120, the one-quarter wave plate 56 may be used to receive and modify a polarization of the reflected electromagnetic radiation. The polarized beam-splitter 48 may be used to reflect the reflected electromagnetic radiation toward a sensor at step 122. Pinhole aperture 52 may be used to perform step 124 and detector 54 may be used to perform step 126. In some embodiments, laser surgery system 10 may be preprogrammed to perform multiple scans according to method 100.

Figure 20B:
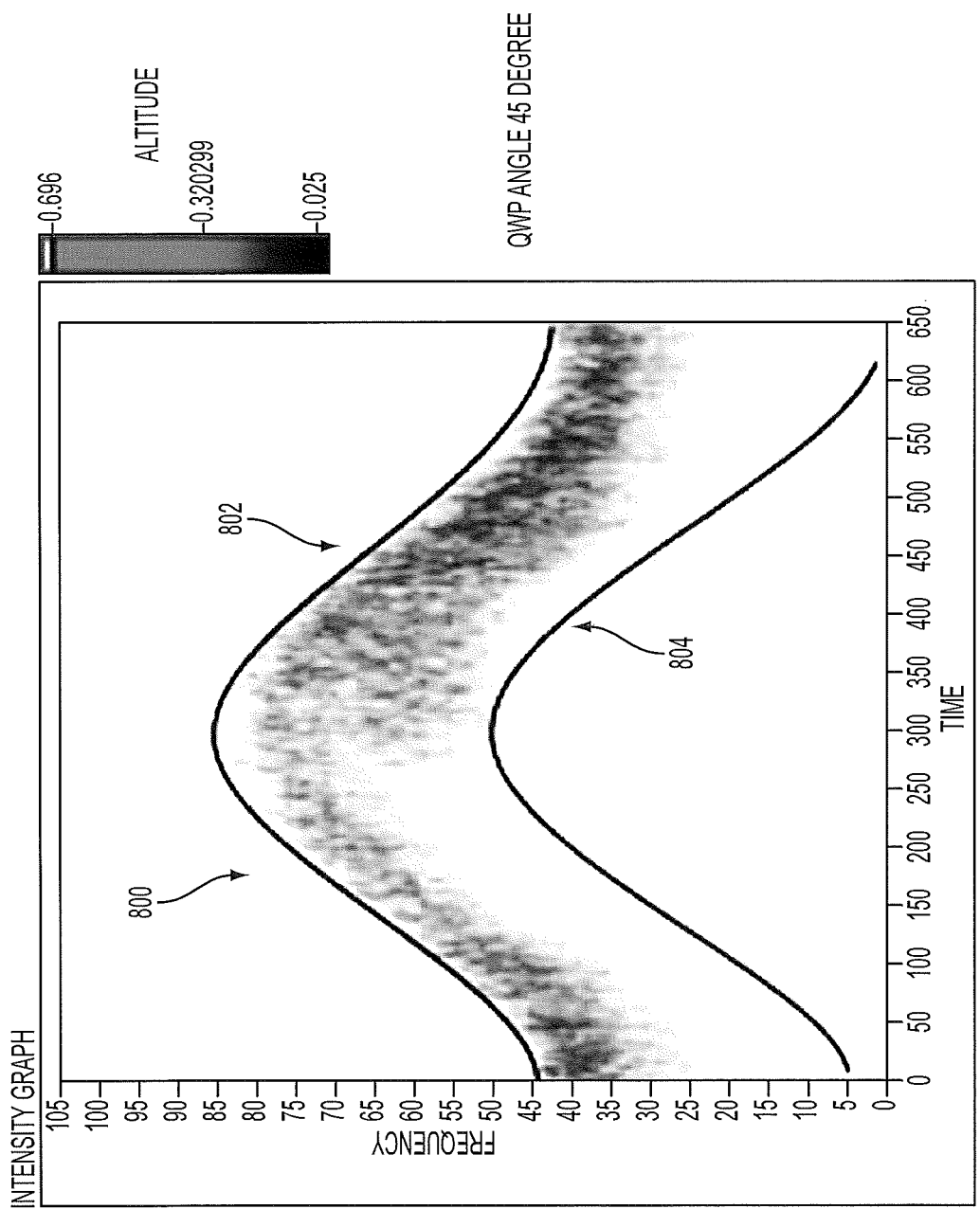
FIGS. 20B-20C show two exemplary intensity profiles of a cornea of an eye generated according to the process shown in FIG. 20A.
Figure 20C:
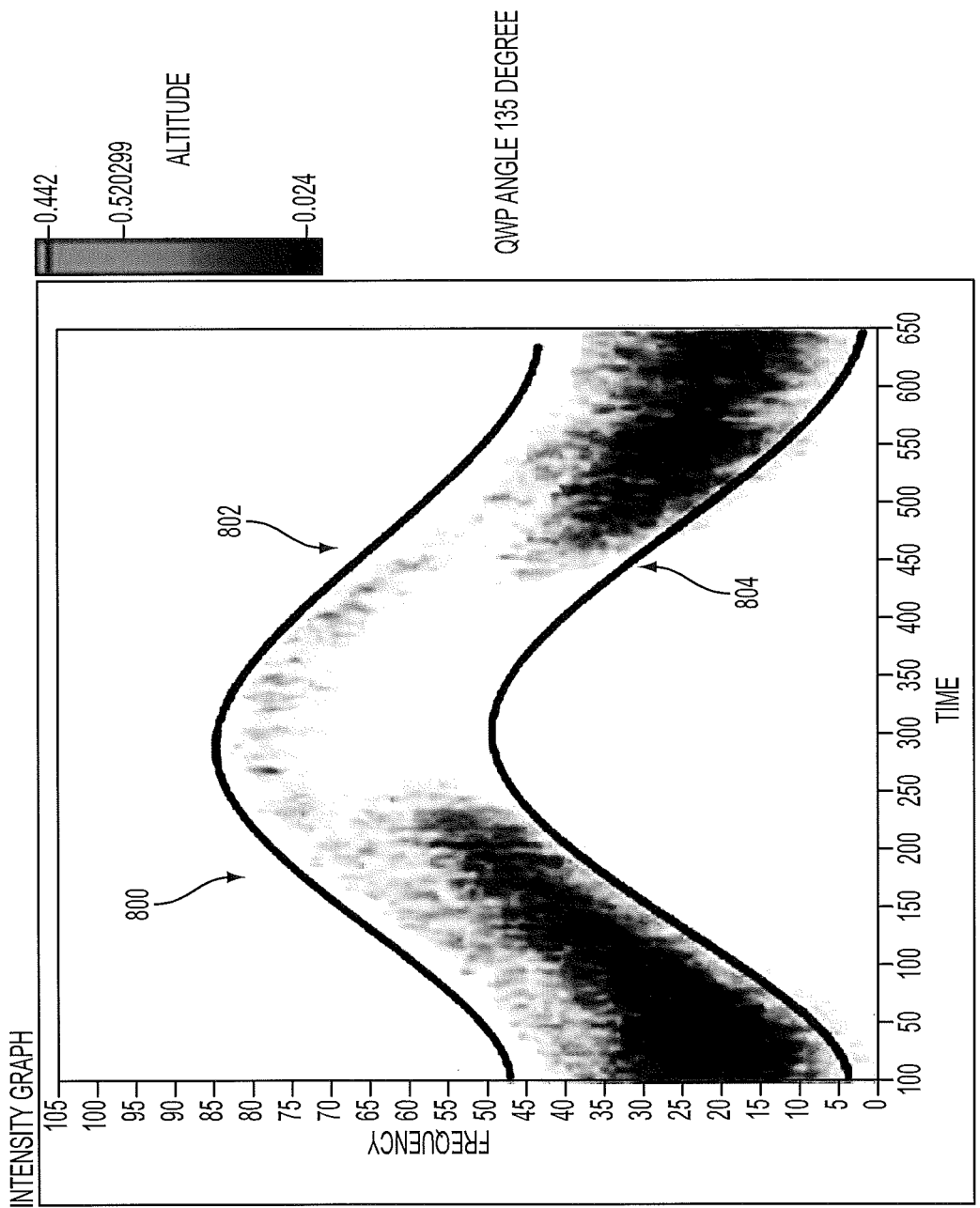

Variable x may be any incremental value. In some embodiments, x may be one, two, three, five, fifteen, thirty, forty-five, or ninety degrees. In some situations, it may be desirable to perform process 100 quickly. Optionally, process 100 may be completed with two scans when x is ninety degrees. In such an embodiment, the eye may be scanned twice with an electromagnetic radiation beam focal point. This may be done preferably to minimize the effects of inadvertent eye movement relative to the imaging system between or during sequential scans. FIG. 20B and FIG. 20C illustrate two exemplary intensity profiles from a cornea 800 generated by such a process. FIG. 20B shows a generated intensity profile of reflected electromagnetic radiation from a cornea 800 when the one-quarter wave plate has an initial position of forty-five degrees. As can be seen, the scan in FIG. 20B may include an intensity profile with higher intensity at an anterior surface 802 of the cornea 800, but may have lower intensity toward some portions of the posterior surface 804 of the cornea 800. The intensity signal toward the posterior surface 804 of the cornea 800 may decrease toward the peripheral edge of the cornea 800. After the scan illustrated in FIG. 20B, a second scan illustrated in FIG. 20C may be performed. FIG. 20C shows a generated intensity profile of reflected electromagnetic radiation from the cornea 800 after the one-quarter wave plate is rotated ninety degrees from the initial position to one hundred thirty-five degrees. As can be seen, the scan in FIG. 20C may include an intensity profile with lower intensity at an anterior surface 802 of the cornea when the one-quarter wave plate is rotated to one hundred thirty five degrees. The scan in FIG. 20C, however, may include an intensity profile with higher intensity at portions of the posterior surface 804 of the cornea 800. In particular, the scan in FIG. 10C may provide an intensity profile with higher intensity at the posterior surface of the cornea 800 and near the peripheral edge of the cornea 800. Accordingly, the two scans shown in FIGS. 20B and 20C may be used together to account for local variations and to more accurately identify both the anterior surface 802 and the posterior surface 804 of the cornea 800. Optionally, a corneal thickness may be accurately calculated thereafter.

The surface profile of a cornea can be measured in one or more of many ways, and may comprise one or more of an anterior corneal surface topography profile, a posterior a corneal surface topography profile, or a corneal thickness profile as obtained from the generated intensity profiles. In many embodiments, the surface profile comprises a representation of a three dimensional profile and may comprise an extraction of one or more parameters from one or more images, such as an extraction of keratometry values from a corneal topography system or tomography system integrated with the surgical laser. The one or more parameters can be used to determine a tissue treatment pattern on the eye, such as the angular location, depth, arc length and anterior to posterior dimensions of incisions. For instance, the surface profile can be used to determine an axis of treatment of a plurality of arcuate incisions, the plurality of arcuate incisions extending along an arc transverse to the axis of treatment.

In many embodiments, the optical surface of the eye is fit with one or more with one or more of a Fourier transform, polynomials, a spherical harmonics, Taylor polynomials, a wavelet transform, or Zernike polynomials. The optical tissue surface may comprise one or more of the anterior surface of the cornea, the posterior surface of the cornea, the anterior surface of the lens capsule, the posterior surface of the lens capsule, an anterior surface of the lens cortex, a posterior surface of the lens cortex, an anterior surface of the lens nucleus, a posterior surface of the lens nucleus, one or more anterior surfaces of the lens having a substantially constant index of refraction, one or more posterior surfaces of the lens having a substantially constant index of refraction, the retinal surface, the foveal surface, a target tissue surface to correct vision such as a target corneal surface, an anterior surface of an intraocular lens, or a posterior surface of an intraocular lens, for example.

Figure 21:
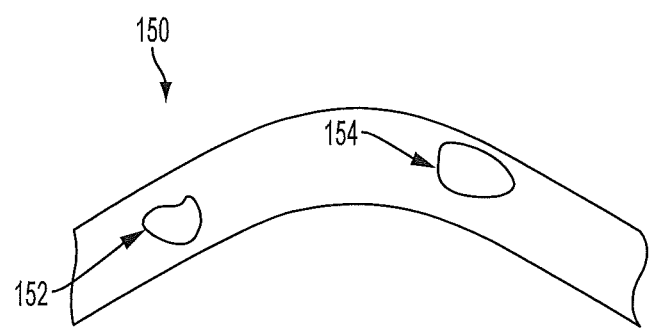
FIG. 21 is an exemplary illustration showing a plurality of regions of the cornea of an eye, wherein according to an embodiment of the invention, the regions may have varying birefringence properties.

In an embodiment, a cornea 150, as illustrated in FIG. 21, may have a first region 152 with a first birefringence and a second region 154 with a second birefringence. Thus, in imaging the cornea, a first electromagnetic radiation beam may be directed through the first region 152 of the cornea 150 to a first location in the eye. The first electromagnetic radiation beam may have a first polarization. A second electromagnetic radiation beam may be directed through the second region 154 of the cornea 150 to a second location in the eye. The second electromagnetic radiation beam may have a second polarization different than the first polarization. An image of the eye encompassing the first and second locations may be generated using electromagnetic radiation signals reflected from the eye in response to the steps of directing the first and second electromagnetic radiation beams. As such, the laser surgery system 10 may provide a single composite image that uses a plurality of beams with varying polarization to account for local differences in corneal birefringence properties.

Figure 22:
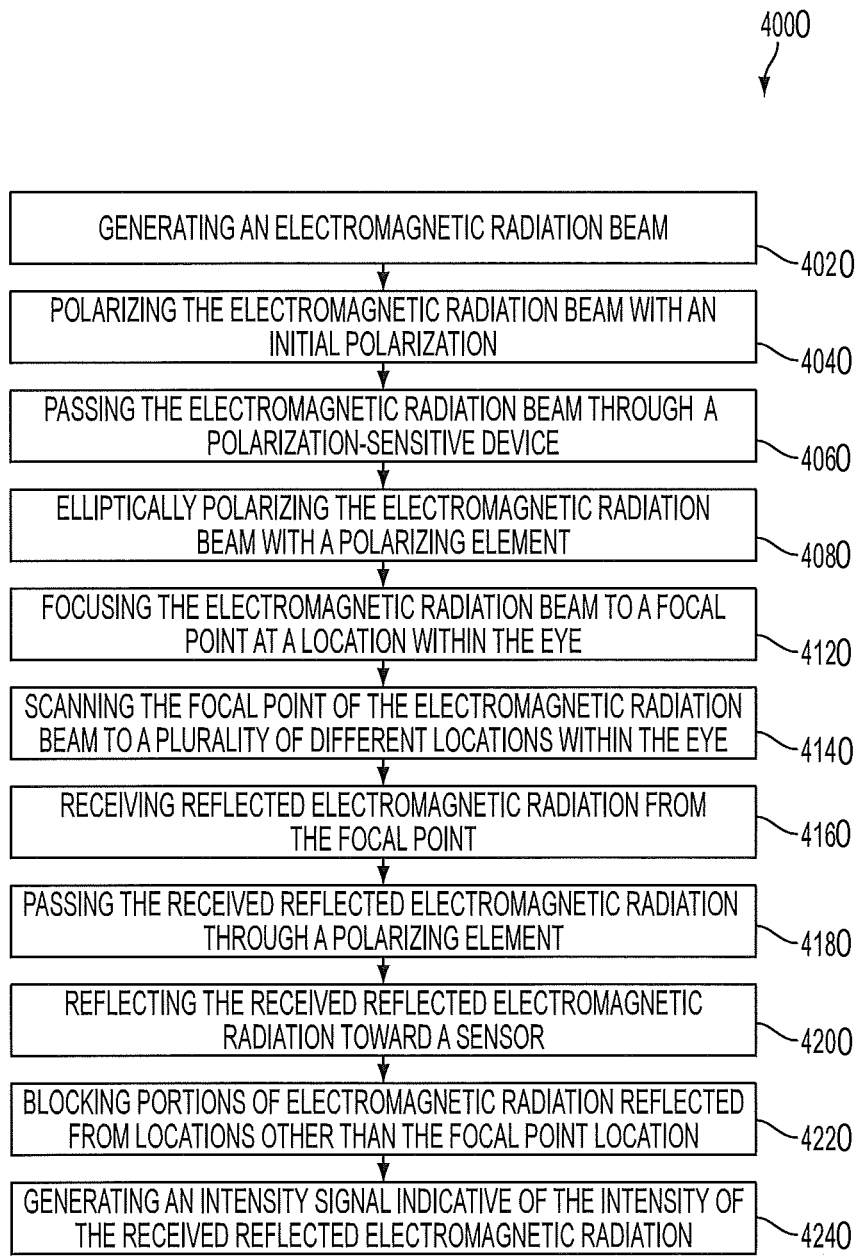
FIG. 22 is another process for imaging an eye according to an embodiment of the invention.

FIG. 22 shows another process 4000 of the laser surgery system 10 for imaging a cornea of an eye according to some embodiments of the invention. In some situations, process 4000 may be used to compensate for birefringence of the cornea to accurately identify its anterior and posterior boundaries. The laser surgery system 10 generates an electromagnetic radiation beam (Action Block 4020), which may be polarized with an initial polarization (Action Block 4040). The electromagnetic radiation beam passes through a polarization-sensitive device (Action Block 4060) and is elliptically polarized (Action Block 4080). The laser system surgery 10 focuses the elliptically polarized electromagnetic radiation beam to a focal point at a location within the eye (Action Block 4120), and scans the focal point to a plurality of different locations within the eye (Action Block 4140). The laser system surgery 10 receives reflected electromagnetic radiation from the focal point (Action Block 4160). The received reflected electromagnetic radiation passes through the polarizer (Action Block 4180) and is reflected or directed toward a sensor (Action Block 4200). The laser surgery system 10 may block portions of electromagnetic radiation reflected from locations other than the focal point location (Action Block 4220). The laser surgery system 10 may generate an intensity signal that is indicative of the intensity of the received reflected electromagnetic radiation.

In an embodiment of the process 4000, the laser surgery system 10 may use elliptically polarized light to identify and/or image the anterior and posterior portions of a cornea because, for example, elliptically polarized light will not produce linearly polarized light at one angle on the second pass through the beam-splitter such that the signal will change with less depth.

Figure 23A:
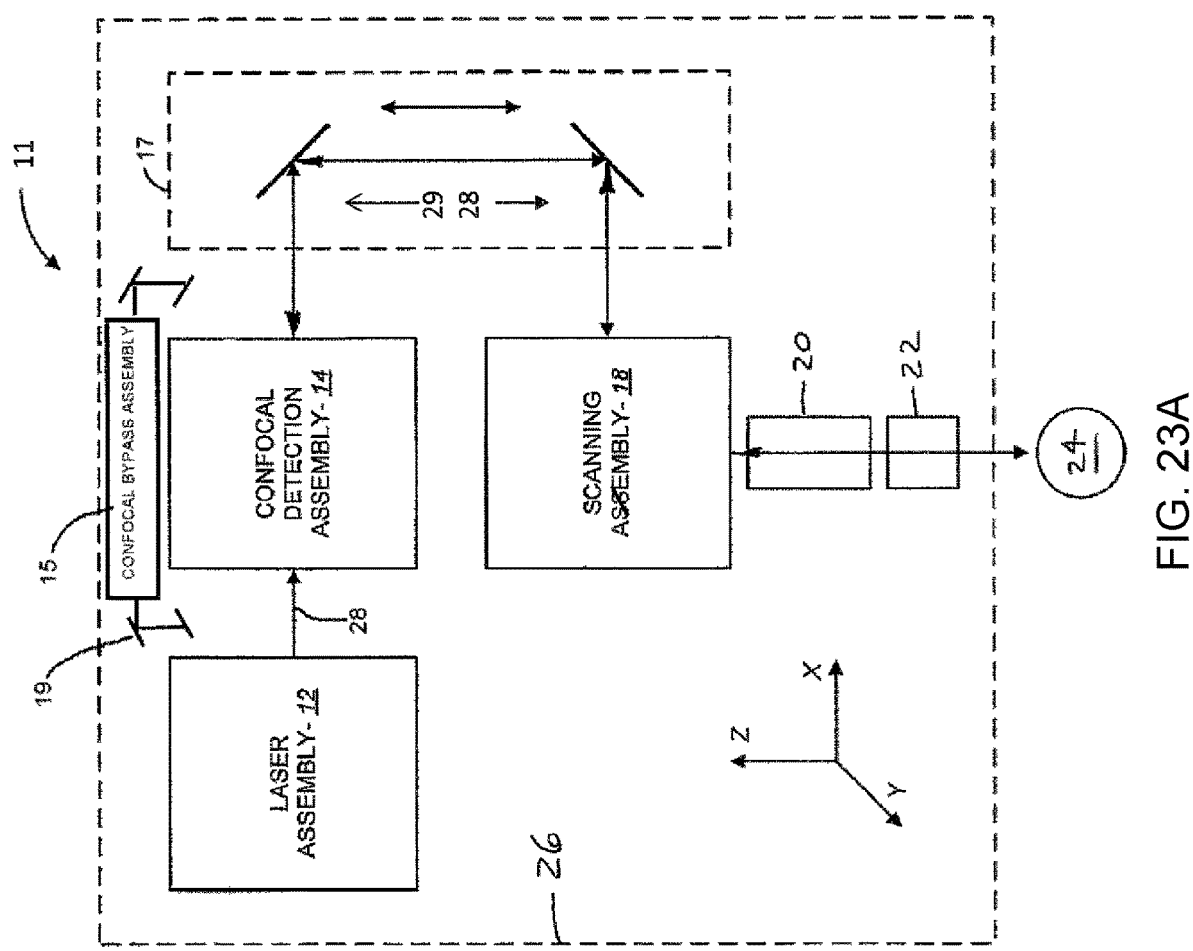
FIG. 23A and FIG. 23B are a schematic diagrams of a laser surgery system according to another embodiment.
Figure 23B:
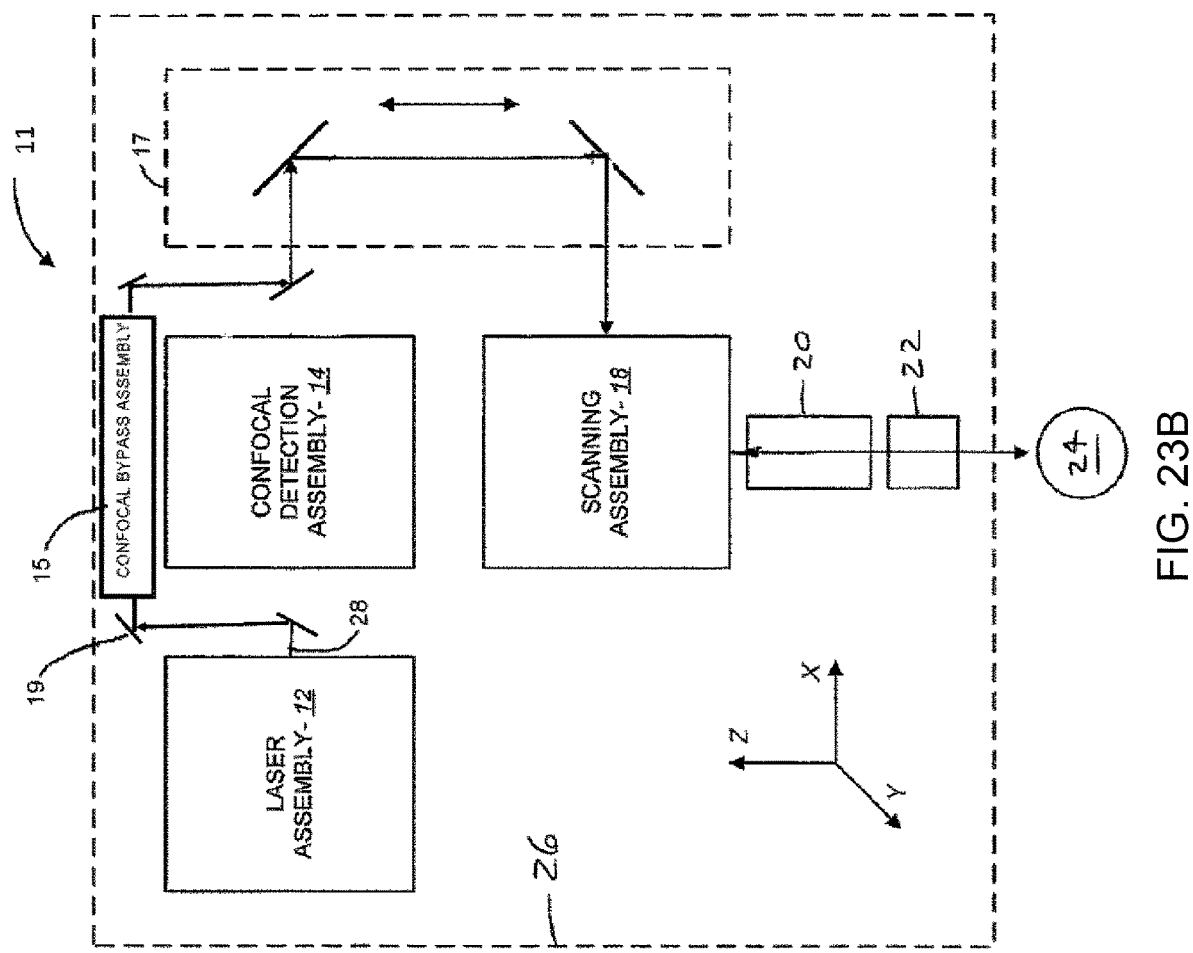

FIG. 23A and FIG. 23B schematically illustrate a laser surgery system 11 according to many embodiments. The laser surgery system 11 includes a laser assembly 12, a confocal detection assembly 14, confocal bypass assembly 15, a transfer optical path 17, a scanning assembly 18, an objective lens assembly 20, and a patient interface device 22. The laser surgery system 11 includes elements as described in the laser surgery system 10, as shown in FIG. 2. The confocal bypass assembly 15 generally includes at least one optical element 19 and is operable to reversibly divert the optical path of reflected electromagnetic beam 29 (a portion of electromagnetic beam 28) around at least one optical element (not shown) that delivers a portion of a reflected electromagnetic beam 29 to a sensor in the confocal detection assembly 14. By bypassing the optical element of the confocal detection assembly 14, the imaging system is inactivated because the reflected light 29 is not diverted to a sensor in the confocal bypass assembly 14. In the embodiment shown in FIG. 23A, the confocal bypass assembly 15 is represented in a state where it is not actively operating to divert the optical path of electromagnetic beam 28, and so in FIG. 23A, a portion of reflected electromagnetic beam 29 is shown propagating from transfer optical path 16 to the confocal detection assembly 14, thereby rendering the imaging system of the laser surgery system 10 operable. This may be referred to as an "imaging mode" of laser surgery system 100.

When operating according to the embodiment of FIG. 23A, the electromagnetic beam is preferably configured so as to not modify tissue. For example, the electromagnetic beam can be attenuated or otherwise modified to have an energy level below a threshold level for tissue modification.

Alternatively, the electromagnetic beam can be configured to modify tissue even in the imaging mode.

In a preferred embodiment of an imaging mode, a portion of the electromagnetic beam 28 is reflected by eye tissue at the focal point and propagates along the optical bath back to the confocal detection assembly 14. Specifically, a reflected portion 29 of the electromagnetic beam 28 travels back through the patient interface device 22, back through the objective lens assembly 20, back through (and de-scanned by) the scanning assembly 15, back through the transfer optical path 15, and to the confocal detection assembly 14. In many embodiments, and as will be discussed further herein, the reflected portion 29 of the electromagnetic beam 28 that travels back to the confocal detection assembly confocal detection assembly is directed to be incident upon a sensor that generates an intensity signal indicative of intensity of the incident portion of the electromagnetic beam. The intensity signal, coupled with associated scanning of the focal point within the eye, can be processed in conjunction with the parameters of the scanning to, for example, image/locate structures of the eye, such as the anterior surface of the cornea, the posterior surface of the cornea, the iris, the anterior surface of the lens capsule, and the posterior surface of the lens capsule.

Transfer optical path 17 generally comprises one or more optical elements that guide beam 28 from the confocal detection assembly 14 or the confocal bypass assembly 15 to the scanning assembly 18. It should be noted that while transfer optical path 17 is shown as a separate component of the laser surgical system 10 of FIG. 23A, the transfer optical path 17 is optional. In other embodiments transfer optical path 17 may serve a variety of other function. For example, in another embodiment, transfer optical path 17 may comprise or be substituted by a free-floating mechanism 16 described in connection with the embodiments of FIGS. 1 and 2.

FIG. 23B schematically illustrates the laser surgery system 11 of FIG. 23A when the confocal bypass assembly 15 is placed in the optical path of electromagnetic beam 28. In FIG. 23B, the confocal bypass assembly 15 is operable to reversibly divert the optical path of electromagnetic beam 28 along an alternative optical path (i.e., a diversion optical path) that diverts the beam 28 around at least an optical element (not shown) of the confocal detection assembly 14 such that a reflected portion of electromagnetic beam 28 is not diverted to a sensor in the confocal detection assembly 30. In the embodiment of FIG. 23B, the confocal bypass assembly 15 is represented in a state where it is actively operating to divert the optical path of electromagnetic beam 28, and so in FIG. 23B, the electromagnetic beam 28 is shown propagating from laser assembly 20 along an optical path through the confocal bypass assembly 15 and around the optical element (not shown) of the confocal bypass assembly 14 such that no portion of electromagnetic beam 28 is directed to a sensor (detector) of the confocal detection assembly 14. This may be referred to herein as a "non-imaging mode" or alternatively, as a "treatment mode" of laser surgery system 10.

In many embodiments of the treatment mode of FIG. 23B, the beam 28 emitted by the laser assembly 20 propagates along a fixed optical path through the confocal bypass assembly 15 to the transfer optical path 17. Upon reaching the transfer optical path 17, the beam 28 propagates through the remaining laser surgical system in a manner that is the same or similar to the embodiment of FIG. 23A. Specifically, beam 28 travels along transfer optical path 17, is delivered in turn to the scanning assembly 18 and propagates through the objective lens assembly 20, through the interface device 22, and to the patient 24 as described with respect to FIG. 23A.

It should be noted that, in the embodiment of FIG. 23B, a portion of the electromagnetic beam 28 may be reflected by patient tissue at the focal point and propagate along the optical path back along the optical path by which it was delivered. Specifically, a reflected portion of the electromagnetic beam 28 travels back through the patient interface device 22, back through the objective lens assembly 20, back through (and de-scanned by) the scanning assembly 18, and back through the transfer optical path 17. However, the reflected beam enters the confocal bypass assembly 15, which again diverts the optical path of electromagnetic beam 28 around the at least one optical element of the confocal detection assembly 14 along the diversion optical path such that the reflected light is not detected by the confocal detection assembly 14.

When operating in the treatment mode, the direction and position of beam 28 is preferably the same or substantially the same at the entry of and at the exit from the diversion optical path, in a plane transverse to the direction of propagation of the electromagnetic beam. The direction and position of beam 28 is deemed substantially the same at the entry of and at the exit from the diversion optical path in a plane transverse to the direction of propagation of the electromagnetic beam so long as the beam properties are sufficient to meet the system level targeting specification.

Further, the direction and position of beam 28 at the exit from the diversion optical path of confocal bypass assembly 14 in the treatment mode is the same or substantially the same as the direction and position of beam 28 at the same position in the optical path in imaging mode in a plane transverse to the direction of propagation of the electromagnetic beams 28.

When operating in a treatment mode, the electromagnetic beam 28 is preferably configured so as to be capable of modifying tissue. For example, the electromagnetic beam preferably has an energy level above a threshold level for tissue modification.

Figure 24:
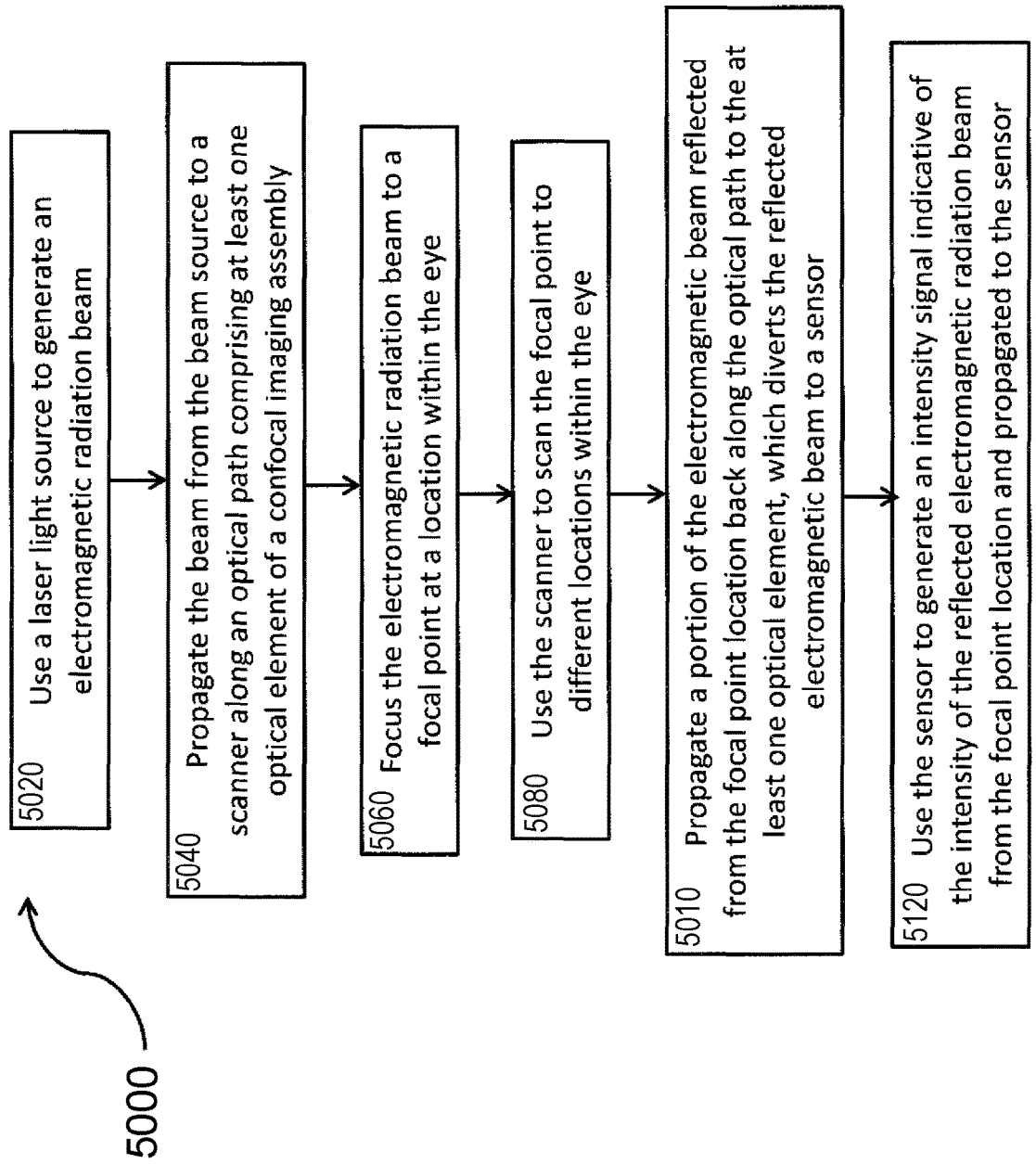
FIG. 24 is a simplified block diagram of acts of a method according to many embodiments, in which the laser surgery system is used to image one or more portions of a target tissue, such as a patient's eye.

FIG. 24 is a simplified block diagram of acts of a process 5000 according to a method of imaging an eye in accordance with an imaging mode. Any suitable device, assembly, and/or system, such as described herein, can be used to practice the process 5000. The process 5000 includes using a beam source to generate an electromagnetic beam (Action Block 5020) and propagating the electromagnetic beam from the beam source to a scanner along an optical path comprising at least one optical element of a confocal imaging assembly (Action Block 5040). The process 5000 includes focusing the electromagnetic beam to a focal point at a location within the eye (Action Block 5060). The process 5000 includes using the scanner to scan the focal point to different locations within the eye (Action Block 5080). The process 5000 includes propagating a portion of the electromagnetic beam reflected from the focal point location back along the optical path to the at least one optical element, which diverts the reflected electromagnetic radiation to a sensor (Action Block 5100). The process 5000 includes using the sensor to generate an intensity signal indicative of the intensity of the reflected electromagnetic beam from the focal point location and propagated to the sensor (step 5120).

Figure 25:
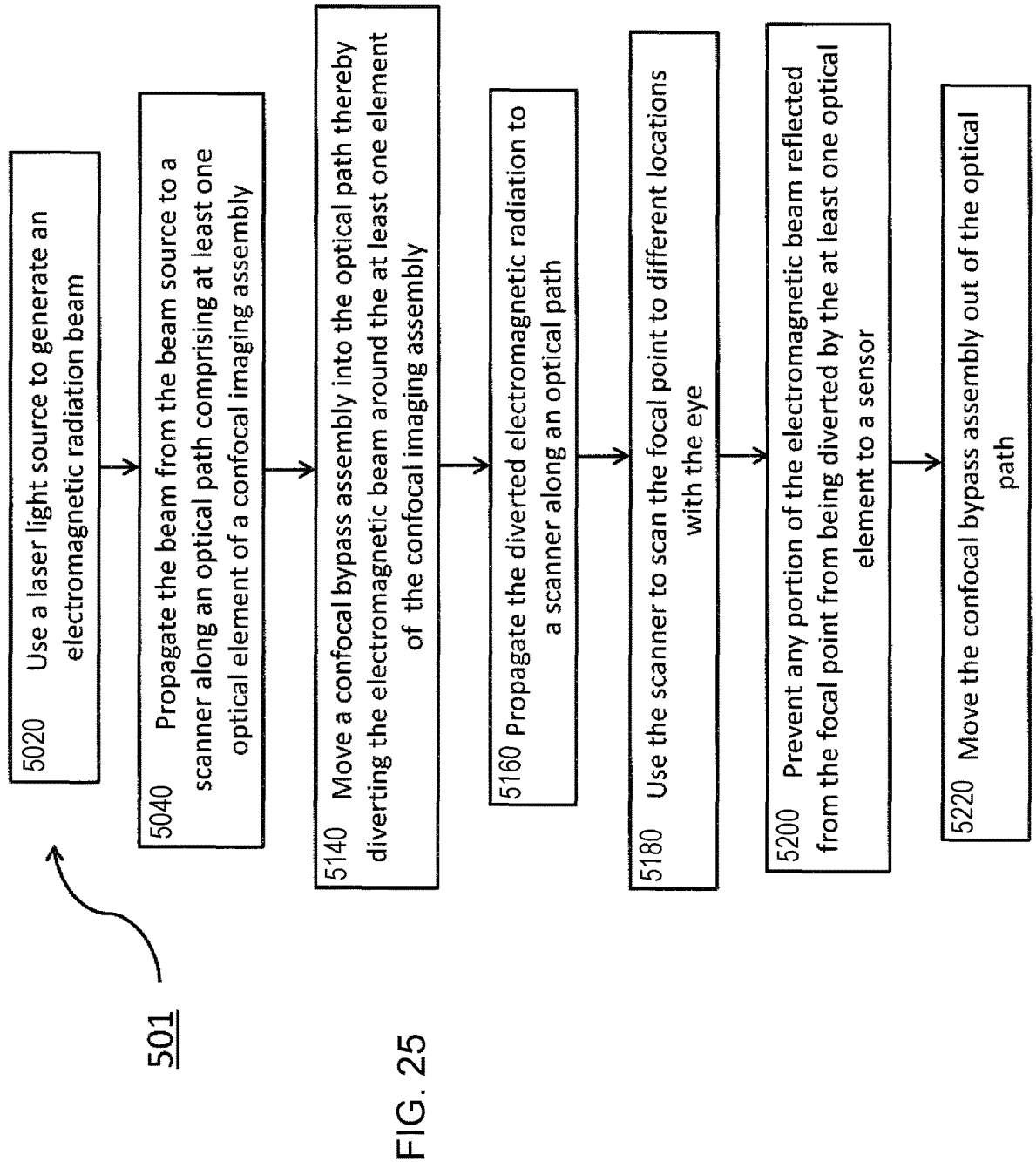
FIG. 25 is as simplified block diagram of acts according to many embodiments, in which the laser surgery system is used to modify target tissue in a patient's eye.

FIG. 25 is a process 501 for reversibly switching operation from an imaging mode to a non-imaging mode may include using a laser source to generate an electromagnetic beam (Action Block 5020), propagating the electromagnetic beam from the beam source along an optical path comprising at least one optical element of a confocal imaging assembly (Action Block 5040), moving a confocal bypass assembly into the optical path thereby diverting the electromagnetic beam around the at least one element of the confocal imaging assembly (Action Block 5140), propagating the diverted electromagnetic radiation to a scanner (Action Block 5160), using the scanner to scan the focal point to different locations with the eye (Action Block 5180) and, preventing any portion of the electromagnetic beam reflected from the focal point location from being diverted by the at least one optical element to a sensor of the confocal bypass assembly (Action Block 5200) and moving the confocal bypass assembly out of the optical path (Action Block 5220).

Figure 26:
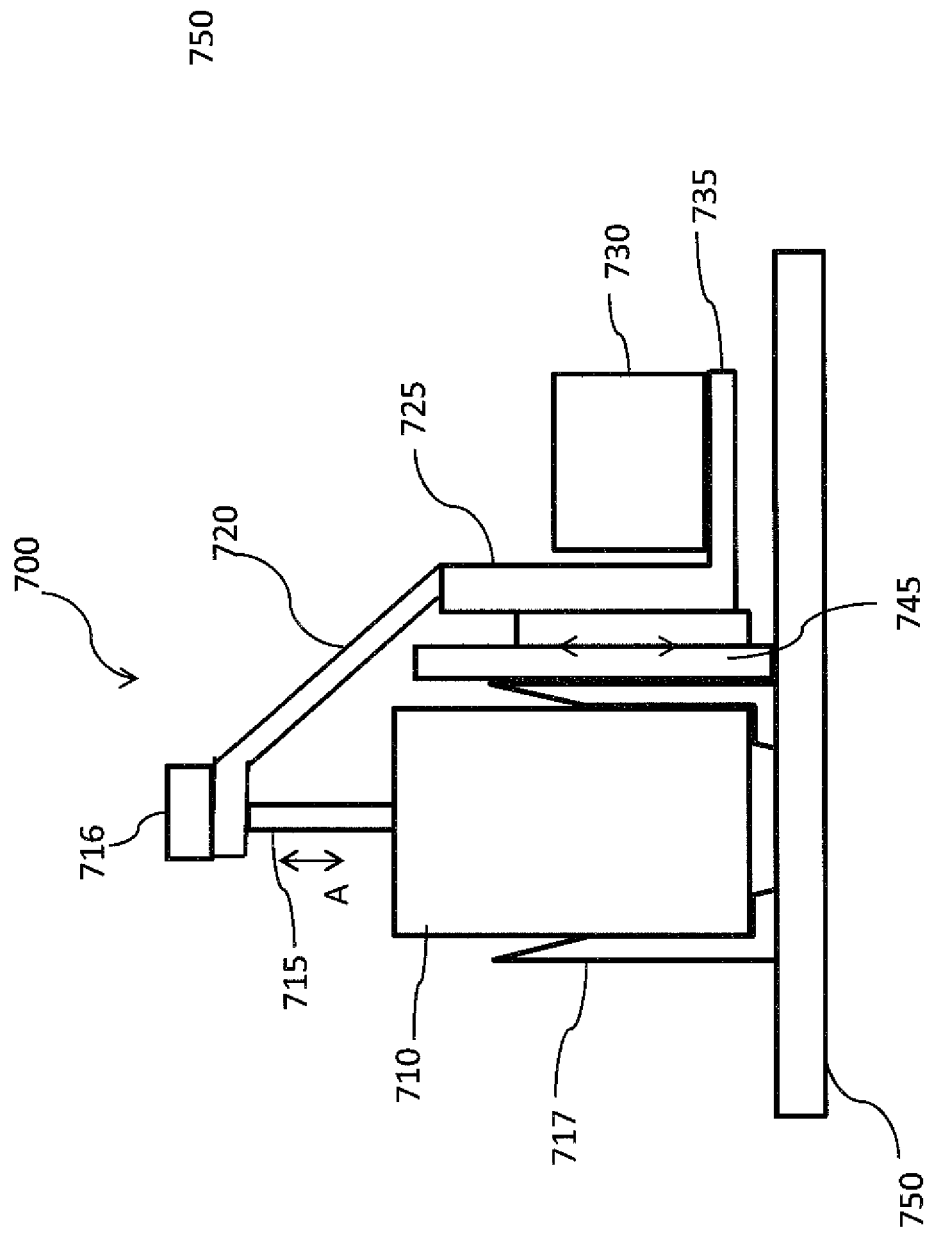
FIG. 26 is a schematic diagram showing an illustrative embodiment of a confocal bypass assembly.

One embodiment of a confocal bypass assembly 700 is shown in FIG. 26. The confocal bypass assembly 700 includes a push solenoid 710 having an arm 715 that is fixably connected to one end of actuation arm 720 and is secured in place by a tip 716. In the embodiment of FIG. 26 push solenoid 710 is held in a frame 417, which is fixably mounted to base 750. Arm 715 of the push solenoid reversibly moves in the "A" direction. The other end of actuation arm 720 is connected to a carrier 725, which has a platform 735 on which the bypass optical element 730 is mounted. The confocal bypass assembly 700 may also include a slide member 745 having 2 sides that move relative to teach other along the "A" direction. In the embodiment of FIG. 26, the carrier 725 is fixably connected to one side of slide 745, and frame 717 holding push solenoid 710 is fixably connected the other side of slide 745 such that the push solenoid and the carrier move in the direction "A" relative to each other.

In operation, in the embodiment of FIG. 26, arm 715 of push solenoid 410 moves in the direction "A" away from the body of the push solenoid, and the movement of the arm 715 is communicated to the carrier 725 via actuation arm 720 and results in the movement of carrier 725 in the same "A" direction relative to the body of the push solenoid by action of the slide 745. In this way, the bypass optical element 730 is raised into the optical path of the electromagnetic path of the electromagnetic beam. The bypass optical element 730 may then be removed from the optical path by moving the arm 715 of the push solenoid 710, under control of control electronics towards the body of the push solenoid 710, thus reversing the movement of bypass optical element 735 and thus moving it out of the optical path of the beam 28.

The confocal bypass assembly generally includes one or more optical elements, referred to herein as bypass optical element optical elements, which, when inserted into the optical path of the electromagnetic beam, divert the beam around at least one optical element of the confocal detection assembly. The confocal bypass assembly thus establishes an alternative optical path, referred to herein as a diversion optical path, around the one or more optical elements of the confocal detection assembly. The confocal bypass assembly should thus be configured to reversibly move one or more bypass optical elements into and out of the optical path of the electromagnetic beam under control of system control electronics when an imaging mode or treatment mode is desired. Those of ordinary skill in the art will recognize that the reversible movement of optical elements into and out of an optical path thus may be accomplished in numerous ways.

In a preferred embodiment, the bypass optical element is a bypass prism designed to divert beam 28 around an optical element of the confocal detection assembly by a series of reflections within the bypass prism. In one embodiment, the bypass prism is comprised of two rhomboid prisms, which may optionally be joined together to form a single integrated unit. Alternatively, a set of mirrors can be used to divert the beam around the optical element of the confocal detection assembly.

Figure 27B:
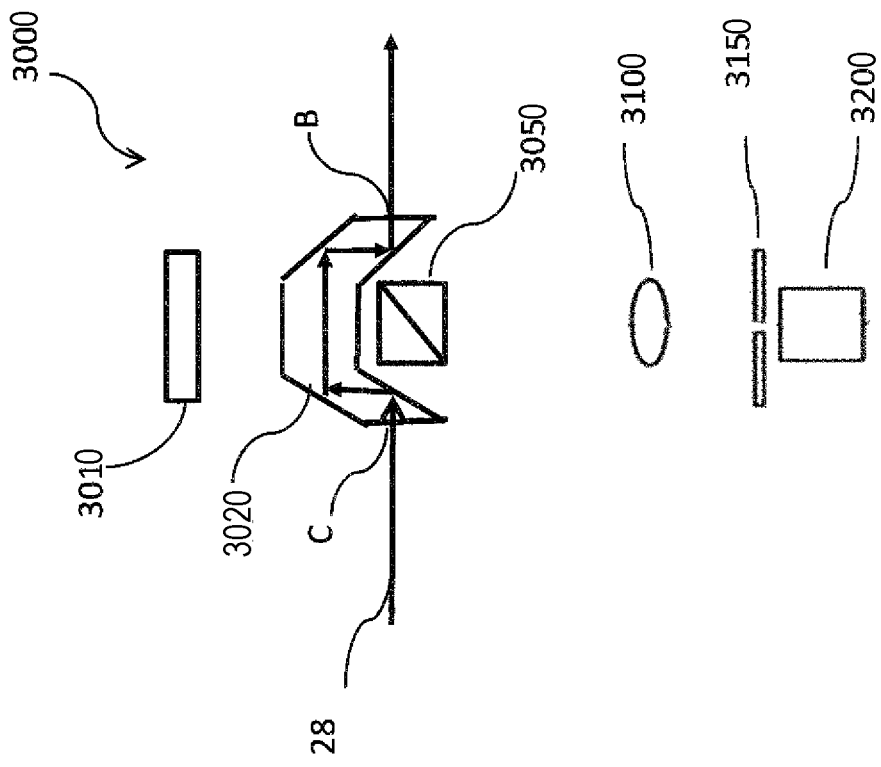
FIG. 27A and FIG. 27B are schematic diagrams illustrating an embodiment, in which the confocal bypass assembly includes a bypass prism, and wherein the optical path in an imaging mode is illustrated in FIG. 27A, and a diversion optical path in a non-imaging mode (i.e. treatment mode) is illustrated in FIG. 27B.
Figure 27A:
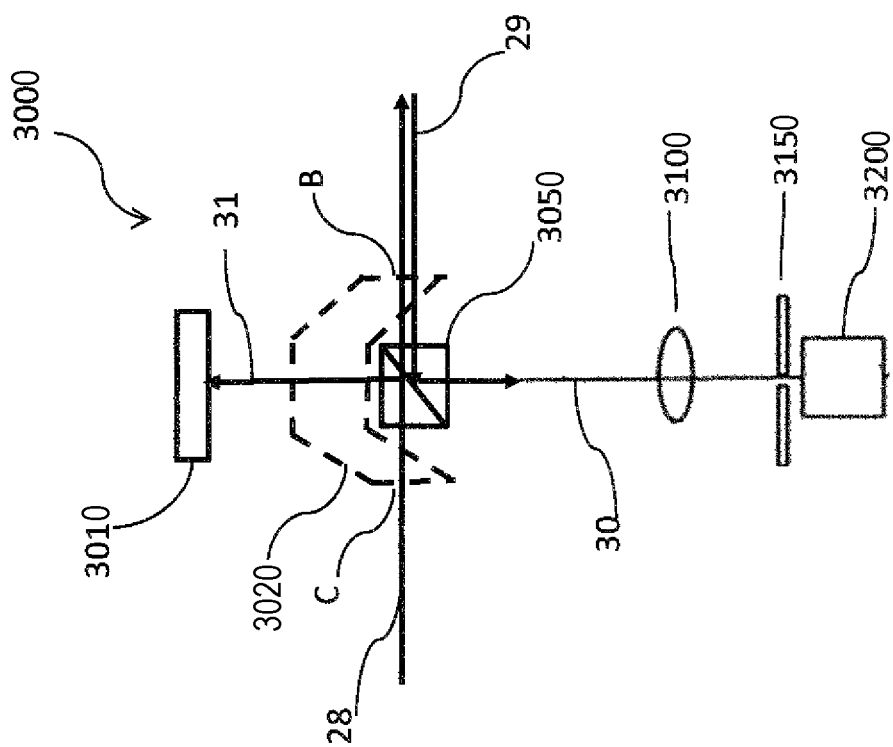

FIGS. 27A and 27B show certain aspects of a laser surgical system showing the operation of a confocal bypass assembly comprising a bypass prism as the bypass optical element. In FIG. 27A, the bypass element is below the optical beam 28 and is shown in dashed lines to demonstrate its relative position to the confocal detection assembly when viewed from above. Since the confocal bypass assembly is not in the optical path in FIG. 27A, FIG. 27A shows a mode of the system wherein imaging is enabled. In FIG. 27A, electromagnetic beam 28 passes through a beam-splitter (BS) 3050 and is then delivered to the scanner and objective which focuses the light on the target tissue (not shown). Returned scattered light 29 from the target tissue is again directed through a beam-splitter 3050 and is directed to a focusing lens 3100, a pinhole aperture 3150 and a sensor (photodetector) 3200.

Preferably, the beam-splitter 3050 is configured to attenuate the beam 28 such that the beam-splitter 3050 transmits only a fraction of the electromagnetic beam 28 to the target resulting in a high power rejected beam 31 directed to dump 3010 as the remainder of electromagnetic beam 28 propagates from the light source to the scanner. Preferably, the beam-splitter transmits less than 20% of the incident light, more preferably less than 90%, more preferably less than 95% and more preferably 99% or less of the incident light. Further, the beam-splitter 3100 is configured to have a high reflectivity of the returned scattered light 29 directed to the sensor 3200. Preferably, the beam-splitter reflects 80% of the reflected light, more preferably 90% of the reflected light, more preferably 95% of the reflected light, and more preferably, 99% or more of the reflected light. Thus, in the imaging mode of FIG. 27A, beam 28 exiting the beam-splitter 3050 is attenuated and optimized for imaging. Beam 28 exiting the beam-splitter 3050 need not be sufficient to modify the target tissue, and in a preferred embodiment beam 28 is not configured to modify the target tissue as it exits beam-splitter 3050 and propagates toward the target tissue.

Preferably, beam-splitter 3050 is fixed in the optical path of beam 28 and is not a polarizing beam-splitter (i.e., it does not operate to split a beam based on a polarization property of the reflected light). More preferably, beam-splitter 3050 is beam-splitter prism.

FIG. 27B shows a bypass prism 3020 inserted into the optical path adjacent the beam-splitter 3050. When the bypass prism 3020 is inserted in the optical path of beam 28, as shown in FIG. 27B, the beam 28 enters the diversion optical path at point C and is directed around the beam-splitter by bypass prism 3020 by undergoing a series of reflections within the body of bypass prism 3020 that form the diversion optical path before exiting the bypass prism at point B. The precise number of reflections needed to establish the optical path is not necessarily limited; however, the total number of reflections should be an even number so that the position, direction and orientation of the beam 28 remain the same at the point it enters the bypass optical path (point C in FIG. 27B) and the point it exits the optical path (Point B in FIG. 27B). In FIG. 27B, a series of 4 reflections are shown and each reflection angle is represented as being at right angles, but, while preferred, neither of these is required. Those of ordinary skill will recognize that the diversion optical path may be constructed with various optical elements to achieve an even number of reflections along the diversion optical path using various reflection angles.

Preferably, the direction and orientation of electromagnetic beam 28 remain the same or substantially the same at the point it exits the bypass optical path (point B in FIG. 27B), and the same position in the optical path of the imaging mode (Point B in FIG. 27A). "Substantially the same" means that the beam properties are sufficient to meet the system level targeting specification.

By diverting beam 28 around beam-splitter 3050, the power attenuation of the beam-splitter prism 3000 is avoided and the required boresight accuracy relative to the imaging light path, and the laser beam is directed toward the microscope objective to focus on the target. Preferably, in the treatment mode of FIG. 27B, the electromagnetic beam is configured to modify the target tissue.

Figure 28A:
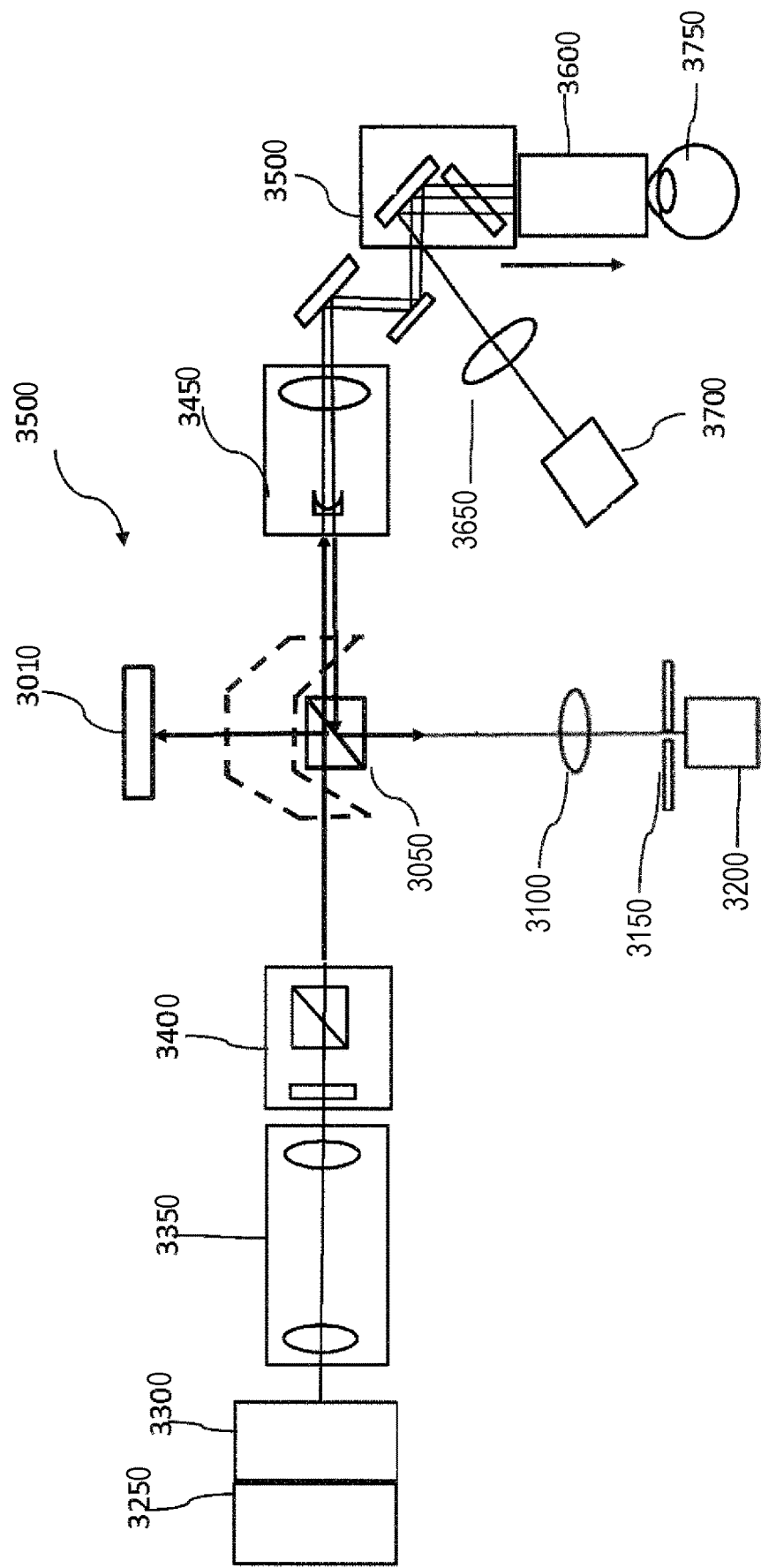
FIG. 28A and FIG. 28B are schematic diagrams illustrating an embodiment of a laser surgical system utilizing a bypass prism to switch between an imaging mode (FIG. 28A) and a non-imaging mode (FIG. 28B).
Figure 28B:
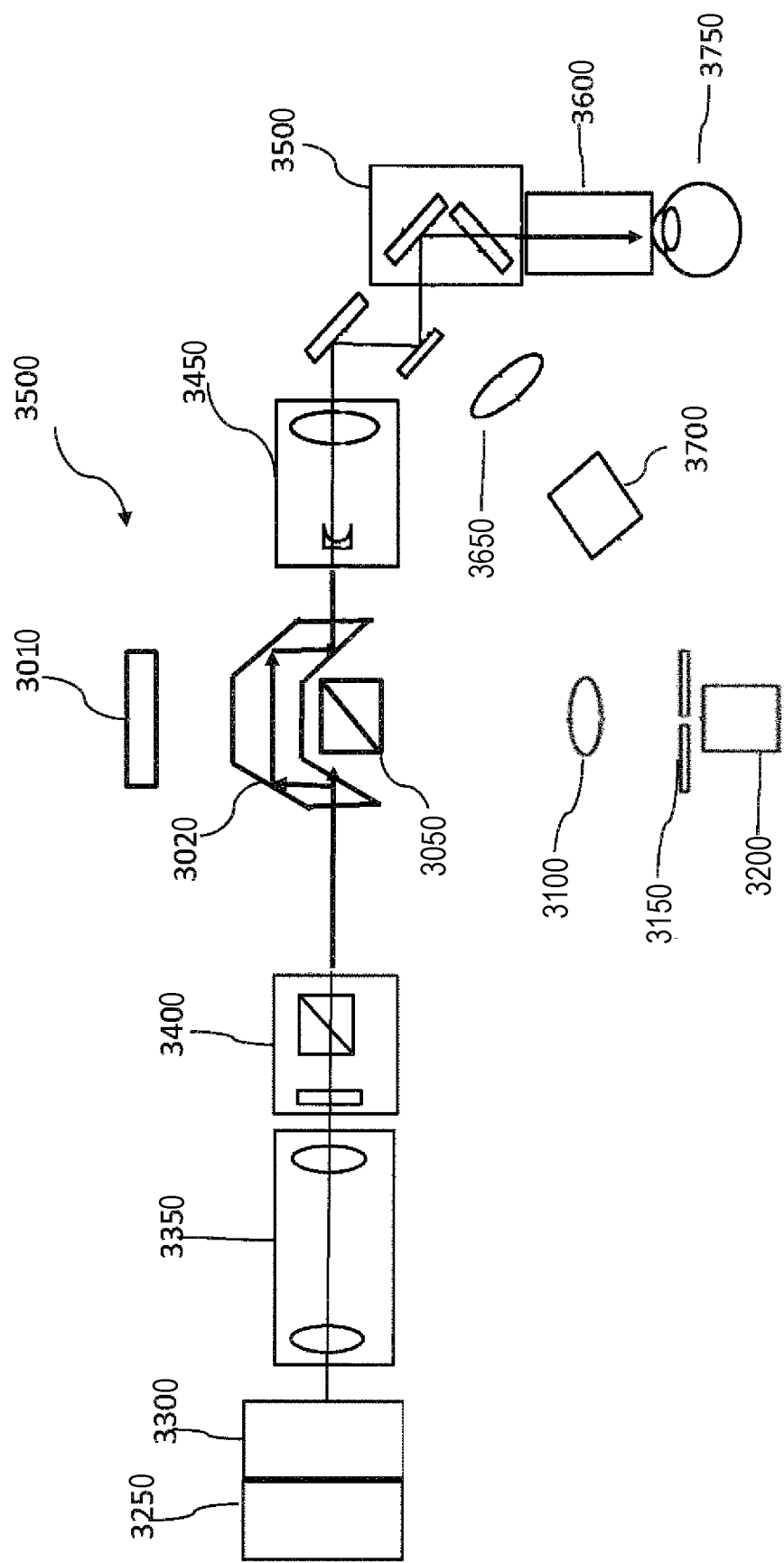

One implementation of a system using a bypass prism and a confocal bypass assembly is shown in FIG. 28A and FIG. 28B. The system 3500 includes control electronics 3250, a light source 3300, an optional attenuator 3400, a beam expander 3350, an optional optical variable beam attenuator 3400, a separate focus lens combination 3450 and a scanning means 3500. The light beam 3280 of light source 3300 is propagated though beam-splitter and is focused through lens 3600 to its target location 3750. Additionally, the reflected light from the target structure 3750 is again directed through the beam-splitter 3050 and diverted to lens 3100. An aperture pinhole 3150 is placed in the focal spot of reflected beam as a conjugate of the laser beam focus in target structure 3750. The intensity of the reflected electromagnetic beam through beam aperture 3150 is detected and converted to an electrical signal which can be read by the control unit 3250. In the embodiment of FIG. 28A and FIG. 28B, an image of the treated area is imaged by lens 3650 on an image capture device 3700 which can be a CCD or a CMOS camera. Also this signal is transmitted to control unit 3250.

Figure 29:
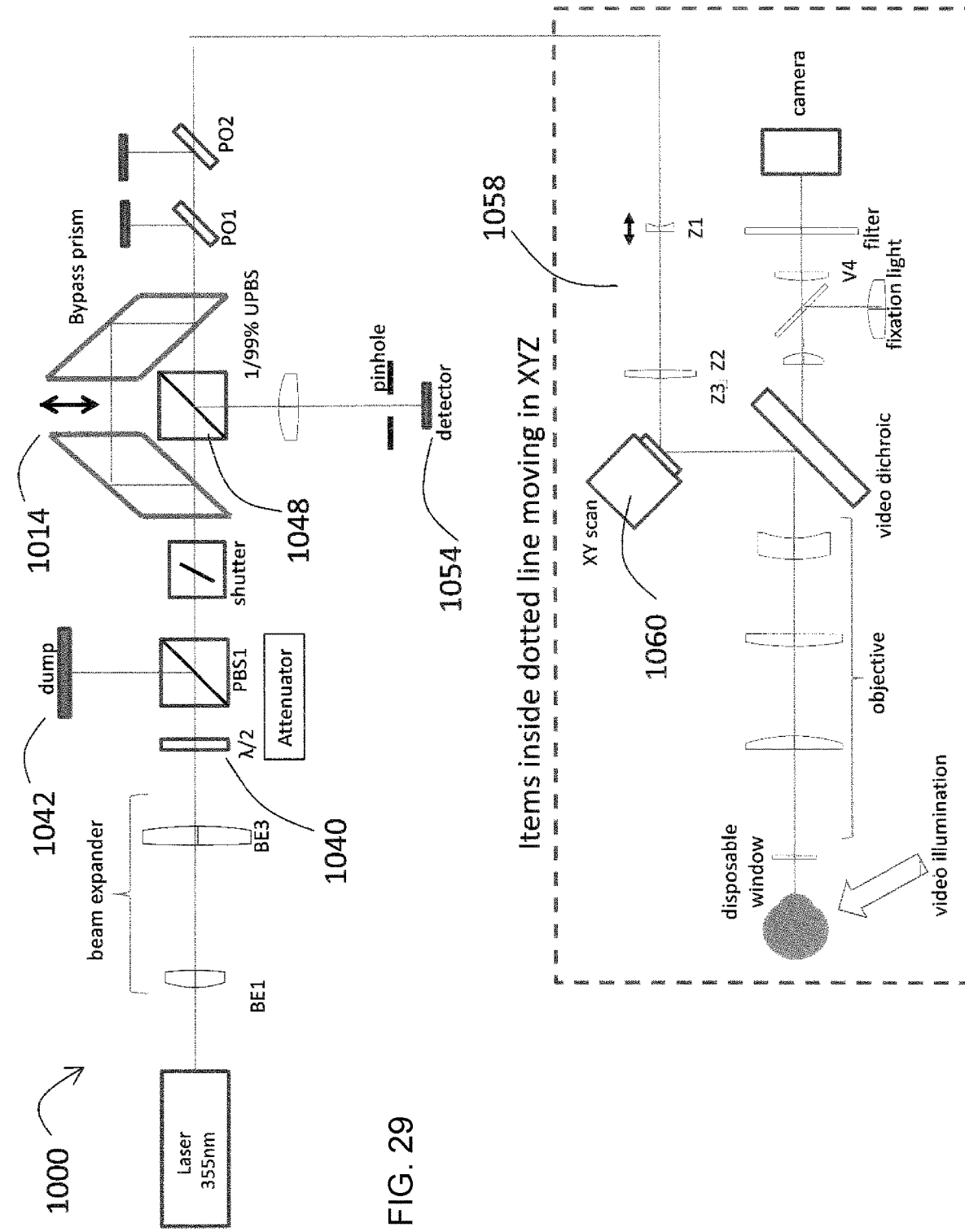
FIG. 29 is another schematic diagram of the laser surgery system of FIG. 1, according to an embodiment of the invention.

FIG. 29 illustrates a laser surgery system 1000 used for imaging and treating an eye according to another embodiment that includes a bypass assembly. The laser surgery system 1000 includes elements as described in the laser surgery system 10, as shown in FIG. 2. The laser surgery system 1000 further may manage the different power levels required for imaging at low levels and treating at high levels and at the same time switching between imaging and treatment optical path. At the same time, this should be done in a manner which makes the whole assembly insensitive to mechanical design choices. The laser surgery system 1000 may further include imaging ocular structures in a low power imaging mode to determine the location of reference surfaces and then using this information to treat in a second high power treatment mode.

In an embodiment, the laser surgery system 1000 does not make use of a polarizing element to avoid issues which arise with the polarization rotation of the cornea. This is achieved by utilizing a high ratio non-polarizing beam-splitter 1048 to separate said beams for imaging. A high splitting ratio of said beam-splitter 1048 acts in two ways: first, reduction of incident power to a regimen where it can be utilized for safe imaging; and second, acting as a high reflector for the light from imaged structure. A second moveable optical element 1014 is inserted in the beam path to bypass the first high contrast beam-splitter 1048 and redirect all available laser light around said splitter 1048 to enable treatment at high energy levels. This bypass element 1014 may have single or multiple prisms or mirrors. The advantage of using this embodiment lays in its high tolerance to mechanical variations to the moving of the bypass element 1014. One could also just move the high contrast beam-splitter 1048, but the mechanical tolerances to enable this would be quite high. All tolerances are relaxed by an order of magnitude by utilizing the bypass assembly 1014.

In an embodiment, the laser surgery system 1000 focuses a first electromagnetic radiation beam to a focal point at a location in the eye, wherein the first electromagnetic radiation beam has a first polarization. The laser surgery system 1000 may further focus a second electromagnetic radiation beam to a focal point at the location in the eye, wherein the second electromagnetic radiation beam has a second polarization state which is different from the first polarization state. The laser surgery system 1000 may further generate a first intensity signal indicative of an intensity of electromagnetic radiation reflected from the eye in response to the step of focusing the first electromagnetic radiation beam, and generate a second intensity signal indicative of an intensity of electromagnetic radiation reflected from the eye in response to the step of focusing the second electromagnetic radiation beam. One or more images of the eye may then be generated with the first and second intensity signals.

In an embodiment, the first and second electromagnetic radiation beams may be focused using a beam scanner. The laser surgery system 1000 may further scan the focal point of the first electromagnetic radiation beam to a plurality of different locations in a first region of the eye and may scan the focal point of the second electromagnetic radiation beam to the plurality of different locations in a second region of the eye. A first intensity profile may be generated that is indicative of intensities of electromagnetic radiation reflected from the eye in response to the step of scanning the focal point of the first electromagnetic radiation beam. A second intensity profile may be generated that is indicative of intensities of electromagnetic radiation reflected from the eye in response to the step of scanning the focal point of the second electromagnetic radiation beam. In an embodiment, one image of the eye is generated using the first and second intensity profiles. For example, in imaging a cornea of an eye, the anterior surface of the cornea may be identified using the first intensity profile and the posterior surface of the cornea may be identified using at least a portion of the second intensity profile. In another embodiment, the first electromagnetic radiation beam has a first polarization; the second electromagnetic radiation beam has a second polarization different than the first polarization.

A beam scanner may include an XY-scan device 1060 that is configured to deflect the first and second electromagnetic radiation beams in two dimensions transverse to a propagation of first and second electromagnetic radiation beams. The focal point of the first and second electromagnetic radiation beam may be scanned in the two dimensions using the XY-scan device 1060 according to some embodiments and may thereby provide an image with at least two dimensions.

The beam scanner may further include a Z-scan device 1058 that is configured to vary a convergence depth of the beam within the eye. In some embodiments, the Z-scan device 1058 may vary a convergence angle of the beam. The focal point of the first and second electromagnetic radiation beams may then be scanned in the three dimensions using the XY-scan device 1060 and the Z-scan device 1058. Accordingly, the image of the eye may be three dimensional according to some embodiments.

In an embodiment, the first and second intensity signals may be generated by a sensor 1054. The sensor 1054 may be a confocal sensor and the laser surgery system 1000 may further block reflected electromagnetic radiation from eye locations other than the location of the focal point of the first and second electromagnetic radiation beams from reaching the sensor 1054.

In an embodiment, the first electromagnetic radiation beam may be generated by passing an electromagnetic radiation beam through a wave plate in a first position, e.g., wave plate 56 as shown in FIG. 2, so as to polarize the electromagnetic radiation beam with the first polarization. The wave plate may be rotated by an angle to a second position. The second electromagnetic radiation beam may be generated by passing the electromagnetic radiation beam through the wave plate in the second position. This wave plate may be a one-quarter wave plate. In some embodiments, the wave plate may be rotated by an acute angle for generating the second electromagnetic radiation beam. In some embodiments, the wave plate may be rotated ninety degrees for generating the second electromagnetic radiation beam. In some embodiments, the first and second electromagnetic radiation beams may be polarized with the first and second polarizations by using a Faraday rotator, or a rotating beam-splitter.

In response to the step of focusing the first electromagnetic radiation beam, the electromagnetic radiation reflected from the eye passes through the wave plate in the first position. Further, electromagnetic radiation reflected from the eye in response to the step of focusing the second electromagnetic radiation beam may be passed through the wave plate in the second position.

In another embodiment, the laser surgery system 1000 may scan a focal point of a first electromagnetic radiation beam to a plurality of locations in the eye, with the first electromagnetic radiation beam having a first polarization. The laser surgery system 1000 may further scan a focal point of a second electromagnetic radiation beam to at least a portion of the plurality of locations in the eye, with the second electromagnetic radiation beam having a second polarization different than the first polarization. A first intensity profile indicative of an intensity of electromagnetic radiation reflected from the eye may be generated in response to the step of scanning the first electromagnetic radiation beam. And a second intensity profile indicative of an intensity of electromagnetic radiation reflected from the eye may be generated in response to the step of scanning the second electromagnetic radiation beam. An image of the eye may be produced using the first and second intensity profiles.

Figure 31:
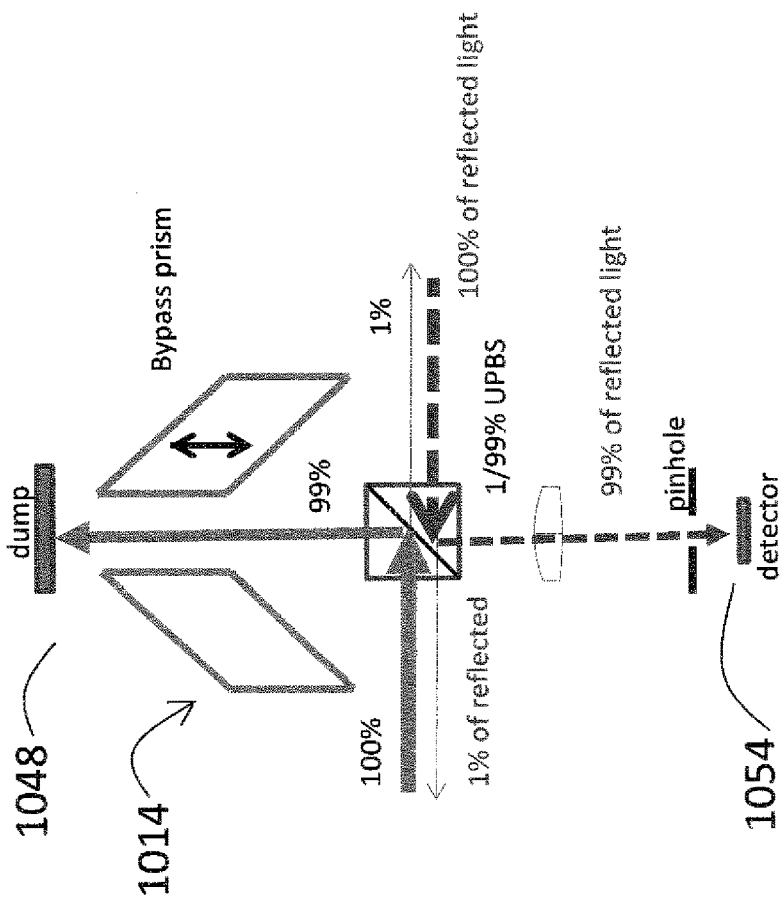
FIG. 31 is another schematic diagram of a bypass element of the laser surgery system of FIG. 23 according to an embodiment of the invention.
Figure 30:
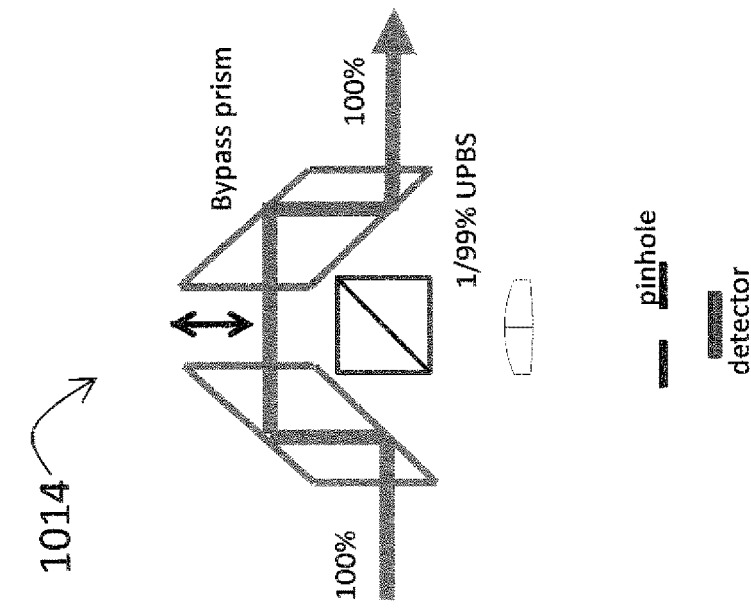
FIG. 30 is a schematic diagram of a bypass element of the laser surgery system of FIG. 23 according to an embodiment of the invention.

FIG. 30 illustrates, according to an embodiment, the bypass assembly 1014 as used in a treatment mode. As shown, the electromagnetic radiation beam is directed toward the bypass mirrors or prisms of the bypass assembly 1014, and bypasses the beam-splitter 1048. As a result, 100% of the electromagnetic radiation beam passes downstream, providing a high power level for treatment mode. FIG. 31 illustrates the system 1000 as used in imaging mode, according to an embodiment. In this embodiment, the electromagnetic radiation beam is directed toward the non-polarized beam-splitter and dump 1048, and bypasses the bypass assembly 1014. The non-polarized beam-splitter is a 1/99% beam-splitter. As a result, 99% of the electromagnetic radiation beam is directed toward the dump, and 1% of the electromagnetic radiation beam passes downstream toward the eye of the patient, resulting in a low power level for imaging. After reflecting from a focal point in the eye of the patient, a returning reflected portion of the beam is again directed by the beam-splitter. As a result, 99% of the reflected portion of the beam is directed upon the sensor 1054 for imaging.

Figure 32:
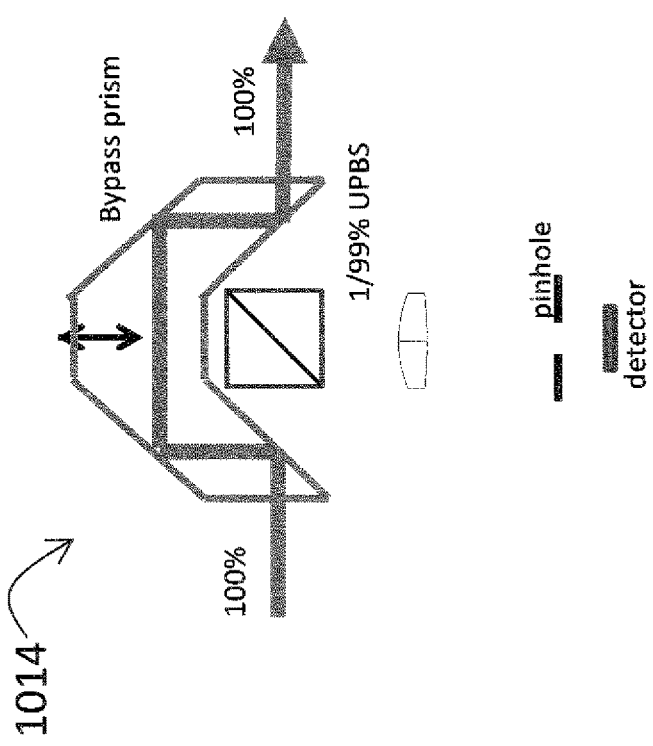
FIG. 32 is another schematic diagram of a bypass element of the laser surgery system of FIG. 23 according to an embodiment of the invention.
Figure 33:
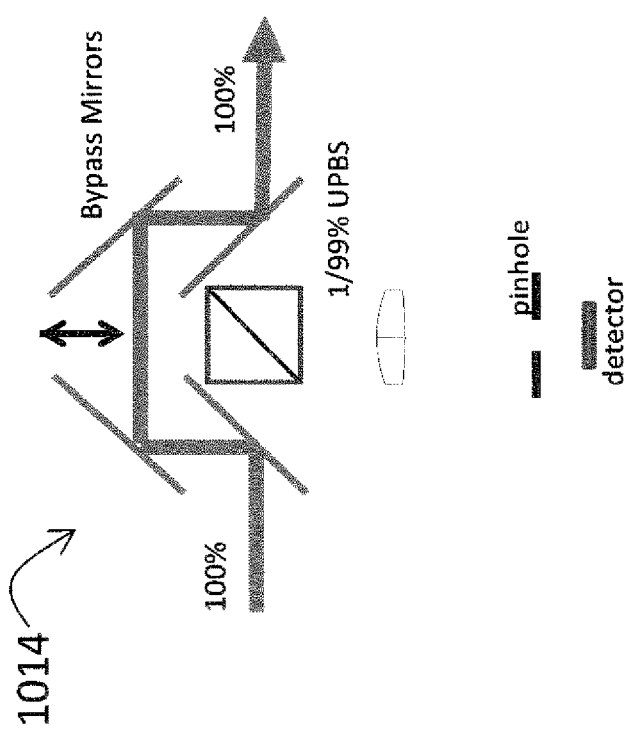
FIG. 33 is another schematic diagram of a bypass element of the laser surgery system of FIG. 23 according to an embodiment of the invention.

It should be noted that other embodiments of the bypass assembly 1014 having single or multiple mirrors or prisms may be used. For example, FIGS. 32 and 33 illustrate other embodiments of the bypass assembly 1014 in treatment mode. In FIG. 32, the two mirrors or prisms positioned at an angle are further connected with a third prism. In FIG. 33, the bypass assembly 1014 utilizes four mirrors or prisms as shown.

Figure 34:
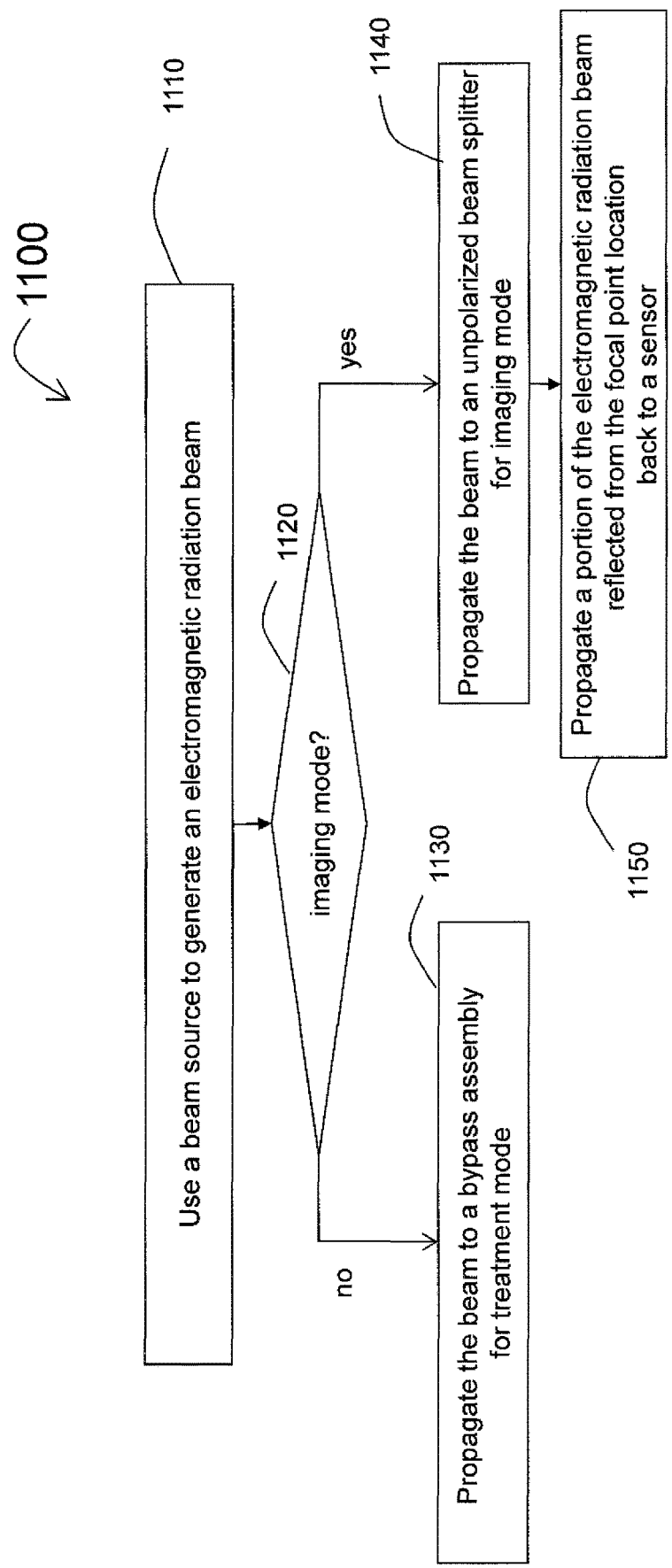
FIG. 34 is a simplified process for imaging and treating an eye according to an embodiment of the invention.

FIG. 34 shows a process 1100 of the laser surgery system 1000 for imaging and treating an eye, e.g., a cornea, according to an embodiment of the invention. The laser surgery system 1000 uses a beam source to generate an electromagnetic radiation beam (Action Block 1110). If the system 1000 is in treatment mode (Decision Block 1120), the system 1000 propagates the electromagnetic radiation beam to a bypass assembly 1014 (Action Block 1130). If the system 1000 is in imaging mode (Decision Block 1120), the system 1000 propagates the electromagnetic radiation beam to a beam-splitter and dump 1048 (Action Block 1140). It is noted that the beam-splitter need only be substantially unpolarized in the returning (i.e. reflected beam). The outgoing (transmitted beam) may already be inherently polarized and the beam-splitter transmission can be either polarization dependent or polarization independent, so long as the correct outgoing beam transmission occurs. In imaging mode, as a portion of the electromagnetic radiation beam is reflected from the focal point location in the eye, the system 1000 propagates a portion of the reflected electromagnetic radiation beam to a sensor 1054 for imaging (Action Block 1150).

Further, while some of the above methods are described as using a wave plate and more specifically a one-quarter wave plate, it should be understood that other variable axis polarization systems may be used. For example, in some embodiments of processes 100 and 400, the laser surgery system 10 may use a spatial light modulator (e.g., a liquid crystal panel), two or more retarding wave plates, a Faraday rotator, a rotating polarizing beam-splitter, and so on.

In some embodiments, knowledge about corneal polarization may be used for other therapeutic applications in which the degree of polarization rotation is an indicator of tissue condition, and could lead to iteration of the planned treatment. For instance, corneal retardance could be an indicator of disease progression such as corneal thinning, or could indicate the strength of corneal tissue, which in turn would be valuable in correctly calculating corneal arcuate incisions, or limbal relaxing incisions used for astigmatic correction.

In many embodiments, one or more measurements of a cornea are used with input parameters to determine locations of incisions of the cornea, such as corneal incisions. The one or more measurements can be obtained in many ways, such as with images used for measuring corneal topography or tomography, or without imaging the eye. One or more additional images can be obtained when the one or more measurements are obtained, and these one or more additional images can be used in combination with the measurements for aligning the measurement coordinates and the cutting coordinates.

In many embodiments, a surface profile of the cornea is measured in one or more of many ways, and may comprise one or more of an anterior corneal surface topography profile, a posterior a corneal surface topography profile, or a corneal thickness profile. In many embodiments, the surface profile comprises a representation of a three dimensional profile and may comprise an extraction of one or more parameters from one or more images, such as an extraction of keratometry values from a corneal topography system or tomography system integrated with the surgical laser. The one or more parameters can be used to determine a tissue treatment pattern on the eye, such as the angular location, depth, arc length and anterior to posterior dimensions of relaxing incisions.

Figure 35:
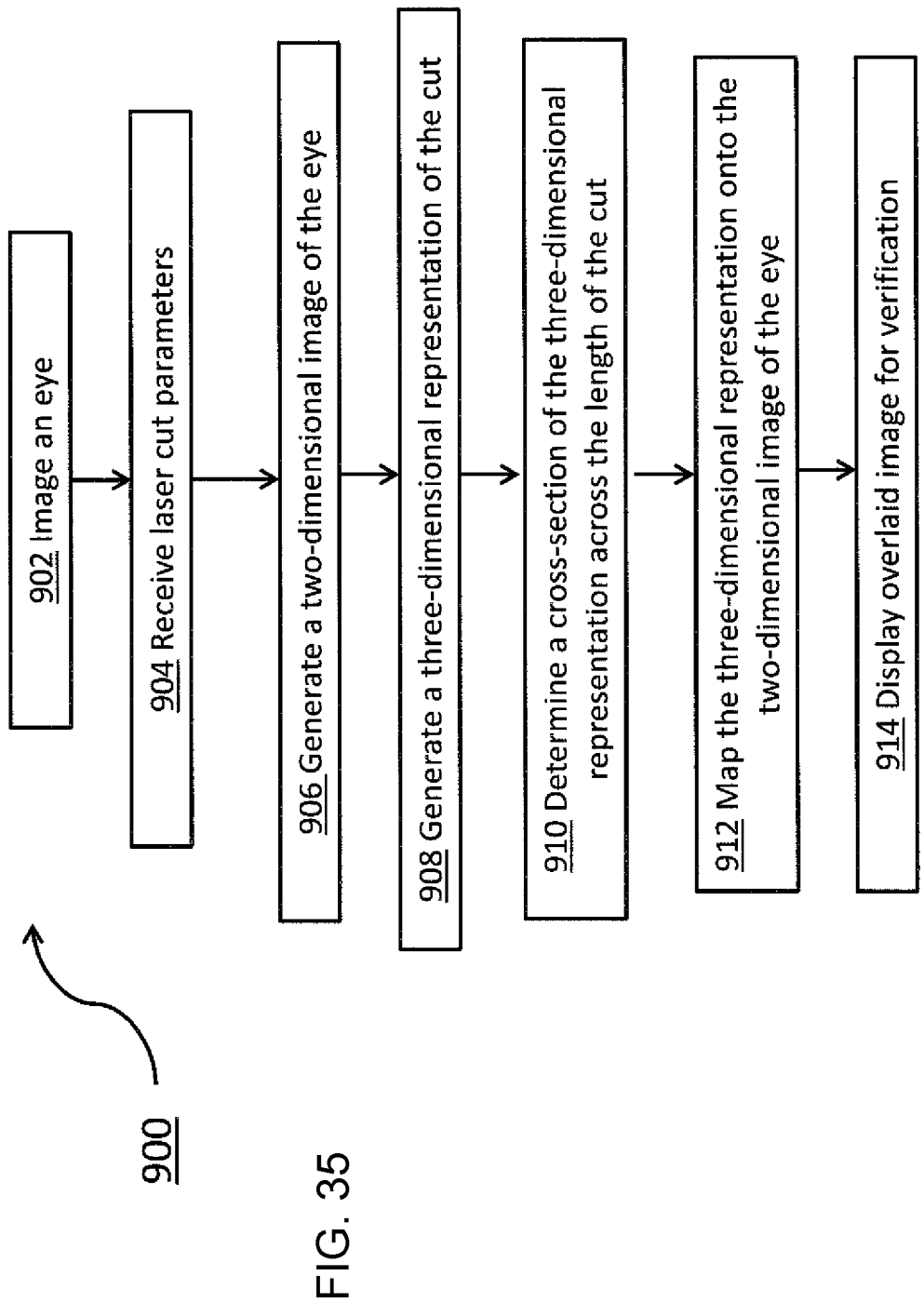
FIG. 35 is a simplified process of imaging an eye with a proposed incision, according to an embodiment of the invention.
Figure 36A:
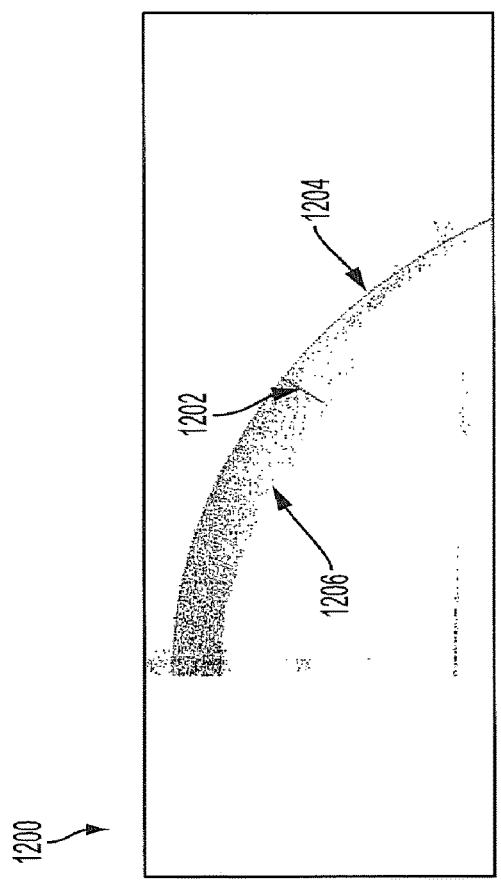
FIGS. 36A and 36B show an exemplary display of an incision review for a cornea of an eye generated according to an embodiment of the invention.
Figure 36B:
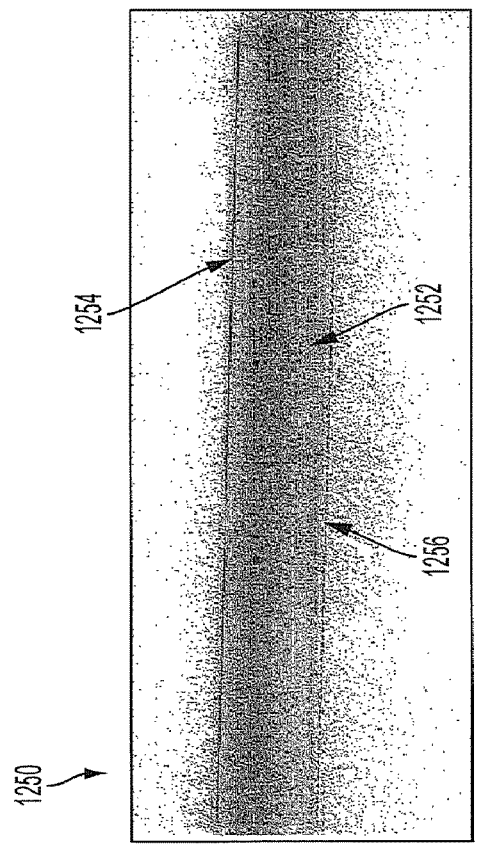

FIG. 35 is a simplified process 900 of imaging an eye with a proposed incision, according to the many embodiments for imaging an eye described herein. FIGS. 36A-36B show an exemplary display of an incision review of a cornea of an eye generated according to an embodiment of the invention. Although FIGS. 35 and 36A-36B are described using an arcuate incision, the laser cut preview images are not limited to arcuate incisions and can be generated for primary and side-port incisions, as well as any other incision in the eye.

The process may start with obtaining an image of the eye as discussed in any of the embodiments herein, such as by a laser surgery system 10 (Action Block 902). A plurality of parameters are then received that define the laser incision (Action Block 904). For instance, the parameters of an arcuate incision cut may include the type of cut, axis (degree), optical zone (mm), length (mm), center method, horizontal spot spacing (µm), vertical spot spacing (µm), pulse energy (µj), anterior density, anterior line distance (µm), central line density, uncut anterior (µm), uncut posterior (µm), and side cut angle (degree). The type of cut may include single, symmetric, asymmetric and toric. The uncut anterior and uncut posterior may also be input as a percentage value and indicate a margin of the cut from the cornea anterior and cornea posterior, respectively. The parameters may be input or predetermined. FIG. 36A illustrates an image 1200 of the cornea including the anterior 1204 and posterior 1206. A preview of an arcuate incision 1202 is overlaid on the cornea image 1200 where the incision 1202 is of the same cross-sectional plane as the cornea image. From FIG. 36A alone, a user is unable to verify that the incision does not penetrate the cornea throughout the entire length of the incision since only one plane of the incision 1202 is shown.

Next, a two-dimensional image of the eye is generated in a plane defined by the intersection of the length and depth of the cut (Action Block 906). In particular, the image is in the plane of the incision axis and an incision length transverse to the incision axis. The image can include the cornea anterior and cornea posterior and may include enhancement to highlight the cornea anterior and cornea posterior, as shown in FIG. 36B and explained in further detail below. Based on the received cut parameters, a three-dimensional representation of the cut is generated such as of a conical surface of an arcuate incision (Action Block 908). From the generated three-dimensional representation of the cut, a three-dimensional cross-section of the conical surface along a length of the cut is determined (Action Block 910). This "along the cut" image is defined as a set of points representing a section of the conical surface including the arcuate incision. In order to display the three-dimensional cross-section on the two-dimensional image of the eye, the "along the cut" image is necessarily distorted, such as by 3D projection, so that the points of the three-dimensional surface are mapped onto the two-dimensional plane of the image (Action Block 912). Alternatively, the set of points in the three-dimensional representation may be set with a common angular value in the conical surface to be in the same column of the two-dimensional image in order to overlay the arcuate incision over the eye. No matter how the three-dimensional representation is displayed on the two-dimensional eye image, the overlaid image is displayed for verification on a display of the system visible to the user (Action Block 914). Alternatively, a processor of the system 10 may perform the verification to determine if the proposed cut crosses the anterior or posterior of the cornea.

FIG. 36B is an exemplary display 1250 of the along the cut image overlaid on the image of the eye that is displayed to a user. The shaded area 1252 represents the proposed cut along the length of the cut. In particular, the cornea anterior 1254 and the cornea posterior 1256 are highlighted by a solid line and dashed line respectively, for a surgeon to verify that the shaded arcuate incision area 1252 does not penetrate the cornea posterior at any point. The arcuate incision 1252 is a projection of the three-dimensional surface onto the two-dimensional eye image that allows a surgeon to visually determine whether the incision will penetrate the posterior surface of the cornea at any point along the cut, instead of just at a single cross-section. The "along the cut" images may be generated using confocal imaging that produces one pixel per laser pulse or by OCT that produces vertical A scans of pixels for each pulse.

While the incision preview image of FIG. 36A displays only one plane of the incision, the incision preview of FIG. 36B displays the proposed incision along the entire length of the cut, thereby allowing a surgeon to more accurately verify whether the proposed cut will cross through the cornea at any point along the length of the cut.

In an embodiment, the laser surgery system 10 receives a plurality of parameters corresponding to the treatment planning, generates a three-dimensional representation of the treatment planning, maps the three-dimensional representation onto the image of the eye, and displays the mapped image for the treatment planning. The treatment planning includes an arcuate incision. The system can verify that the arcuate incision lies within the cornea. The received parameters may include a treatment axis and a treatment length transverse to the axis. The image of the eye is in a plane of the treatment axis and the treatment length. The three-dimensional representation is mapped onto the image of the eye by projecting the three-dimensional representation onto a two-dimensional space. The displayed image comprises a cornea of the eye including an anterior and posterior. The anterior and posterior of the cornea are highlighted. The treatment planning may also include one of a primary and side-port incision.

In an embodiment, the laser surgery system 10 focuses a first electromagnetic radiation beam to a focal point at a location in the eye and focuses a second electromagnetic radiation beam to a focal point at the location in the eye. A first intensity signal is generated indicative of an intensity of electromagnetic radiation reflected from the eye in response to the step of focusing the first electromagnetic radiation beam. A second intensity signal is generated indicative of an intensity of electromagnetic radiation reflected from the eye in response to the step of focusing the second electromagnetic radiation beam. One or more images of the eye are generated with the first and second intensity signals for treatment planning. A plurality of parameters are received corresponding to the treatment planning. A three-dimensional representation of the treatment planning is generated. The three-dimensional representation is mapped onto the image of the eye. The mapped image is displayed for the treatment planning.

In an embodiment, the laser surgery system includes a laser beam source configured to output a beam along a beam path toward the eye. A beam scanner is configured to direct the outputted beam to a plurality of locations in the eye. A sensor is positioned to receive reflected electromagnetic radiation from the eye. A processor is configured to generate one or more images of the eye with the first and second intensity signals for treatment planning. A user input device is configured to receive a plurality of parameters corresponding to the treatment planning. The processor generates a three-dimensional representation of the treatment planning, maps the three-dimensional representation onto the image of the eye. A display is configured to display the mapped image for the treatment planning.

Figure 37:
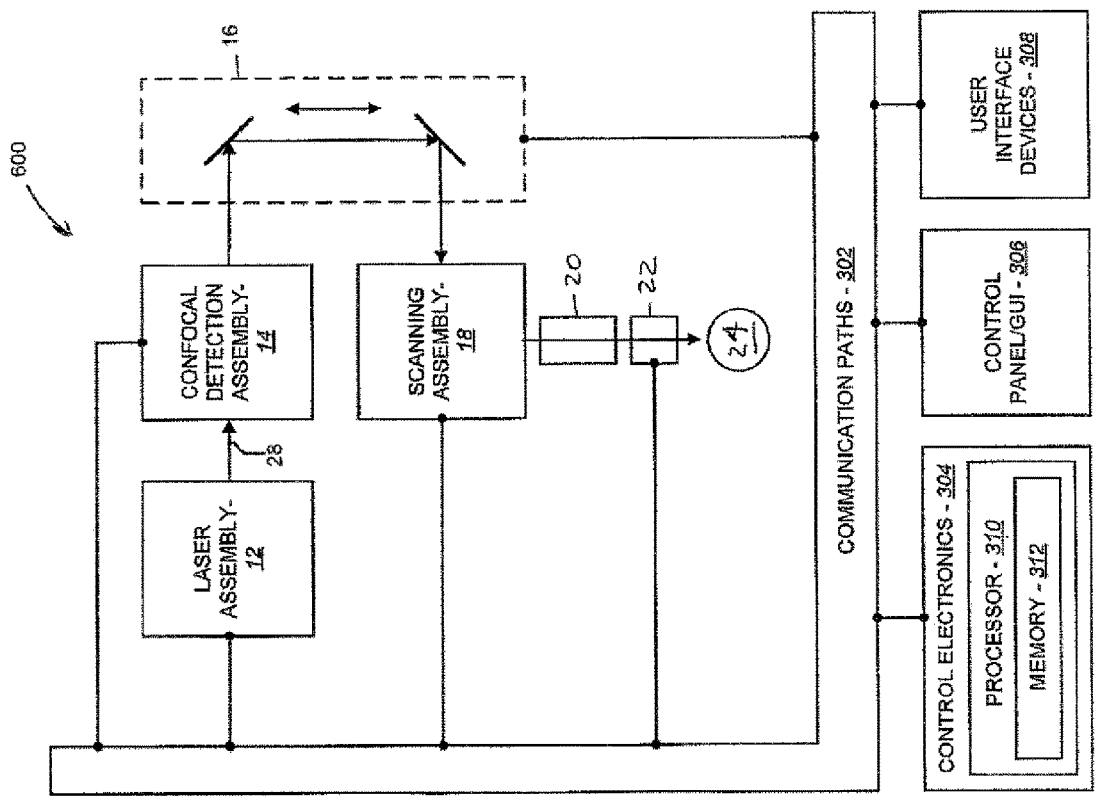
FIG. 37 is another schematic diagram of the laser surgery system of FIG. 1 according to an embodiment of the invention.
Figure 38:
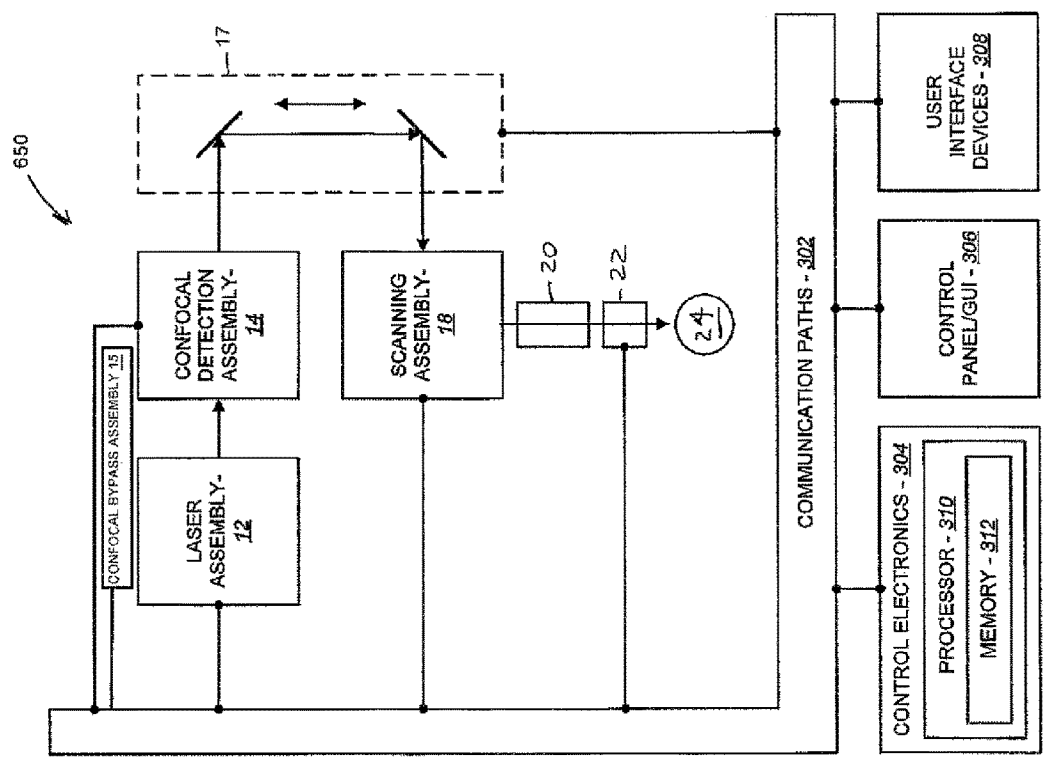
FIG. 38 is another schematic diagram of the laser surgery system of FIG. 23A and FIG. 23B according to an embodiment of the invention.

FIGS. 37 and 38 schematically illustrate a laser surgery system 600 and 650, respectively according to many embodiments. The laser surgery system 600 in FIG. 37 includes the laser assembly 12, the confocal detection assembly 14, the free-floating mechanism 16, the scanning assembly 18, the objective lens assembly 20, the patient interface 22, communication paths 302, control electronics 304, control panel/graphical user interface (GUI) 306, and user interface devices 308. The control electronics 304 includes processor 310, which includes memory 312. The patient interface 22 is configured to interface with a patient 24. The control electronics 304 is operatively coupled via the communication paths 302 with the laser assembly 12, the confocal detection assembly 14, the free-floating mechanism 16, the scanning assembly 18, the control panel/GUI 306, and the user interface devices 308. The laser surgery system 650 in FIG. 38 additionally includes the confocal bypass assembly 15, and substitutes the transfer optical path 17 for the free floating-mechanism 16. It should be noted, however, that free floating assembly 16 could also replace the transfer optical path 17 in laser surgery system 650.

The scanning assembly 18 can include a Z-scan device and an XY-scan device. The laser surgery system 300 may be configured to focus the electromagnetic radiation beam 28 to a focal point that is scanned in three dimensions. The Z-scan device may be operable to vary the location of the focal point in the direction of propagation of the beam 28. The XY-scan device may be operable to scan the location of the focal point in two dimensions transverse to the direction of propagation of the beam 28. Accordingly, the combination of the Z-scan device and the XY-scan device can be operated to controllably scan the focal point of the beam in three dimensions, including: within a tissue, e.g., eye tissue, of the patient 24. The scanning assembly 18 may be supported by the free-floating mechanism 16, which may accommodate patient movement, induced movement of the scanning assembly 18 relative to the laser assembly 12 and the confocal detection assembly 14 in three dimensions.

The patient interface 22 is coupled to the patient 24 such that the patient interface 22, the objective lens assembly 20, and the scanning assembly 18 move in conjunction with the patient 24. For example, in many embodiments, the patient interface 22 employs a suction ring that is vacuum attached to an eye of the patient 24. The suction ring may be coupled to the patient interface 22, for example, using vacuum.

The control electronics 304 controls the operation of and/or can receive input from the laser assembly 12, the confocal detection assembly 14, the free-floating assembly 16, the scanning assembly 18, the patient interface 22, the control panel/GUI 306, and the user interface devices 308 via the communication paths 302. The communication paths 302 can be implemented in any suitable configuration, including any suitable shared or dedicated communication paths between the control electronics 304 and the respective system components.

The control electronics 304 can include any suitable components, such as one or more processors, one or more field-programmable gate array (FPGA), and one or more memory storage devices. In many embodiments, the control electronics 304 controls the control panel/GUI 306 to provide for pre-procedure planning according to user specified treatment parameters as well as to provide user control over the laser eye surgery procedure.

The control electronics 304 can include a processor/controller 310 that is used to perform calculations related to system operation and provide control signals to the various system elements. A computer readable medium 312 is coupled to the processor 310 in order to store data used by the processor and other system elements. The processor 310 interacts with the other components of the system as described more fully throughout the present specification. In an embodiment, the memory 312 can include a look up table that can be utilized to control one or more components of the laser system surgery system 300.

The processor 310 can be a general purpose microprocessor configured to execute instructions and data such as a processor manufactured by the Intel Corporation of Santa Clara, Calif. It can also be an Application Specific Integrated Circuit (ASIC) that embodies at least part of the instructions for performing the method according to the embodiments of the present disclosure in software, firmware and/or hardware. As an example, such processors include dedicated circuitry, ASICs, combinatorial logic, other programmable processors, combinations thereof, and the like.

The memory 312 can be local or distributed as appropriate to the particular application. Memory 312 can include a number of memories including a main random access memory (RAM) for storage of instructions and data during program execution and a read only memory (ROM) in which fixed instructions are stored. Thus, the memory 312 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 308 can include any suitable user input/output device suitable to provide user input to the control electronics 304. For example, the user interface devices 308 can include devices such as a touch-screen display/input device, a keyboard, a footswitch, a keypad, a patient interface radio frequency identification (RFID) reader, an emergency stop button, a key switch, and so on.

The embodiments disclosed herein are well suited for combination with prior laser surgery systems, such as the Catalys Precision Laser System commercially available from Optimedica, and similar systems. Such systems can be modified in accordance with the teachings disclosed herein and to more accurately measure and treat the eye.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The confocal bypass assembly has been described here in relation to a specific laser eye surgery system. The bypass assemblies, such as those illustrated in FIG. 26, and as described herein, may be generally applied to other laser surgery systems in cases where it may be advantageous to separate an imaging mode from a treatment mode in specified surgery fields. They may also be applicable to non-surgical systems and methods, such as various materials processing systems, and micromachining systems.

Other embodiments include and incorporate imaging systems having laser assemblies, confocal detection assemblies, and systems that accommodate patient movement, including the eye interface, scanning assembly, free-floating mechanism described in U.S. Patent Application No. 61/780,736, filed Mar. 13, 2013 and U.S. patent application Ser. No. 14/191,095, filed Feb. 26, 2014, which takes priority to U.S. Patent Application No. 61/780,736. and U.S. Patent Application No. 61/780,881, filed Mar. 13, 2013 and U.S. patent application Ser. No. 14/190,827, filed Feb. 26, 2014, which takes priority to U.S. Patent Application No. 61/780,881.

All patents and patent applications cited herein are hereby incorporated by reference in their entirety.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

It is intended that the following claims define the scope of the invention and that methods and structures within the scope of these claims and their equivalents be covered thereby. It is to be understood that the present invention is not limited to the embodiment(s) described above and illustrated herein, but encompasses any and all variations explicitly and implicitly derived therefrom. Although not shown in the figures, multiple imaging steps can also be employed in between treatment steps to account for any changes in position and/or size due to treatment and further insure the accurate disposition of laser energy in the target tissue.

What is claimed is:

1. A method of using a laser eye surgical system, comprising:
    forming a pulsed laser beam with a laser beam source;
    directing the pulsed laser beam through shared optics and a patient interface to form a focal point in an eye to be sampled and deflecting back-reflected light from the eye to a confocal detector;
    receiving one or more parameters defining one or more ocular incisions;
    using an imaging apparatus, imaging the eye;
    identifying an expected scan location within the image of the eye corresponding to the one or more ocular incisions based on the one or more parameters;
    scanning the focal point of the pulsed laser beam in a region of the eye;
    using the imaging apparatus, detecting luminescence from the scanned region of the eye, wherein the luminescence is generated by the eye in response to the pulsed laser beam and has a wavelength different from a wavelength of the pulsed laser beam;
    identifying an actual scanned location within the image of the eye based on the detected luminescence; and
    generating a warning if a difference between the actual scanned location and the expected scan location is above a predetermined threshold value.

2. The method of claim 1, wherein the pulsed laser beam has a wavelength of 320 nm to 370 nm.

3. The method of claim 2, wherein the luminescence has a wavelength of 400 nm or longer.

4. The method of claim 1, wherein the patient interface has a cup with at least two openings and a ring inside the cup with an alignment indicator.

5. The method of claim 4, wherein the patient interface further includes a tool access portion, wherein the alignment indicator indicates a location of the tool access portion, wherein the ring further includes direction indicators of 90 degree increments around the inside of the cup, wherein the alignment indicator and the direction indicators are disposed at locations within a field of view of the imaging apparatus, the direction indicators being different than the alignment indicator.

6. The method of claim 5, wherein the direction indicators are colored differently than the alignment indicator.

7. The method of claim 5 wherein each of the direction indicators is at least one of a notch or a step.

8. The method of claim 4, wherein the alignment indicator in the ring is colored.

9. The method of claim 4, wherein the alignment indicator is a step in the ring.

10. The method of claim 4, wherein the alignment indicator is a notch in the ring.

* * * * *